US007763242B2

(12) United States Patent
Frankel

(10) Patent No.: US 7,763,242 B2
(45) Date of Patent: Jul. 27, 2010

(54) METHODS FOR TREATING MYELODYSPLASTIC SYNDROME WITH A HUMAN INTERLEUKIN-3-DIPHTHERIA TOXIN CONJUGATE

(75) Inventor: Arthur E. Frankel, Temple, TX (US)

(73) Assignees: Scott and White Memorial Hospital, Temple, TX (US); Scott, Sherwood and Brindley Foundation, Temple, TX (US)

( * ) Notice: Subject to any disclaimer, the term of this patent is extended or adjusted under 35 U.S.C. 154(b) by 0 days.

(21) Appl. No.: 11/899,747

(22) Filed: Sep. 7, 2007

(65) Prior Publication Data

US 2008/0138313 A1    Jun. 12, 2008

Related U.S. Application Data

(60) Provisional application No. 60/843,471, filed on Sep. 7, 2006, provisional application No. 60/932,772, filed on Jun. 1, 2007.

(51) Int. Cl.
*A61K 38/20* (2006.01)

(52) U.S. Cl. .............................. 424/85.2; 514/2; 514/8; 514/12; 514/885

(58) Field of Classification Search ........................ None
See application file for complete search history.

(56) References Cited

U.S. PATENT DOCUMENTS

| 4,675,382 | A | 6/1987 | Murphy et al. |
| 5,080,898 | A | 1/1992 | Murphy et al. |
| 5,616,482 | A | 4/1997 | Williams et al. |
| 5,668,255 | A | 9/1997 | Murphy |
| 5,677,148 | A | 10/1997 | Williams et al. |
| 5,703,039 | A | 12/1997 | Williams et al. |
| 5,763,250 | A | 6/1998 | Williams et al. |
| 5,843,633 | A | 1/1999 | Williams et al. |
| 5,863,891 | A | 1/1999 | Williams et al. |
| 5,932,471 | A | 8/1999 | Williams et al. |
| 6,004,528 | A | 12/1999 | Bergstein |
| 6,022,950 | A | 2/2000 | Murphy |
| 6,733,743 | B2 | 5/2004 | Jordan |
| 7,361,336 | B1 | 4/2008 | Bergstein |
| 7,427,400 | B2 | 9/2008 | Bergstein |
| 2004/0197337 | A1 | 10/2004 | Jordan |
| 2006/0083682 | A1 | 4/2006 | Bergstein |
| 2007/0036800 | A1 | 2/2007 | Bergstein |
| 2007/0036801 | A1 | 2/2007 | Bergstein |
| 2007/0036802 | A1 | 2/2007 | Bergstein |
| 2007/0036803 | A1 | 2/2007 | Bergstein |
| 2007/0036804 | A1 | 2/2007 | Bergstein |
| 2007/0041984 | A1 | 2/2007 | Bergstein |

FOREIGN PATENT DOCUMENTS

WO    WO/2008/030539    3/2008

OTHER PUBLICATIONS

Ganser et al (1992), Int J Clin Lab Res 22:125-128.*
Cheson et al (2000), Blood 96:3671-3674.*
U.S. Appl. No. 09/468,286, filed Dec. 20, 1999, Bergstein.
U.S. Appl. No. 11/899,690, filed Sep. 7, 2007, Bergstein.
Aldinucci et al., 2005, "The role of interleukin-3 in classical Hodgkin's disease" in Leukemia & Lymphoma; 46(3):303-11.
Alexander et al., 2000, "In vitro interleukin-3 binding to leukemia cells predicts cytotoxicity of a diphtheria toxin/IL-3 fusion protein" in Bioconjug Chem.; 11(4):564-8.
Alexander et al., 2001, "High affinity interleukin-3 receptor expression on blasts from patients with acute myelogenous leukemia correlates with cytotoxicity of a diphtheria toxin/IL-3 fusion protein" in Leuk Res.; 25(10):875-81.
Black et al., 2003, "Diphtheria toxin-interleukin-3 fusion protein (DT(388)IL3) prolongs disease-free survival of leukemic immunocompromised mice" in Leukemia; 17(1):155-9.
Bonnet et al., 1997, "Human acute myeloid leukemia is organized as a hierarchy that originates from a primitive hematopoietic cell" in Nature Medicine; 3(7):730-7.
Chandler et al., 1996, "Genetic engineering of immunotoxins" in Semin Pediatr Surg.: 5(3):206-11.
Cohen et al., 2004, "Toxicology and pharmacokinetics of DT388IL3, a fusion toxin consisting of a truncated diphtheria toxin (DT388) linked to human interleukin 3 (IL3), in cynomolgus monkeys" in Leuk Lymphoma; 45(8):1647-56.
Cohen et al., 2005, "Safety evaluation of DT388IL3, a diphtheria toxin/interleukin 3 fusion protein in the cynomolgus monkey" in Cancer Immunol Immunother.; 54(8):799-806.
Du et al., 1997, "New immunotoxins targeting CD123, a stem cell antigen on acute myeloid leukemia cells" in J Immunother; 30(6):607-13.
Feuring-Buske et al., 2002, "A diphtheria toxin-interleukin 3 fusion protein is cytotoxic to primitive acute myeloid leukemia progenitors but spares normal progenitors" in Cancer Res.; 62(6):1730-6.

(Continued)

*Primary Examiner*—Prema Mertz
(74) *Attorney, Agent, or Firm*—Jones Day

(57) ABSTRACT

The present invention provides methods for inhibiting interleukin-3 receptor-expressing cells, and, in particular, inhibiting the growth of such cells by using a diphtheria toxin-human interleukin-3 conjugate (DT-IL3) that is toxic to cells expressing the interleukin-3 receptor. In preferred embodiments, the DT-IL3 conjugate is a fusion protein comprising amino acids 1-388 of diphtheria toxin fused via a peptide linker to full-length, human interleukin-3. In certain embodiments, the methods of the present invention relate to the administration of a DT-IL3 conjugate to inhibit the growth of cancer cells and/or cancer stem cells in humans, which cells express one or more subunits of the interleukin-3 receptor. Exemplary cells include myeloid leukemia cancer stem cells. In other embodiments, the methods of the present invention relate to ex vivo purging of bone marrow or peripheral blood to remove cells that express one or more subunits of the interleukin-3 receptor such that the purged bone marrow or peripheral blood is suitable, e.g., for autologous stem cell transplantation to restore hematopoietic function.

56 Claims, 13 Drawing Sheets

OTHER PUBLICATIONS

Figure 1:
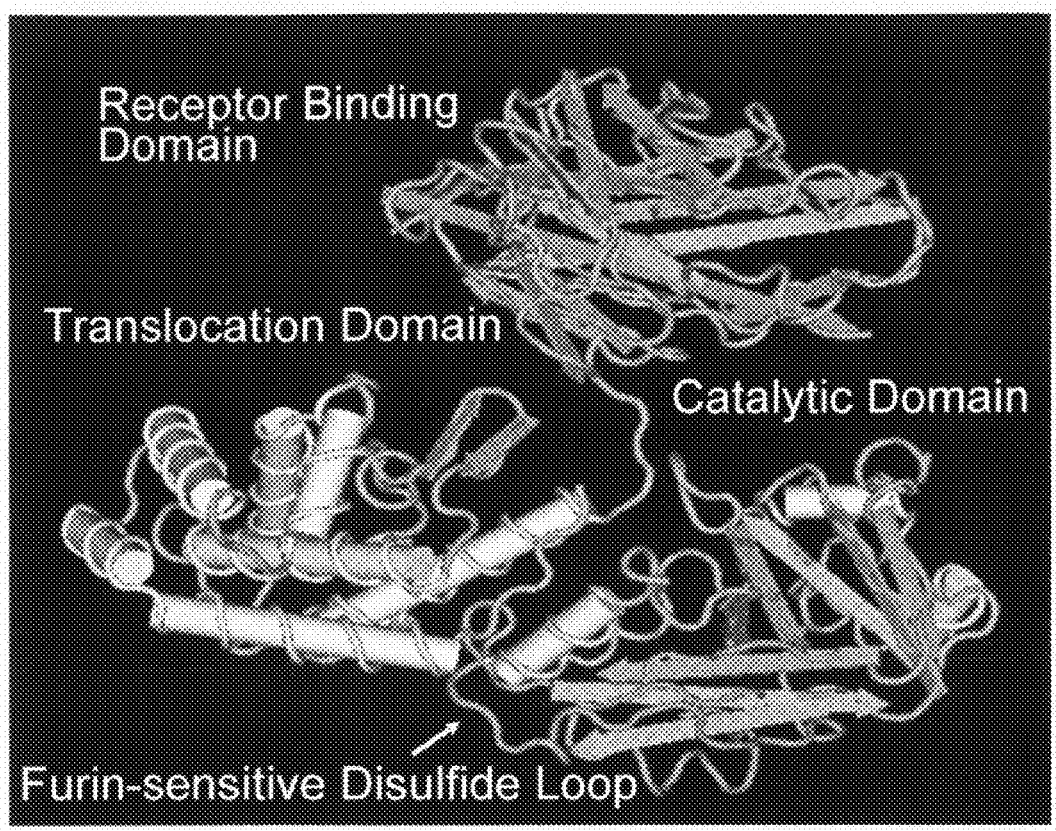

Florian et al., 2006, "Detection of molecular targets on the surface of CD34+/CD38− stem cells in various myeloid malignancies" in Leukemia & Lymphoma; 47(2):207-22.

Frankel et al., 2000, "Cell surface receptor-targeted therapy of acute myeloid leukemia: a review" in Cancer Biother Radiopharm.; 15(5):459-76.

Frankel et al., 2000, "Characterization of diphtheria fusion proteins targeted to the human interleukin-3 receptor" in Protein Eng.; 13(8):575-81.

Frankel et al., 2000, "Diphtheria toxin fused to human interleukin-3 is toxic to blasts from patients with myeloid leukemias" in Leukemia; 14(4):576-85.

Frankel et al., 2001, "Chimeric fusion proteins—diphtheria toxin-based" in Curr Opin Investig Drugs; 2(9):1294-301.

Frankel et al., 2001, "Immunotherapy of acute myeloid leukemia" in Curr Pharm Biotechnol.; 2(3):209-15.

Frankel et al., 2003, "Immunotoxin therapy of hematologic malignancies" in Semin Oncol.; 30(4):545-57.

Frankel et al., 2006, "Diphtheria toxin fusion protein DT388Il3 therapy of acute myeloid leukemia", at ASCO Annual Meeting, General Poster Session.

Hall et al., 2006, "Fresh frozen plasma and platelet concentrates may increase plasma anti-diphtheria toxin IgG concentrations: implications for diphtheria fusion protein therapy" in Cancer Immunol Immunother; 55(8):928-32.

Hogge et al., 2004, "The efficacy of diphtheria-growth factor fusion proteins is enhanced by co-administration of cytosine arabinoside in an immunodeficient mouse model of human acute myeloid leukemia" in Leuk Res.; 28(11):1221-6.

Hogge et al., 2006, "Variant diphtheria toxin-interleukin-3 fusion proteins with increased receptor affinity have enhanced cytotoxicity against acute myeloid leukemia progenitors" in Clin Cancer Res.; 12(4): 1284-91.

Hope et al., 2003, "Human acute myeloid leukemia stem cells" in Archives of Med. Res.; 34(6):507-14.

Jordan et al., 2000, "The interleukin-3 receptor alpha chain is a unique marker for human acute myelogenous leukemia stem cells" in Leukemia; 14:1777-84.

Kiser et al., 2001, "Oncogene-dependent engraftment of human myeloid leukemia cells in immunosuppressed mice" in Leukemia; 15(5):814-8.

Lhermitte et al., 2006, "Most immature T-ALLs express Ra-IL3 (CD123): possible target for DT-IL3 therapy" in Leukemia; 1-2.

Liu et al., 2004, "Diphtheria toxin fused to variant interleukin-3 provides enhanced binding to the interleukin-3 receptor and more potent leukemia cell cytotoxicity" in Exp Hematol.; 32(3):277-81.

Liu et al., 2005, "Interstitial diphtheria toxin-epidermal growth factor fusion protein therapy produces regressions of subcutaneous human glioblastoma multiforme tumors in athymic nude mice" in Clin Cancer Res.; 11(1):329-34.

Munoz et al., 2001, "Interleukin-3 receptor alpha chain (CD123) is widely expressed in hematologic malignancies" in Haematologica; 86(12):1261-9.

Otto, 1997, "Lung stem cells" in Int. J. Exp. Pathol.; 78(5):291-310.

Passegue et al., 2003, "Normal and leukemic hematopoiesis: are leukemias a stem cell disorder or a reacquisition of stem cell characteristics?" in Proc. Natl. Acad. Sci. U.S.A.; 100 (Suppl 1):11842-9.

Testa et al., 2005, "Diphtheria toxin fused to variant human interleukin-3 induces cytotoxicity of blasts from patients with acute myeloid leukemia according to the level of interleukin-3 receptor expression" in Blood; 106(7):2527-9.

Urieto et al., 2004, "Expression and purification of the recombinant diphtheria fusion toxin DT388IL3 for phase I clinical trials" in Protein Expr Purif.; 33(1):123-33.

Westcott et al., 2004, "Diphtheria toxin-murine granulocyte-macrophage colony-stimulating factor-induced hepatotoxicity is mediated by Kupffer cells" in Mol Cancer Ther.; 3(12):1681-9.

Wong et al., 2005, "Toxin conjugate therapy of cancer" in Semin Oncol.; 32(6):591-5.

Aldinucci et al., 2002, "Expression of functional interleukin-3 receptors on Hodgkin and Reed-Sternberg cells" in Am. J. Path.; 160(2):585-596.

Chan et al., 1996, "Reactivity of Murine Cytokine Fusion Toxin, Diphtheria Toxin$_{390}$-Murine Interleukin-3 (DT3$_{390}$-mIL-3), with Bone Marrow Progenitor Cells" in Blood; 88(4):1445-1456.

Liger et al., 1997, "Characterization and receptor specific toxicity of two diphtheria toxin-related interleukin-3 fusion proteins DAB389-mIL-3 and DAB389-(Gly4Ser)2-mIL-3" in FEBS Letters; 406:157-161.

Liger et al., 1998. "The diphtheria toxin transmembrane domain as a pH sensitive membrane anchor for human interleukin-2 and murine interleukin-3" in Protein Engineering 11(11):1111-1120.

Riccioni et al., 2004, "Immunophenotypic features of acute myeloid leukemias overexpressing the interleukin 3 receptor alpha chain" in Leukemia and Lymphoma; 45(8):1511-1517.

Testa et al., 2002, "Elevated expression of IL-3Ralpha in acute myelogenous leukemia is associated with enhanced blast proliferation, increased cellularity, and poor prognosis" in Blood; 100(8):2980-2988.

Testa et al., 2004, "Interleukin-3 receptor in acute leukemia" in Leukemia; 18:219-226.

Vallera et al., 1999, "Targeting myeloid leukemia with a DT(390)-mIL-3 fusion immunotoxin: ex vivo and in vivo studies in mice" in Protein Engineering; 12(9):779-785.

Wong et al., 2004, "Variant forms of human interleukin-3 (IL-3) linked to truncated Diphtheria toxin (DT388) have enhanced cytotoxicity against acute myeloid leukemia (AML) progenitor;" Blood 104:Abstract No. 1797, American Society of Hematology Meeting.

Misra et al., 2004, "The use of DT388-IL3 fusion protein in patients with refractory acute myeloid leukemia (AML);" Blood 104:Abstract 4513 (not selected for presentation), American Society of Hematology Meeting.

Frankel et al., "Phase I clinical study of diphtheria toxin-interleukin 3 fusion protein in patients with acute myeloid leukemia and myelodysplasia", in Leukemia & Lymphoma, Mar. 2008, 49(3): 543-553.

* cited by examiner

| Dose | 4 µg/kg | 5.32 µg/kg | 7.07 µg/kg | 9.4 µg/kg |
|---|---|---|---|---|
| $C_0$ (µg/ml) | 0.20141 | 0.3282 | 0.38322 | 0.3848 |
| Half Life (min) | 27.48 | 32.13 | 54.52 | 46.22 |
| AUC (µg·min/ml) | 13.51 | 32.09 | 41.79 | 52.53 |

Figure 7C:
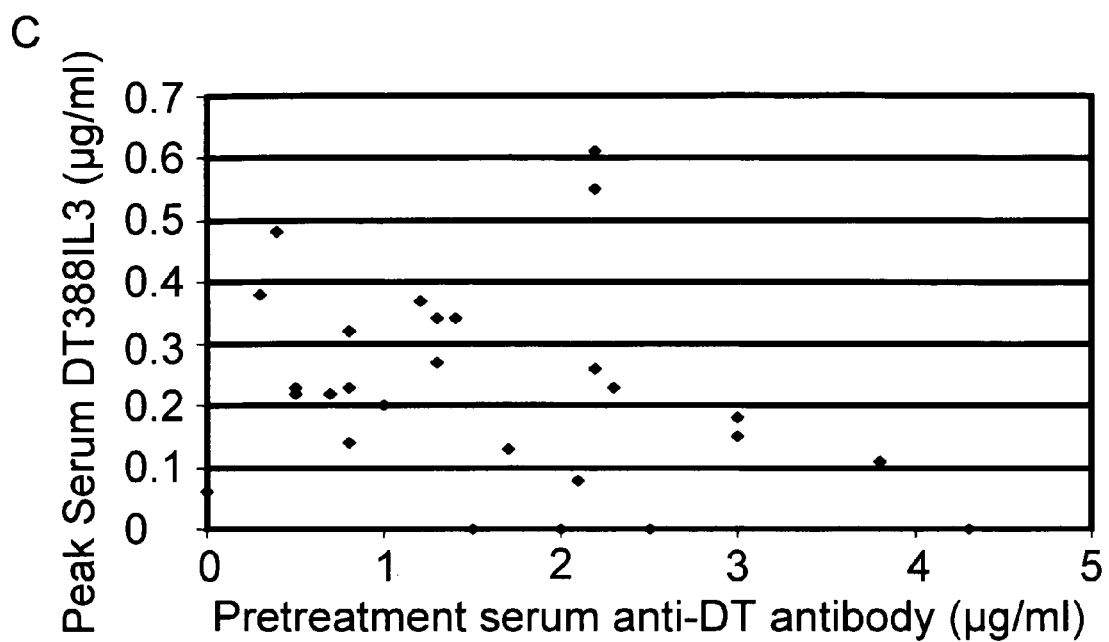
Figure 8A:
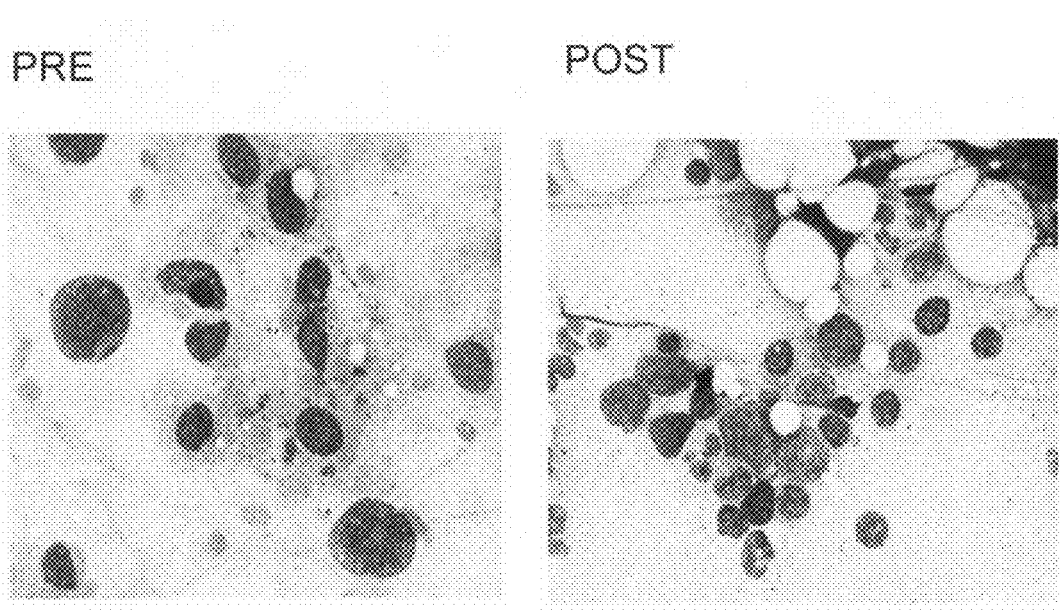
Figure 8B:
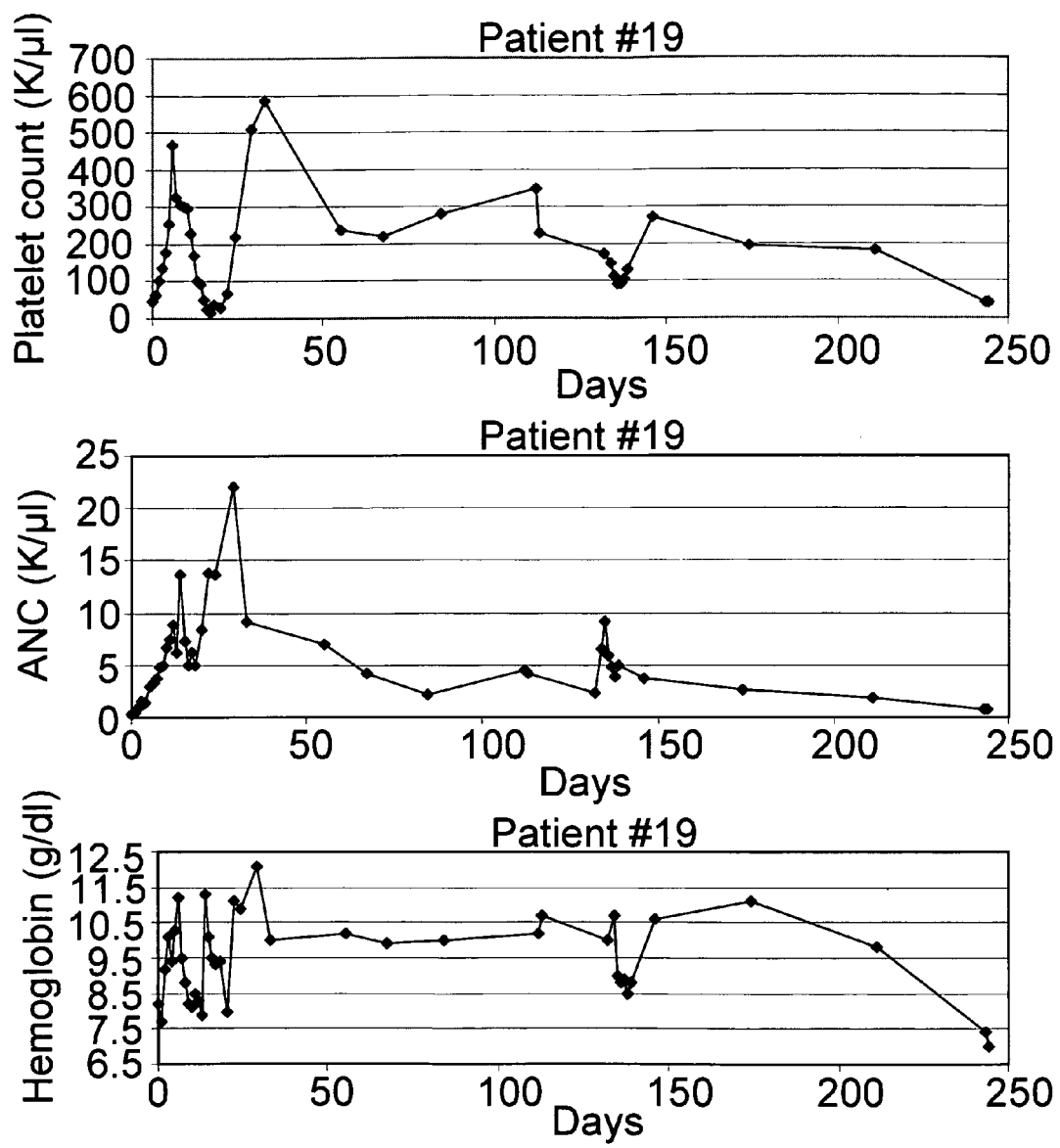
Figure 8C:
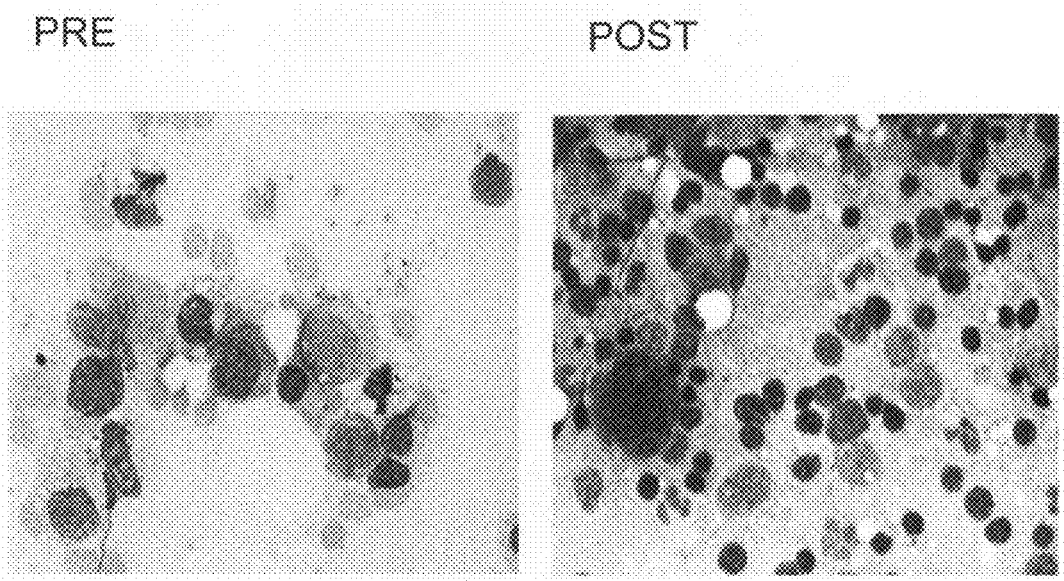
Figure 8D:
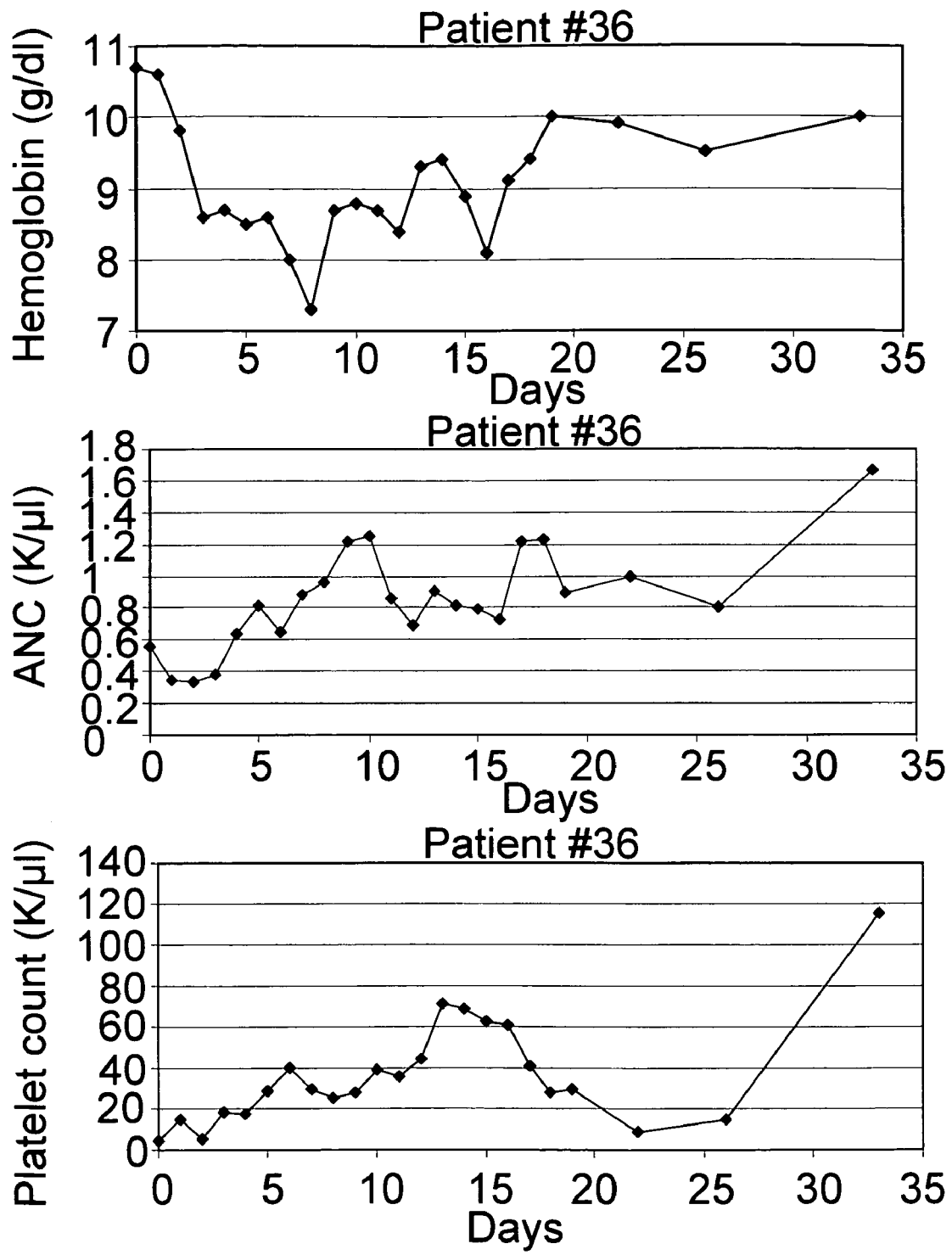

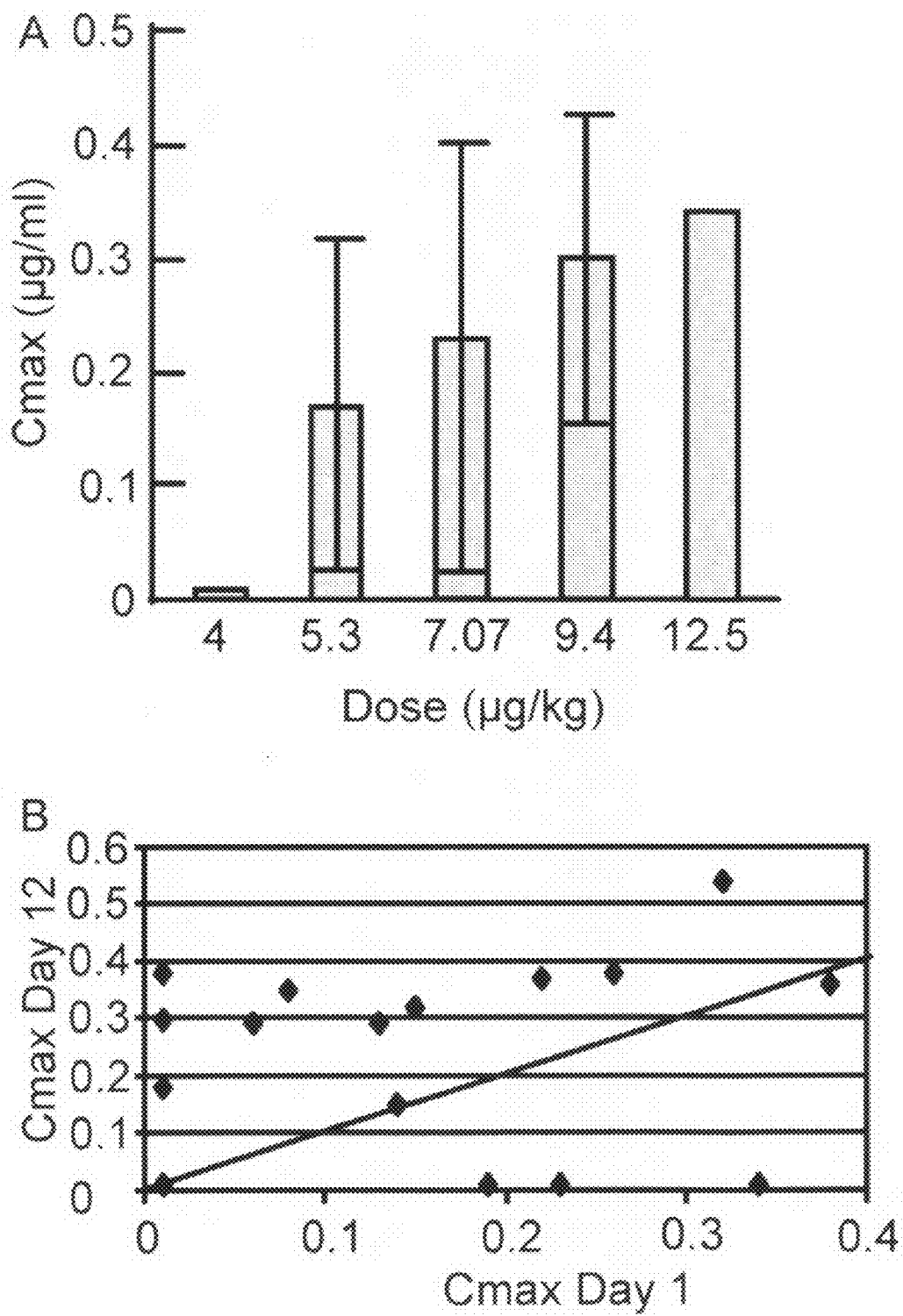
Figure 7A-B

METHODS FOR TREATING MYELODYSPLASTIC SYNDROME WITH A HUMAN INTERLEUKIN-3-DIPHTHERIA TOXIN CONJUGATE

This application claims and is entitled to priority benefit of U.S. provisional application Ser. No. 60/843,471, filed Sep. 7, 2006 and U.S. provisional application Ser. No. 60/932,772, filed Jun. 1, 2007, both of which are incorporated herein by reference in their entirety.

1. FIELD OF THE INVENTION

The present invention provides methods for targeting interleukin-3 receptor-expressing cells, and, in particular, inhibiting the growth of such cells by using a diphtheria toxin-human interleukin-3 conjugate (DT-IL3) that is toxic to cells expressing the interleukin-3 receptor. In preferred embodiments, the DT-IL3 conjugate is a recombinant construct wherein DNA encoding IL-3 is inserted in place of the receptor binding domain of the diphtheria toxin (the catalytic and translocation regions of the diphtheria toxin remaining intact) that when translated produces a protein comprising amino acids 1-388 of diphtheria toxin fused via a peptide linker to full-length, human interleukin-3. In certain embodiments, the methods of the present invention relate to the administration of a DT-IL3 conjugate to inhibit the growth of cancer cells and/or cancer stem cells in humans, which cells express one or more subunits of the interleukin-3 receptor. Exemplary cells include the cancer cells and cancer stem cells of acute myeloid leukemia and myelodysplastic syndrome. In other embodiments, the methods of the present invention relate to ex vivo purging of bone marrow or peripheral blood to remove cells that express one or more subunits of the interleukin-3 receptor such that the purged bone marrow or peripheral blood is suitable, e.g., for autologous stem cell transplantation back into the patient to restore hematopoietic function (e.g. as may be required following high dose chemotherapy for cancer).

2. BACKGROUND OF THE INVENTION

2.1 Cancer Therapy

Cancer is one of the most significant health conditions. The American Cancer Society's *Cancer Facts and Figures*, 2003, predicts over 1.3 million Americans will receive a cancer diagnosis this year. In the United States, cancer is second only to heart disease in mortality accounting for one of four deaths. In 2002, the National Institutes of Health estimated total costs of cancer totaled $171.6 billion, with $61 billion in direct expenditures. The incidence of cancer is widely expected to increase as the US population ages, further augmenting the impact of this condition. The current treatment regimens for cancer established in the 1970s and 1980s, have not changed dramatically. These treatments, which include chemotherapy, radiation and other modalities including newer targeted therapies, have shown limited overall survival benefit when utilized in most advanced stage common cancers since, among other things, these therapies primarily target tumor bulk.

More specifically, conventional cancer diagnosis and therapies to date have attempted to selectively detect and eradicate neoplastic cells that are largely fast-growing (i.e., cells that form the tumor bulk). Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Many conventional cancer chemotherapies (e.g., alkylating agents such as cyclophosphamide, antimetabolites such as 5-Fluorouracil, and plant alkaloids such as vincristine) and conventional irradiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of treatment. Despite the availability of a large variety of chemotherapeutic agents, these therapies have many drawbacks (see, e.g., Stockdale, 1998, "Principles Of Cancer Patient Management" in Scientific American Medicine, vol. 3, Rubenstein and Federman, eds., ch. 12, sect. X). For example, chemotherapeutic agents are notoriously toxic due to non-specific side effects on fast-growing cells whether normal or malignant; e.g. chemotherapeutic agents cause significant, and often dangerous, side effects, including bone marrow depression, immunosuppression, and gastrointestinal distress, etc.

Other types of traditional cancer therapies include surgery, hormonal therapy, immunotherapy, anti-angiogenesis therapy, targeted therapy (e.g., therapy directed to a cancer target such as Gleevec® and other tyrosine kinase inhibitors, Velcade®, Sutent®, et al.), and radiation treatment to eradicate neoplastic cells in a patient (see, e.g., Stockdale, 1998, "Principles of Cancer Patient Management," in Scientific American: Medicine, vol. 3, Rubenstein and Federman, eds., ch. 12, sect. IV). All of these approaches can pose significant drawbacks for the patient including a lack of efficacy (in terms of long-term outcome (e.g. due to failure to target cancer stem cells) and toxicity (e.g. due to non-specific effects on normal tissues)). Accordingly, new therapies for improving the long-term prospect of cancer patients are needed.

2.2 Cancer Stem Cells

Cancer stem cells comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e. those cancer cells that comprise the tumor bulk), cancer stem cells which are often slow-growing may be relatively more resistant than faster growing tumor bulk to conventional therapies and regimens. Cancer stem cells can express other features which make them relatively chemoresistant such as multi-drug resistance and anti-apoptotic pathways. The aforementioned would constitute a key reason for the failure of standard oncology treatment regimens to ensure long-term benefit in most patients with advanced stage cancers—i.e. the failure to adequately target and eradicate cancer stem cells. In some instances, a cancer stem cell(s) is the founder cell of a tumor (i.e., it is the progenitor of the cancer cells that comprise the tumor bulk).

Cancer stem cells have been identified in a large variety of cancer types. For instance, Bonnet et al., using flow cytometry were able to isolate the leukemia cells bearing the specific phenotype CD34+CD38−, and subsequently demonstrate that it is these cells (comprising <1% of a given leukemia), unlike the remaining 99+% of the leukemia bulk, that are able to recapitulate the leukemia from whenst it was derived when transferred into immunodeficient mice. See, e.g., "Human acute myeloid leukemia is organized as a hierarchy that originates from a primitive hematopoietic cell,"

Nat. Med. 3:730-737 (1997). That is, these cancer stem cells were found as <1 in 10,000 leukemia cells yet this low frequency population was able to initiate and serially transfer a human leukemia into severe combined immunodeficiency/non-obese diabetic (NOD/SCID) mice with the same histologic phenotype as in the original tumor.

Cox et al. identified small subfractions of human acute lymphoblastic leukemia (ALL) cells which had the phenotypes CD34+/CD10− and CD34+/CD19−, and were capable of engrafting ALL tumors in immunocompromised mice—i.e. the cancer stem cells. In contrast, no engraftment of the mice was observed using the ALL bulk, despite, in some cases, injecting 10-fold more cells. See Cox et al., "Characterization of acute lymphoblastic leukemia progenitor cells," *Blood* 104 (19): 2919-2925 (2004).

Multiple myeloma was found to contain small subpopulations of cells that were CD138− and, relative to the large bulk population of CD138+ myeloma cells, had greater clonogenic and tumorigenic potential. See Matsui et al., "Characterization of clonogenic multiple myeloma cells," *Blood* 103 (6): 2332. The authors concluded that the CD138− subpopulation of multiple myeloma was the cancer stem cell population.

Kondo et al. isolated a small population of cells from a C6-glioma cell line, which was identified as the cancer stem cell population by virtue of its ability to self-renew and recapitulate gliomas in immunocompromised mice. See Kondo et al., "Persistence of a small population of cancer stem-like cells in the C6 glioma cell line," *Proc. Natl. Acad. Sci. USA* 101:781-786 (2004). In this study, Kondo et al. determined that cancer cell lines contain a population of cancer stem cells that confer the ability of the line to engraft immunodeficient mice.

Breast cancers were shown to contain a small population of cells with stem cell characteristics (bearing surface markers CD44+CD24$^{low\ lin-}$). See Al-Hajj et al., "Prospective identification of tumorigenic breast cancer cells," *Proc. Natl. Acad. Sci. USA* 100:3983-3988 (2003). As few as 200 of these cells, corresponding to 1-10% of the total tumor cell population, are able to form tumors in NOD/SCID mice. In contrast, implantation of 20,000 cells that lacked this phenotype (i.e. the tumor bulk) was unable to re-grow the tumor.

A subpopulation of cells derived from human prostate tumors was found to self-renew and to recapitulate the phenotype of the prostate tumor from which they were derived thereby constituting the prostate cancer stem cell population. See Collins et al., "Prospective Identification of Tumorigenic Prostate Cancer Stem Cells," *Cancer Res* 65(23):10946-10951 (2005).

Fang et al. isolated a subpopulation of cells from melanoma with cancer stem cell properties. In particular, this subpopulation of cells could differentiate and self-renew. In culture, the subpopulation formed spheres whereas the more differentiated cell fraction from the lesions were more adherent. Moreover, the subpopulation containing sphere-like cells were more tumorigenic than the adherent cells when grafted into mice. See Fang et al., "A Tumorigenic Subpopulation with Stem Cell Properties in Melanomas," *Cancer Res* 65(20): 9328-9337 (2005).

Singh et al. identified brain tumor stem cells. When isolated and transplanted into nude mice, the CD133+ cancer stem cells, unlike the CD133− tumor bulk cells, form tumors that can then be serially transplanted. See Singh et al., "Identification of human brain tumor initiating cells," *Nature* 432: 396-401 (2004); Singh et al., "Cancer stem cells in nervous system tumors," *Oncogene* 23:7267-7273 (2004); Singh et al., "Identification of a cancer stem cell in human brain tumors," *Cancer Res.* 63:5821-5828 (2003).

Since conventional cancer therapies target rapidly proliferating cells (i.e., cells that form the tumor bulk) these treatments are believed to be relatively ineffective at targeting and impairing cancer stem cells. In fact, cancer stem cells, including leukemia stem cells, have indeed been shown to be relatively resistant to conventional chemotherapeutic therapies (e.g. Ara-C, daunorubicin) as well as newer targeted therapies (e.g. Gleevec®, Velcade®). Examples of cancer stem cells from various tumors that are resistant to chemotherapy, and the mechanism by which they are resistant, are described in Table 1 below.

TABLE 1

| CSC Type | Resistance | Mechanism | Reference |
| --- | --- | --- | --- |
| AML | Ara-C | Quiescence | Guzman. Blood '01 |
| AML | Daunorubicin | Drug Efflux, Anti-apoptosis | Costello. Cancer Res '00 |
| AML | Daunorubicin, mitoxantrone | Drug Efflux | Wulf. Blood '01 |
| AML | | Quiescence | Guan. Blood '03 |
| AML, MDS | | Anti-apoptosis | Suarez. Clin Cancer Res '04 |
| CML | | Quiescence | Holyoake. Blood '99 |
| CML | Gleevec ® | Quiescence | Graham. Blood '02 |
| Myeloma | Velcade ® | | Matsui. ASH 04 |

For example, leukemic stem cells are relatively slow-growing or quiescent, express multi-drug resistance genes, and utilize other anti-apoptotic mechanisms—features which contribute to their chemoresistance. See Jordan et al., "Targeting the most critical cells: approaching leukemia therapy as a problem in stem cell biology," *Nat. Clin. Pract. Oncol.* 2: 224-225 (2005). Further, cancer stem cells by virtue of their chemoresistance may contribute to treatment failure, and may also persist in a patient after clinical remission and these remaining cancer stem cells may therefore contribute to relapse at a later date. See Behbood et al., "Will cancer stem cells provide new therapeutic targets?" *Carcinogenesis* 26(4): 703-711 (2004). Therefore, targeting cancer stem cells is expected to provide for improved long-term outcomes for cancer patients. Accordingly, new therapeutic agents and/or regimens designed to target cancer stem cells are needed to reach this goal.

2.3 Acute Myeloid Leukemia

Approximately forty thousand patients per year develop acute myeloid leukemia (AML) in the U.S., Canada, and Europe. See, e.g., Jamal et al., *Cancer Statisitics* 56:106-130 (2006). AML is the most common leukemia in adults and the second most common leukemia in children. The prolonged hospitalizations associated with treatment and complications represent a significant share of health care costs in these regions. Further, even with combination induction and consolidation chemotherapy, most patients ultimately relapse and die from their disease or complications of treatment. See, e.g., Brune et al., "Improved leukemia-free survival after post-consolidation immunotherapy with histamine dihydrochloride and interleukin-2 in acute myeloid leukemia: results of a randomized phase III trial," *Blood* 108(1):88-96 (2006). Novel therapies are urgently needed. Selective targeting of AML cells stem cells may provide a safe and more effective therapy.

2.4 Myelodysplastic Syndrome

There are approximately 20,000 new cases of myelodysplastic syndrome (MDS) each year in the U.S. Patients with myelodysplastic syndromes typically have low blood cell counts in at least one or more of red blood cells, white blood cells, and platelets. Upon examination, the bone marrow usually is found to be dysplastic or hyperplastic, meaning there are too many poorly functioning blood stem cells in the marrow. A small percentage of MDS patients have hypoplastic bone marrow, meaning there are too few blood stem cells in the marrow, which make the disease look similar to aplastic anemia. Nearly half of people with MDS have no symptoms at time of diagnosis. When signs and symptoms do occur they can include anemia, weakness, fatigue, headache, bruising, increased bleeding, rash, fevers, mouth sores and lingering illness. MDS occurs at an increasing frequency in older people, but it can occur in children too. In less than a third of patients, MDS progresses over time to become acute leukemia. The average age of diagnosis is 70 years old. Treatments for MDS may vary considerably, depending on the type of MDS, the history of the patient, and the age and ability to tolerate certain treatment regimens. Treatment options include supportive care, chemotherapy-related agents, and stem cell transplantation (which is typically used only in patients under 50). However, the remission rate for existing treatments in relatively low, and new therapies are needed.

2.5 Interleukin-3

Interleukin-3 (IL-3) is a cytokine that supports the proliferation and differentiation of multi-potential and committed myeloid and lymphoid progenitors. See, e.g., Nitsche et al. "Interleukin-3 promotes proliferation and differentiation of human hematopoietic stem cells but reduces their repopulation potential in NOD/SCID mice," *Stem Cells* 21: 236-244 (2003). Human interleukin-3 mediates its effects by binding to human IL-3 receptor, which is a hetrodimeric structure and consists of an IL-3 binding α-subunit and a β-subunit. The α subunit is essential for ligand binding and confers specificity on the receptor. The β subunit is also shared by the granulocyte macrophage-colony stimulating factor (GM-CSF) and IL-5 receptors, and is required for high affinity ligand binding and signal transduction. Binding of IL-3 induces the heterodimerization of the α- and β-receptor subunits. The IL-3 receptor is over-expressed, relative to certain normal hematopoietic cells, on multiple hematological cancers including AML, B cell acute lymphocytic leukemia (B-ALL), hairy cell leukemia, Hodgkin's disease, and certain aggressive non-Hodgkin's lymphomas (Munoz. Haematologica 86:1261-1269, 2001; Riccioni. Leuk Lymphoma 46:303-311, 2005; Testa. Leukemia 18:219-226, 2004), as well as on the cancer stem cells of AML, myelodsyplastic syndrome (MDS), T cell ALL (T-ALL), and chronic myeloid leukemia (CML) (See Jordan et al. "The interleukin-3 receptor alpha chain is a unique marker for human acute myelogenous leukemia stem cells," *Leukemia* 14:1777-1784 (2000); Florian et al. "Detection of molecular targets on the surface of CD34+/CD38− stem cells in various myeloid malignancies," *Leuk. Lymphoma* 47:207-222 (2006); Lhermitte et al. "Most immature T-ALLs express Ra-IL3 (CD123): possible target for DT-IL3# therapy," 20:1908-1910 (2006); and Hogge et al. "Variant Diphtheria Toxin-Interleukin-3 Conjugates with Increased Receptor Affinity Have Enhanced Cytotoxicity against Acute Myeloid Leukemia Progenitors," *Clin. Caner Res.* 12:1284-1291 (2004).

2.6 Diphtheria Toxin

Figure 2:
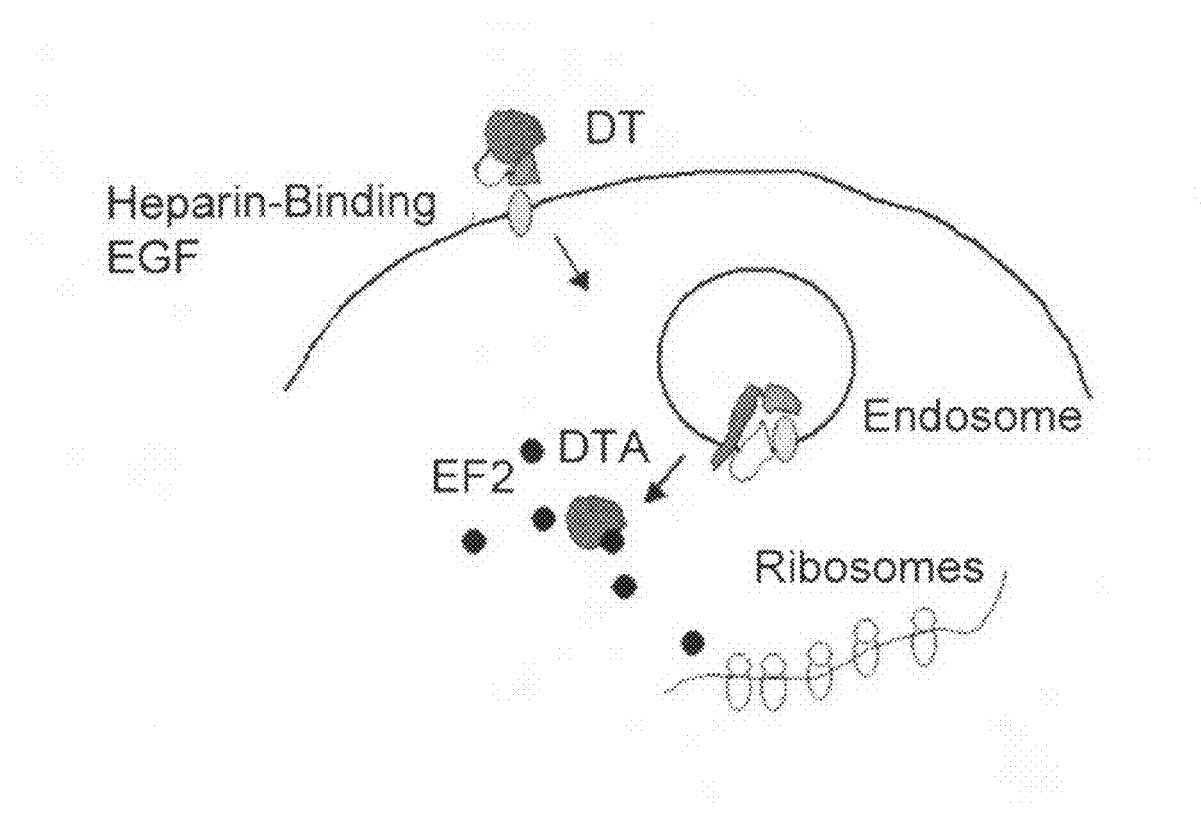

Diphtheria toxin (DT) is a 535 amino acid protein with three domains consisting of a catalytic domain (amino acids 1-186) connected by an arginine-rich disulfide loop to a translocation domain (amino acids 187-388) and a cell binding domain (amino acids 389-535; FIG. 1). See, e.g., Choe et al., "The crystal structure of diphtheria toxin," *Nature* 357: 216-222 (1992). Native DT binds to heparin-binding epidermal growth factor precursor and CD9 on the cell surface, undergoes clathrin-, dynamin- and ATP-dependent receptor-mediated endocytosis and, with endosome acidification by vesicular ATPase, the DT translocation domain undergoes protonation of acidic residues and spontaneous insertion into the vesicular membrane to form 18-22 Angstrom channels. The catalytic domain unfolds and is cleaved by furin in the vesicle and then the C-terminus of the catalytic domain transfers through the channel and binds to coatomer proteins, specifically β-COP. Protein disulfide isomerase reduces the linkage of the catalytic domain with the remainder of DT and the peptide passes into the cytosol. Hsp90 assists in refolding. The DT fragment then ADP-ribosylates elongation factor 2 leading to protein synthesis inactivation and cell death (FIG. 2). See Ratts et al., "A conserved motif in transmembrane helix 1 of diphtheria toxin mediates catalytic domain delivery to the cytosol," *Proc. Natl. Acad. Sci.* 102: 15635-15640 (2005).

2.7 Recombinant Diphtheria Toxin Conjugates

Recombinant protein-toxin conjugates represent a novel class of oncology biological agents that specifically target receptors on the surfaces of cancer cells. These agents typically consist of a truncated toxin, often including the catalytic and translocation (but not cell binding) domains, fused to a cell selective ligand which directs the toxin to the intended target. One such technology involves the recombinant diphtheria toxin (DT). DT is a 535 amino acid protein with three domains consisting of a catalytic domain (amino acids 1-186) connected by an arginine-rich disulfide loop to a translocation domain (amino acids 187-388) and a cell binding domain (amino acids 389-535; FIG. 1). See, e.g., Choe et al., "The crystal structure of diphtheria toxin", *Nature.* 357: 216-222 (1992). Native DT binds to heparin-binding epidermal growth factor precursor and CD9 on the cell surface, undergoes clathrin-, dynamin- and ATP-dependent receptor-mediated endocytosis, and, with endosome acidification by vesicular ATPase, the DT translocation domain undergoes protonation of acidic residues and spontaneous insertion into the vesicular membrane to form 18-22 Angstrom channels. The catalytic domain unfolds and is cleaved by furin in the vesicle and then the C-terminus of the catalytic domain transfers through the channel and binds β-COP. Protein disulfide isomerase reduces the linkage of the catalytic domain with the remainder of DT and the peptide passes into the cytosol. Hsp90 assists in refolding. The DT fragment then ADP-ribosylates elongation factor 2 leading to protein synthesis inactivation and cell death (FIG. 2). See Ratts et al., "A conserved motif in transmembrane helix 1 of diphtheria toxin mediates catalytic domain delivery to the cytosol" *Proc Natl Acad. Sci.,* 102: 15635-15640 (2005). A number of recombinant DT conjugates, utilizing a truncated form of DT, have been expressed, purified, and tested in cell culture and selective cell toxicity has been shown. One such recombinant toxin is the $DT_{388}$IL-3 conjugate, wherein the truncated DT maintains its catalytic and translocation, but not its cell binding domain.

$DT_{388}$IL-3 was constructed by fusing the gene encoding the catalytic and translocation domains of DT (amino acids 1-388) via a Met-His linker with human IL-3. See, e.g., Frankel et al., "Diphtheria toxin fused to human interleukin-3 is toxic to blasts from patients with myeloid leukemias," *Leukemia* 14: 576-585 (2000). $DT_{388}$IL-3 has been shown to be potently and selectively cytotoxic to IL-3R positive AML cell lines and primary leukemia cells derived from patients.

(See, Frankel et al., "Characterization of diphtheria fusion proteins targeted to the human interleukin-3 receptor," *Protein Eng.* 13: 575-581 (2000); Alexander et al., "High affinity interleukin-3 receptor expression on blasts from patients with acute myelogenous leukemia correlates with cytotoxicity of a diphtheria toxin/IL-3 fusion protein," *Leuk. Res.* 25: 875-881 (2001); Alexander et al. "In vitro interleukin-3 binding to leukemia cells predicts cytotoxicity of a diphtheria toxin/IL-3 fusion protein," *Bioconj. Chem.* 11:564-568 (2000); Feuring-Buske et al. "A diphtheria toxin interleukin-3 fusion protein is cytotoxic to primitive acute myeloid leukemia progenitors but spares normal progenitors," *Cancer Res.* 62: 1730-1736 (2002)). Additional studies found that high affinity variants of the $DT_{388}IL-3$ compound, named DT388-IL3[K116W] (based on the mutation of a lysine at amino acid 116 to tryptophan) and DT388IL3[Δ125-133] (based on a deletion of amino acids 125-133 in the IL3 domain), had increased potency against leukemia cells (See, Hogge et al., "Variant diphtheria toxin-interleukin-3 conjugates with increased receptor affinity have enhanced cytotoxicity against acute myeloid leukemia progenitors," *Clin. Cancer Res.* 12: 1284-1291 (2006); Testa et al., "Diphtheria toxin fused to variant human interleukin-3 induces cytotoxicity of blasts from patients with acute myeloid leukemia according to the level of interleukin-3 receptor expression," *Blood* 106: 2527-2529 (2005)). $DT_{388}IL-3$ also demonstrated in vivo anti-tumor efficacy in certain mouse models of human leukemia (See, Black et al., "Diphtheria toxin interleukin-3 fusion protein ($DT_{388}IL-3$) prolongs disease-free survival of leukemic immuno-compromised mice," *Leukemia;* 17: 155-159 (2003); Feuring-Buske et al. "A diphtheria toxin-interleukin-3 fusion protein is cytotoxic to primitive acute myeloid leukemia progenitors but spares normal progenitors," *Cancer Res.* 62: 1730-1736 (2002); and Hogge et al., "The efficacy of diphtheria-growth factor fusion proteins is enhanced by co-administration of cytosine arabinoside in an immunodeficient mouse model of human acute myeloid leukemia" *Leuk Res* 28: 1221-1226 (2004)). Safety was shown at therapeutically active doses in rodents and monkeys. (See, Black et al., "Diphtheria toxin interleukin-3 fusion protein ($DT_{388}IL-3$) prolongs disease-free survival of leukemic immuno-compromised mice," *Leukemia;* 17: 155-159 (2003); Cohen et al., "Toxicology and pharmacokinetics of $DT_{388}IL-3$, a fusion toxin consisting of a truncated diphtheria toxin ($DT_{388}$) linked to human interleukin-3 (IL-3), in cynomolgus monkeys" *Leuk Lymph,* 45: 1647-1656 (2004); Cohen et al., "Safety evaluation of $DT_{388}IL-3$, a diphtheria toxin-interleukin-3 fusion protein, in cynomolgus monkeys," *Cancer Immunol. Immunother.* 54: 799-806 (2005)). Clinical batches of $DT_{388}IL-3$ were prepared and an IND obtained (BB IND #11314). (See, Urieto et al., "Expression and purification of the recombinant diphtheria fusion toxin $DT_{388}IL-3$ for phase I clinical trials," *Protein Exp. Purif.* 33: 123-133 (2004).

3. SUMMARY OF THE INVENTION

The present invention is directed to a method for inhibiting interleukin-3 receptor-expressing cells comprising administering to a human in need of such inhibition a pharmaceutical composition comprising an amount of a human interleukin-3-diphtheria toxin conjugate effective in inhibiting said cells and a pharmaceutically acceptable carrier, with the proviso that the interleukin-3 receptor expressing cells are not acute myeloid leukemia cells, and wherein the cells express the alpha and beta subunits of the interleukin-3 receptor. In a preferred aspect of this embodiment, the growth of interleukin-3 receptor-expressing cells is inhibited.

In this or any of the embodiments of the present invention, the interleukin-3-diphtheria toxin conjugate can comprise the full-length, mature (lacking the signal peptide), human interleukin-3 connected by a covalent bond to diphtheria toxin. Preferably, the diphtheria toxin is modified in that the cell surface binding domain is deleted. For example, the conjugate is a chemical conjugate in which the diphtheria toxin portion (the catalytic and translocation domains of diphtheria toxin) and the interleukin-3 portion are chemically linked together either directly or through a chemical linker. Optionally, the conjugate is a genetic recombinant in which the conjugate is expressed as a single polypeptide. When the conjugate is a recombinant conjugate, the translated conjugate preferably comprises the catalytic and translocation domains of diphtheria toxin linked via a peptide bond to human interleukin-3. Most preferably, the conjugate comprises amino acids 1-388 of diphtheria toxin linked via a peptide linker to human interleukin-3.

In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. In a specific aspect, the conjugate can be administered at or below a dose that is the maximum dose tolerated without undue toxicity. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of 4 µg/kg per day or greater each time. In particular, the conjugate can be administered over a period of one or two weeks or greater. In aspects where the growth of interleukin-3 receptor-expressing cells is inhibited, the growth of the cells can be inhibited by at least 50%, at least 65%, at least 75%, at least 80%, at least 85%, at least 90%, at least 95% or by at least 99% as compared to a reference sample, i.e., a sample of cells not contacted with a conjugate of the invention.

In another embodiment, the present invention is directed to a method for inhibiting the growth of interleukin-3 receptor-expressing cells comprising administering to a human in need of such inhibition a pharmaceutical composition comprising an amount of an interleukin-3-diphtheria toxin conjugate effective in inhibiting said cells and a pharmaceutically acceptable carrier, in which the conjugate is administered at a dose greater than 4 µg/kg per day, and wherein the cells express the alpha subunit of the interleukin-3 receptor. In an aspect of this embodiment, the cells express both the alpha and the beta subunits of the interleukin-3 receptor.

In specific aspects of this embodiment, the conjugate can be administered at a dose in a range of greater than 4 µg/kg per day to about 20 µg/kg per day. In yet other aspects, the conjugate can be administered at a dose in a range of greater than 4 µg/kg per day to about 9 µg/kg per day. In yet other aspects, the conjugate can be administered at a dose in a range of about 4 µg/kg per day to about 12.5 µg/kg per day. In a specific aspect, the conjugate can be administered at or below a dose that is the maximum dose tolerated without undue toxicity. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of greater than 4 µg/kg per day each time. In particular, the conjugate can be administered over a period of two weeks or greater. In certain aspects, the growth of interleukin-3 receptor expressing cells can be inhibited by at least 50%, at least 65%, at least 75%, at least 80%, at least 85%, at least 90%, at least 95% or by at least 99% as compared to a reference sample, i.e., a sample of cells not contacted with a conjugate of the invention. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day.

In yet another embodiment, the present invention is directed to a method of treating, preventing and/or managing a disease or disorder that displays or is characterized by interleukin-3 receptor-expression comprising administering to a human in need of such treatment or prevention a pharmaceutical composition comprising an amount of an interleukin-3-diphtheria toxin conjugate effective to treat, prevent or manage the disease or disorder and a pharmaceutically acceptable carrier, with the proviso that the disease or disorder is not acute myeloid leukemia, and wherein the cells express the alpha and beta subunits of the interleukin-3 receptor. In one aspect of this embodiment, interleukin-3 receptor expression can be overexpression of one or more subunits of the interleukin-3 receptor on cells that normally express the interleukin-3 receptor. In another aspect, interleukin-3 receptor expression can be inappropriate expression of interleukin-3 receptor on cells that do not normally express one or more subunits of the interleukin-3 receptor. In yet another aspect, the disease or disorder that displays or is characterized by the presence or over-presence of a type of cell that expresses one or more subunits of the interleukin-3 receptor. Exemplary diseases or disorders that can be treated in this embodiment of the invention include, but are not limited to, allergic diseases or disorders, autoimmune diseases or disorders, inflammatory diseases or disorders, or cancers that are not acute myeloid leukemia. In aspects where the disease or disorder is cancer, the cancer can be refractory, or multidrug resistant. In some embodiments, the disease or disorder is MDS.

In still another embodiment, the present invention is directed to a method of treating, preventing and/or managing a disease or disorder that displays or is characterized by interleukin-3 receptor-expression comprising administering to a human in need of such treatment, prevention and/or management a pharmaceutical composition comprising an amount of an interleukin-3-diphtheria toxin conjugate effective to treat, prevent and/or manage the disease or disorder and a pharmaceutically acceptable carrier, wherein the cells express the alpha subunit of the interleukin-3 receptor. In one aspect of this embodiment, the cells express both the alpha and beta subunits of the interleukin-3 receptor. In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. In a specific aspect, the conjugate can be administered at or below a dose that is the maximum dose tolerated without undue toxicity. In one aspect of this embodiment, interleukin-3 receptor expression can be overexpression of interleukin-3 receptor on cells that normally express the interleukin-3 receptor. In another aspect, interleukin-3 receptor expression can be inappropriate expression of interleukin-3 receptor on cells that do not normally express the interleukin-3 receptor. In yet another aspect, the disease or disorder that displays or is characterized by the presence or over-presence of a type of cell that expresses the interleukin-3 receptor. Exemplary diseases or disorders that can be treated in this embodiment of the invention include, but are not limited to, allergic diseases or disorders, autoimmune diseases or disorders, inflammatory diseases or disorders, or cancers (including without limitation acute myeloid leukemia). In aspects where the disease or disorder is cancer, the cancer can be refractory, or multidrug resistant. In some embodiments, the disease or disorder is MDS.

In yet another embodiment of the present invention, a method for treating, preventing, and/or managing cancer is provided, which method comprises administering to a human in need of such treatment, prevention and/or management a pharmaceutical composition comprising an amount of an interleukin-3-diphtheria toxin conjugate effective to treat, prevent and/or manage the cancer and a pharmaceutically acceptable carrier, wherein the cancer cells express the alpha and beta subunits of the interleukin-3 receptor, with the proviso that the cancer is not acute myeloid leukemia. In yet another embodiment, the present invention is directed to a method for treating or preventing cancer, comprising administering to a human in need of such treatment or prevention a pharmaceutical composition comprising an amount of an interleukin-3-diphtheria toxin conjugate effective to treat or prevent the cancer and a pharmaceutically acceptable carrier, wherein the cancer stem cells express the alpha and beta subunits of the interleukin-3 receptor, with the proviso that the cancer is not acute myeloid leukemia.

In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. In a specific aspect, the conjugate can be administered at or below a dose that is the maximum dose tolerated without undue toxicity. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of 4 µg/kg per day or greater each time. In particular, the conjugate can be administered over a period of two weeks or greater. In other aspects, the growth of the cancer cells or the cancer stem cells can be inhibited by at least 50%, at least 65%, at least 75%, at least 80%, at least 85%, at least 90%, at least 95% or by at least 99% as compared to a reference sample, i.e., a sample of cells not contacted with a conjugate of the invention.

In other aspects of these embodiments, the human patient can be in a state of remission from the cancer. In yet other aspects, the human patient has been previously treated with the conjugate or has been previously treated with conventional chemotherapeutic agents or has radiation therapy. In yet another aspect, the human patient, concurrent with treatment with compounds of the invention, can be administered a conventional chemotherapeutic agent or can undergo radiation therapy. In other aspects, the human patient has no detectable levels of anti-diphtheria toxin antibodies prior to administration of a conjugate of the invention. In yet another aspect, the method further comprises administering a conventional chemotherapeutic agent. In particular aspects, the cancer is a non-hematologic cancer. Further the cancer can be refractory or multi-drug resistant.

In a specific aspect, the methods of this embodiment can further comprise monitoring the amount of cancer cells or cancer stem cells expressing the alpha subunit (in some embodiments, the alpha and beta subunits) of the interleukin-3 receptor in a sample derived from the human after administration of a conjugate of the invention and determining a further course of treatment based on the amount of cancer cells or cancer stem cells expressing the alpha subunit (in some embodiments, the alpha and beta subunits) present in the sample as compared to a reference sample or a sample of cancer cells or cancer stem cells obtained from the human before or during administration of the conjugate.

In yet another embodiment, the present invention is directed to a method for treating, preventing, and/or managing myeloid leukemia comprising administering to a human in need of such treatment, prevention, and/or management a pharmaceutical composition comprising an amount of an interleukin-3-diphtheria toxin conjugate effective to treat or prevent myeloid leukemia and a pharmaceutically acceptable carrier, in which the conjugate is administered at a dose of greater than 4 µg/kg, and wherein the myeloid leukemia cells express the alpha and beta subunits of the interleukin-3 receptor. In particular, the myeloid leukemia can be acute myeloid leukemia, chronic myeloid leukemia, or myelodysplastic syndrome. In some cases the myeloid leukemia may be refractory and/or multi-drug resistant. In certain aspects of this embodiment, the myeloid leukemia cells can express both the alpha and the beta subunits of the interleukin-3 receptor.

In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of greater than 4 µg/kg per day each time. In particular, the conjugate can be administered over a period of two weeks or greater. In certain aspects, the amount of myeloid leukemia cells can be decreased by at least 50%, at least 65%, at least 75%, at least 80%, at least 85%, at least 90%, at least 95% or by at least 99% as compared to a reference sample, i.e., a sample of cells not contacted with a conjugate of the invention. In a specific aspect of this embodiment, the conjugate can be administered at a dose of about 5.3 µg/kg per day, or at a dose of about 7.1 µg/kg per day, or at a dose of about 9 µg/kg per day.

In other aspects of these embodiments, the human patient can be in a state of remission of the myeloid leukemia. In yet other aspects, the human patient has been previously treated with the conjugate or has been previously treated with conventional chemotherapeutic agents or radiation therapy. In yet another aspect, the human patient concurrently can be administered a conventional chemotherapeutic agent or radiation therapy. In yet another aspect, the human patient is administered the conjugate 1 day, 2 days, 3 days, 4 days, 5 days, 6 days, 7 days, 2 weeks, 3 weeks, 1 month, 2 months, 3 months, 4 months, 5 months, 6 months, 9 months, or 12 months after receiving conventional chemotherapy. In other aspects, the human patient has low levels or no detectable levels of anti-diphtheria toxin antibodies prior to administration of a conjugate of the invention. In yet another aspect, the method further comprises administering a conventional chemotherapeutic agent.

In a specific aspect, the methods of this embodiment can further comprise monitoring the amount of myeloid leukemia cells expressing the alpha and/or beta subunits of the interleukin-3 receptor in a sample derived from the human after administration of a conjugate of the invention and determining a further course of treatment based on the amount of myeloid leukemia cells expressing the alpha and/or beta subunits present in the sample as compared to a reference sample or a sample of myeloid leukemia cells obtained from the human before or during administration of the conjugate.

In a specific aspect, the methods of this embodiment can further comprise monitoring the amount of myeloid leukemia cells expressing the alpha subunit of the interleukin-3 receptor in a sample derived from the human after administration of a conjugate of the invention and determining a further course of treatment based on the amount of myeloid leukemia cells expressing the alpha subunit present in the sample as compared to a reference sample or a sample of myeloid leukemia cells obtained from the human before or during administration of the conjugate.

The present invention is also directed to a method for preventing a relapse of cancer in a human previously treated for the cancer, comprising administering to a human in need of such prevention who had been previously treated for cancer, a pharmaceutical composition comprising an amount of an interleukin-3-diphtheria toxin conjugate effective to prevent the relapse of the cancer and a pharmaceutically acceptable carrier, wherein the cancer cells or the cancer stem cells express the alpha and beta subunits of the interleukin-3 receptor, with the proviso that the cancer is not myeloid leukemia. In another embodiment, the invention is directed to a method for preventing a relapse of myeloid leukemia in a human previously treated for myeloid leukemia, comprising administering to a human in need of such prevention who had been previously treated for myeloid leukemia, a pharmaceutical composition comprising an amount of an interleukin-3-diphtheria toxin conjugate effective to prevent the relapse of myeloid leukemia and a pharmaceutically acceptable carrier, in which the conjugate is administered at a dose of greater than 4 µg/kg per day.

In yet another embodiment, a method for preventing a relapse of cancer in a human in remission from such cancer is provided, which method comprises administering to a human in need of such prevention who is in remission from said cancer, a pharmaceutical composition comprising an amount of an interleukin-3-diphtheria toxin conjugate effective to prevent the relapse of the cancer and a pharmaceutically acceptable carrier, wherein the cancer cells or the cancer stem cells express the alpha and beta subunits of the interleukin-3 receptor, with the proviso that the cancer is not myeloid leukemia. Another embodiment of the invention is directed to a method for preventing a relapse of myeloid leukemia in a human in remission from myeloid leukemia, comprising administering to a human in need of such prevention who is in remission from myeloid leukemia, a pharmaceutical composition comprising an amount of an interleukin-3-diphtheria toxin conjugate effective to prevent the relapse of myeloid leukemia and a pharmaceutically acceptable carrier, in which the conjugate is administered at a dose of greater than 4 µg/kg.

The present invention is also directed to a method for purging bone marrow or peripheral blood prior to autologous stem cell transplant, comprising contacting ex vivo bone marrow or peripheral blood obtained from a human with a composition comprising an amount of an interleukin-3-diphtheria toxin conjugate for a time sufficient to significantly purge the bone marrow or peripheral blood of cells expressing the alpha and beta subunits of the interleukin-3 receptor. In an aspect of this embodiment, the amount of bone marrow or peripheral blood cells expressing a beta subunit of the interleukin-3 receptor after contacting with a conjugate of the invention can be decreased by at least 50%, 60%, 75%, 80%, 90%, 95%, or by at least 99%. The present invention is also directed to a method for performing an autologous bone marrow or peripheral blood stem cell transplant, comprising administering to a human an amount of significantly purged bone marrow or peripheral blood effective to reconstitute hematopoietic function in said human, wherein said purged bone marrow or peripheral blood is bone marrow or peripheral blood obtained from said human previously contacted with an amount of an interleukin-3-diphtheria toxin conjugate for a time sufficient to significantly purge the bone marrow or peripheral blood of cells expressing the alpha and beta subunits of the interleukin-3 receptor. Further, the present invention is directed to a composition comprising purged bone marrow or peripheral blood, wherein said purged bone marrow or peripheral blood is bone marrow or peripheral blood obtained from a human and contacted ex vivo with an amount of an interleukin-3-diphtheria toxin conjugate for a time sufficient to significantly purge the bone marrow or peripheral blood of cells expressing the alpha and beta subunits of the interleukin-3 receptor, and then possibly re-introducing the bone marrow or peripheral blood cells back into the patient. In one aspect, the composition can further comprise a pharmaceutically acceptable carrier.

In certain embodiments of the invention, conventional chemotherapy and the methods of the invention may be used sequentially. In a specific aspect of this embodiment, the patient's leukemia blasts are first reduced by use of conventional chemotherapy, followed by a regimen comprising administration of an amount of an interleukin-3-diphtheria toxin conjugate for a time sufficient to significantly stabilize, reduce, or eradicate cancer stem cells expressing the alpha and beta subunits of the interleukin-3 receptor.

3.1 DEFINITIONS

As used herein, the term "agent" refers to any molecule, compound, and/or substance for use in the prevention, treatment, management and/or diagnosis of cancer, including the diphtheria toxin-interleukin-3 conjugate of the invention.

As used herein, the term "conjugate of the invention" refers to interleukin-3 or a portion, analog or derivative thereof that binds to the interleukin-3 receptor or subunit thereof conjugated to diphtheria toxin, a portion thereof or an analog thereof. Unless otherwise indicated, the terms "compound of the invention" and "composition of the invention" are used as alternatives for the term "conjugate of the invention."

As used herein, the term "amount," as used in the context of the amount of a particular cell population or cells, refers to the frequency, quantity, percentage, relative amount, or number of the particular cell population or cells.

As used herein, the terms "about" or "approximately," unless otherwise indicated, refer to a value that is no more than 10% above or below the value being modified by the term.

As used herein, the term "significantly," as used in the context of purging of the bone marrow or peripheral blood of cells expressing the alpha and beta subunits of the interleukin-3 receptor, refers to a decrease in cells expressing the alpha and beta subunits of the interleukin-3 receptor by at least 50%, 60%, 75%, 80%, 90%, 95%, or 99%.

As used herein, the term "small reduction," in the context of a particular cell population (e.g., circulating endothelial cells and/or circulating endothelial progenitors) refers to less than a 30% reduction in the cell population (e.g., the circulating endothelial cell population and/or the circulating endothelial progenitor population).

As used herein, the phrase "diagnostic agent" refers to any molecule, compound, and/or substance that is used for the purpose of diagnosing cancer. Non-limiting examples of diagnostic agents include antibodies, antibody fragments, or other proteins, including those conjugated to a detectable agent. As used herein, the term "detectable agents" refer to any molecule, compound and/or substance that is detectable by any methodology available to one of skill in the art. Non-limiting examples of detectable agents include dyes, gases, metals, or radioisotopes. As used herein, diagnostic agent and "imaging agent" are equivalent terms.

As used herein, the phrase "prophylactic agent" refers to any molecule, compound, and/or substance that is used for the purpose of preventing cancer. Examples of prophylactic agents include, but are not limited to, proteins, immunoglobulins (e.g., multi-specific Igs, single chain Igs, Ig fragments, polyclonal antibodies and their fragments, monoclonal antibodies and their fragments), binding proteins, chemospecific agents, chemotoxic agents (e.g., anti-cancer agents), proliferation based therapy, and small molecule drugs.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, radiation, chemotherapy, anti-angiogenic agents, and small molecule drugs.

As used herein, the term "proliferation based therapy" refers to any molecule, compound, substance, and/or method that differentially impairs, inhibits or kills rapidly proliferating cell populations (e.g., cancer cells) in comparison with cell populations that divide more slowly. Proliferation based therapies may include, but are not limited to those chemotherapeutic and radiation therapies that are typically used in oncology. A proliferation based agent may differentially impair, inhibit or kill rapidly proliferating cells by any mechanism known to one skilled in the art including, but not limited to, disrupting DNA function (including DNA replication), interfering with enzymes involved in DNA repair, intercalating DNA, interfering with RNA transcription or translation, interfering with enzymes involved with DNA replication, interfering with a topoisomerase, such as topoisomerase II, interfering with mitosis, and inhibiting enzymes necessary for the synthesis of proteins needed for cellular replication. Specific examples of proliferation based therapies include, but are not limited to, alkylating agents, nitrosoureas, antimetabolites, antibiotics, procarbazine, hydroxyurea, platinum-based agents, anthracyclins, topoisomerase II inhibitors, spindle poisons, and mitotic inhibitors.

As used herein, the term "cancer" refers to a neoplasm or tumor resulting from abnormal uncontrolled growth of cells. Non-limiting examples include those cancers described in Section 5.3.2. The term "cancer" encompasses a disease involving both pre-malignant and malignant cancer cells. In some embodiments, cancer refers to a localized overgrowth of cells that has not spread to other parts of a subject, i.e., a localized, or at times benign, tumor. In other embodiments, cancer refers to a malignant tumor, which has invaded and destroyed neighboring body structures and spread to distant sites. In yet other embodiments, the cancer is associated with a specific cancer antigen.

As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "cancer stem cell(s)" refers to a cell that can be a progenitor of a highly proliferative cancer cell. A cancer stem cell has the ability to re-grow a tumor as demonstrated by its ability to form tumors in immunocompromised mice, and typically to form tumors upon subsequent serial transplantation in immunocompromised mice. Cancer stem cells are also typically slow-growing relative to the bulk of a tumor; that is, cancer stem cells are generally quiescent. In certain embodiments, but not all, the cancer stem cell may represent approximately 0.1 to 10% of a tumor.

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three, or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, (12) an increase in the number of patients in remission, (13) an increase in the length or duration of remission, (14) a decrease in the recurrence rate of cancer, (15) an increase in the time to recurrence of cancer, and (16) an amelioration of cancer-related symptoms and/or quality of life.

As used herein, the phrase "elderly human" refers to a human between 65 years old or older, preferably 70 years old or older.

As used herein, the phrase "human adult" refers to a human 18 years of age or older.

As used herein, the phrase "human child" refers to a human between 24 months of age and 18 years of age.

As used herein, the phrase "human infant" refers to a human less than 24 months of age, preferably less than 12 months of age, less than 6 months of age, less than 3 months of age, less than 2 months of age, or less than 1 month of age.

As used herein, the phrase "human patient" refers to any human, whether elderly, an adult, child or infant.

As used herein, the term "refractory" is most often determined by failure to reach clinical endpoint, e.g., response, extended duration of response, extended disease free, survival, relapse free survival, progression free survival and overall survival. Another way to define being refractory to a therapy is that a patient has failed to achieve a response to a therapy such that the therapy is determined to not be therapeutically effective.

As used herein, the term "specifically binds to an antigen" and analogous terms refer to peptides, polypeptides, proteins, fusion proteins and antibodies or fragments thereof that specifically bind to an antigen or a fragment and do not specifically bind to other antigens. A peptide, polypeptide, protein, or antibody that specifically binds to an antigen may bind to other peptides, polypeptides, or proteins with lower affinity as determined by, e.g., immunoassays, BIAcore, or other assays known in the art. Antibodies or fragments that specifically bind to an antigen may be cross-reactive with related antigens. Preferably, antibodies or fragments that specifically bind to an antigen do not cross-react with other antigens. An antibody binds specifically to an antigen when it binds to the antigen with higher affinity than to any cross-reactive antigen as determined using experimental techniques, such as radioimmunoassays (RIAs) and enzyme-linked immunosorbent assays (ELISAs). See, e.g., Paul, ed., 1989, Fundamental Immunology, $2^{nd}$ ed., Raven Press, New York at pages 332-336 for a discussion regarding antibody specificity.

As used herein, the term "in combination" in the context of the administration of a therapy to a subject refers to the use of more than one therapy (e.g., prophylactic and/or therapeutic). The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the terms "manage," "managing," and "management" in the context of the administration of a therapy to a subject refer to the beneficial effects that a subject derives from a therapy (e.g., a prophylactic or therapeutic agent) or a combination of therapies, while not resulting in a cure of cancer. In certain embodiments, a subject is administered one or more therapies (e.g., one or more prophylactic or therapeutic agents) to "manage" cancer so as to prevent the progression or worsening of the condition.

As used herein, the term "marker" in the context of a cell or tissue (e.g. a normal or cancer cell or tumor) means any antigen, molecule or other chemical or biological entity that is specifically found in or on a tissue that it is desired to identified or identified in or on a particular tissue affected by a disease or disorder. In specific embodiments, the marker is a cell surface antigen that is differentially or preferentially expressed by specific cell types. For example, a leukemia cancer stem cell differentially expresses CD123 relative to a normal hematopoietic stem cell.

As used herein, the term "marker phenotype" in the context of a tissue (e.g., a normal or cancer cell or a tumor cell) means any combination of antigens (e.g., receptors, ligands, and other cell surface markers), molecules, or other chemical or biological entities that are specifically found in or on a tissue that it is desired to identify a particular tissue affected by a disease or disorder. In specific embodiments, the marker phenotype is a cell surface phenotype. In accordance with this embodiment, the cell surface phenotype may be determined by detecting the expression of a combination of cell surface antigens. Non-limiting examples of cell surface phenotypes of cancer stem cells of certain tumor types include $CD34^+/CD38^-$, $CD123+$, $CD44^+/CD24^-$, $CD133^+$, $CD34^+/CD10^-/CD19^-$, $CD138^-/CD34^-/CD19^+$, $CD133^+/RC2^+$, $CD44^+/\alpha_2\beta_1^{hi}/CD133^+$, CLL-1, SLAMs, and other cancer stem cell surface phenotypes mentioned herein, as well as those that are known in the art.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a cancer or a symptom thereof in a subject resulting from the administration of a therapy (e.g., a prophylactic or therapeutic agent), or a combination of therapies (e.g., a combination of prophylactic or therapeutic agents). In some embodiments, such terms refer to one, two, three, or more results following the administration of one or more therapies: (1) a stabilization, reduction or elimination of the cancer stem cell population, (2) a stabilization, reduction or elimination in the cancer cell population, (3) an increase in response rate, (4) an increase in the length or duration of remission, (5) a decrease in the recurrence rate of cancer, (6) an increase in the time to recurrence of cancer, (7) an increase in the disease-free, relapse-free, progression-free, and/or overall survival of the patient, and (8) an amelioration of cancer-related symptoms and/or quality of life. In specific embodiments, such terms refer to a stabilization, reduction or elimination of the cancer stem cell population.

As used herein, the terms "fragment" and "portion" in the context of proteinaceous agents refer to an amino acid sequence comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of a protein or polypeptide.

As used herein, the term "predetermined reference range" refers to a reference range for the particular biological entity, e.g., cancer stem cell, for a subject or a population of subjects. Each laboratory may establish its own reference range for each particular assay, or a standard reference range for each assay may be made available and used locally, regionally, nationally, or worldwide or may be patient-specific. In one specific embodiment, the term refers to a reference range for the amount of cancer stem cells in a patient (e.g., as determined by in vivo imaging) or a specimen from a patient. In another specific embodiment, the term refers to a reference range for the amount of cancer cells in a patient (e.g. as described by in vivo imaging) or a specimen from a patient.

As used herein, the term "prophylactically effective regimen" refers to an effective regimen for dosing, timing, frequency and duration of the administration of one or more therapies for the prevention of cancer or a symptom thereof. In a specific embodiment, the regimen achieves one, two, three, or more of the following results: (1) a stabilization, reduction or elimination of the cancer stem cell population, (2) a stabilization, reduction or elimination in the cancer cell population, (3) an increase in response rate, (4) an increase in the length or duration of remission, (5) a decrease in the recurrence rate of cancer, (6) an increase in the time to recurrence of cancer, (7) an increase in the disease-free, relapse-free, progression-free, and/or overall survival of the patient, and (8) an amelioration of cancer-related symptoms and/or quality of life.

As used herein, the term "stabilizing" and analogous terms, when used in the context of a cancer stem cell population or cancer cell population, refer to the prevention of an increase in the cancer stem cell population or cancer cell population, respectively. In other words, the amount of cancer stem cells or the amount of cancer cells that a cancer is composed of is maintained, and does not increase, or increases by less than 10%, preferably less than 5%.

As used herein, the term "therapeutically effective regimen" refers to a regimen for dosing, timing, frequency, and duration of the administration of one or more therapies for the treatment and/or management of cancer or a symptom thereof. In a specific embodiment, the regimen achieves one, two, three, or more of the following results: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) a increase in the number of patients in remission.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a cancer or one or more symptoms thereof. In certain embodiments, the terms "therapy" and "therapies" refer to chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a cancer or one or more symptoms thereof.

As used herein, the terms "treat," "treatment," and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. In specific embodiments, such terms refer to one, two or three or more results following the administration of one, two, three, or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

4. BRIEF DESCRIPTION OF FIGURES

FIG. 1. A model of the three-dimensional structure of diphtheria toxin (DT) based on the X-ray crystallographic coordinates. Alpha-carbon backbone is shown with flat arrows for beta-sheets and cylinders for alpha-helices. Catalytic, translocation and receptor-binding domains are shown.

FIG. 2. Mechanism of cell intoxication by DT. Steps include (a) cell binding, (b) receptor-mediated endocytosis, (c) low pH, furin and thioredoxin reductase, beta-COP, and Hsp90 mediated translocation, (d) refolding and ADP ribosylation of EF2, and (e) cell death. (Ratts et al., "A conserved motif in transmembrane helix 1 of diphtheria toxin mediates catalytic domain delivery to the cytosol," *Proc. Natl. Acad. Sci. U.S.A.* 102:15635-15640 (2005).

Figure 3:

FIG. 3. A model of $DT_{388}$IL-3. Alpha-carbon backbone shown with blue for DT catalytic domain, green for DT translocation domain, and white for IL-3. Model based on X-ray coordinates for DT and human IL-3. (Choe et al., "The crystal structure of diphtheria toxin," *Nature* 357:216-222 (1992).

FIG. 4. A photomicrograph of a bone marrow biopsy from a patient, prior to treatment (A) and two months post-treatment (B). Wright-Giemsa stained at 400× magnification.

FIG. 5. Graph showing percentage of patients with grade 2 or lower drug-related toxicities for $DT_{388}$IL-3 in connection with Example 2, infra.

FIG. 6A-B. Graph showing serum levels of $DT_{388}$IL-3 on Day 1 (A) and Day 12 (B) in connection with Example 2, infra.

FIGS. 7A-C. Pharmacokinetics and immune response in connection with Example 2, infra. FIG. 7A: Cmax (μg/ml) as a function of dose (μg/kg). FIG. 7B: Cmax on Day 12 versus Cmax on Day 1, showing relationship between Cmax on first and last dose. FIG. 7C: Peak Serum $DT_{388}$IL-3 (μg/ml) versus pretreatment serum anti-diphtheria toxin (anti-DT) antibody (μg/ml), showing relationship between peak drug and pretreatment antibody levels.

FIG. 8A: A photomicrograph of pre- and post-marrow aspirate from patient #19 in connection with Example 2, infra. FIG. 8B: Blood counts for patient #19 in connection with Example 2, infra. FIG. 8C: A photomicrograph of pre- and post-marrow aspirate from patient #36 in connection with Example 2, infra. FIG. 8D: Blood counts for patient #36 in connection with Example 2, infra.

5. DETAILED DESCRIPTION OF THE INVENTION

The present invention is directed to a method for inhibiting interleukin-3 receptor-expressing cells comprising administering to a human in need of such inhibition a pharmaceutical composition comprising an amount of a human interleukin-3-diphtheria toxin conjugate effective in inhibiting said cells and a pharmaceutically acceptable carrier, wherein the cells express the alpha subunit (in specific embodiments, the alpha and beta subunits) of the interleukin-3 receptor. Other methods include treating, preventing and/or managing a disease or disorder that displays or is characterized by interleukin-3 receptor-expressing cells by administering to a human in need of such treatment, prevention and/or management a pharmaceutical composition comprising an amount of a human interleukin-3-diphtheria toxin conjugate effective in inhibiting said cells and a pharmaceutically acceptable carrier, wherein the cells express the alpha subunit (in specific embodiments, the alpha and beta subunits) of the interleukin-3 receptor. Such diseases and disorders include, but are not limited to, cancer, autoimmune disease, inflammatory disease, and allergic disease. The present invention is also directed to methods for purging bone marrow or peripheral blood, by contacting ex vivo the bone marrow or peripheral blood sample obtained from a human with a composition comprising an amount of an interleukin-3-diphtheria toxin conjugate for a time sufficient to significantly purge the bone marrow or peripheral blood of cells expressing the alpha subunit (in specific embodiments, the alpha and beta subunits) of the interleukin-3 receptor. Accordingly, the present invention is also directed to a method for performing an autologous bone marrow transplant by administering back into the patient such purged bone marrow or peripheral blood, as well as compositions comprising such purged bone marrow or peripheral blood optionally with a pharmaceutically acceptable carrier.

5.1 Interleukin-3-Diphtheria Toxin Conjugate

In one embodiment, an interleukin-3-diphtheria toxin conjugate of the present invention comprises the full-length, mature (lacking the signal peptide) interleukin-3 protein (IL-3), or a portion, analog or derivative thereof that binds to the interleukin-3 receptor or a subunit thereof expressed on a cell surface, conjugated through a recombinant technology or through chemical (covalent) bond to diphtheria toxin, or a portion, analog or derivative thereof, which toxin preferably lacks the native cell binding domain. In a preferred embodiment, IL-3 is human IL-3. In certain embodiments, the conjugate comprises the catalytic and translocation domains of diphtheria toxin fused via a covalent bond to human IL-3. In other embodiments, the diphtheria toxin is linked via a peptide linker to the human IL-3 portion of the conjugate. The linker for the conjugate may be two, three, five, ten, or fifteen amino acids in length. The length of the linker may vary to provide optimal binding of the conjugate. In a preferred aspect, the peptide linker is two to four amino acids long. In a more specific aspect, the peptide linker is a Met-His linker. Although not intending to be bound by a particular mechanism of action, the flexible peptide linker facilitates chain pairing and minimizes possible refolding. Linker molecules are commonly known in the art and described in Denardo et al., 1998, *Clin. Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

In other embodiments, the invention provides pharmaceutical compositions comprising a conjugate of the invention and a pharmaceutically acceptable carrier. In accordance with the present invention, the conjugate can comprise any domain of DT linked via any linker molecule known in the art to any domain of IL-3. In a specific embodiment, the conjugate is $DT_{388}IL$-3 (FIG. 3), which is a fusion protein comprising amino acids 1-388 fused to full-length, mature, human IL-3 via a Met-His amino acid linker.

Diphtheria toxin (DT) is a 535 amino acid protein with three domains consisting of a catalytic domain (amino acids 1-186) connected by an arginine-rich disulfide loop to a translocation domain (amino acids 187-388) followed by a cell binding domain (amino acids 389-535; FIG. 1). See, e.g., Choe et al., "The crystal structure of diphtheria toxin," *Nature* 357:216-222 (1992). The amino acid sequence of DT can be found in the GenBank database (see, e.g., Accession No. AAN28949). Fragments, analogs and derivatives of diphtheria toxin can be useful in the present application. In some embodiments, the conjugate of the invention consists of the catalytic, the translocation and the cell binding domains of DT. In other embodiments, the conjugate consists of the cell binding and the catalytic domains of DT. In yet other embodiments, the conjugate of the invention consists of the cell binding and the translocation domains of DT. In preferred embodiments, the conjugate of the invention consists of the catalytic and translocation domains of DT. In some embodiments, the conjugate of the invention comprises one of either the translocation, catalytic, or cell binding domain.

Fragments, analogs, and derivatives of IL-3 can be useful in the present invention provided that when fused to the diphtheria toxin portion of the conjugate, such fragments, analogs and derivatives maintain the ability to bind a subunit of the IL-3 receptor or the native IL-3 receptor expressed on the surface of a cell. Preferably, the binding kinetics of the fragments, analogs or derivatives remain the same or vary only by not more than 25%. The IL-3 polypeptide may be from any species. The nucleotide and/or amino acid sequences of IL-3 polypeptides can be found in the literature or public databases, or the nucleotide and/or amino acid sequences can be determined using cloning and sequencing techniques known to one of skill in the art. In some embodiments, the IL-3 is a mammalian IL-3. In a preferred embodiment, an IL-3 polypeptide is human IL-3, an analog, derivative, or a fragment thereof. The amino acid sequence of human IL-3 can be found in the GenBank database (see, e.g., Accession No. AAC08706).

In one embodiment of the invention, an IL-3 polypeptide comprises an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions relative to the native IL-3 amino acid sequence (e.g., the native human IL-3 amino acid sequence), which result in a silent change, i.e., no change in activity. In another embodiment of the invention, an IL-3 polypeptide comprises an amino acid sequence which contains at least one conservative amino acid substitution; but not more than 10, 9, 8, 7, 6, 5, 4, 3, 2, or 1 conservative amino acid substitutions relative to the native IL-3 amino acid sequence (e.g., the native human IL-3 amino acid sequence), which result in a silent change. In yet another embodiment, an IL-3 polypeptide comprises an amino acid sequence which contains one or more conservative substitutions or a combination of non-conservative and conservative amino acid substitutions relative to the native IL-3 amino acid sequence, which results in a silent change.

To improve or alter the characteristics of IL-3 polypeptides, protein engineering may be employed. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity, potency, affinity, and/or increased stability. In addition, these may be purified in higher yields and show better solubility than the corresponding natural polypeptide, for example, under certain purification and storage conditions. For instance, for many proteins, it is known in the art that one or more amino acids may be deleted from the N-terminus or C-terminus without substantial loss of biological function. An exemplary conjugate comprising a modified IL-3 with amino acid substitution K116W in human IL-3. Another exemplary conjugate comprises human IL-3 missing amino acids 125-133. Both of these conjugates with mutant IL-3 sequences exhibit enhanced binding to the IL-3 receptor and exhibit greater cytotoxicity against leukemia cells. (For non-limiting examples of conjugates, see Liu et al. "Diphtheria toxin fused to variant interleukin-3 provides enhanced binding to the interleukin-3 receptor and more potent leukemia cell cytotoxicity," *Exp. Hematol.* 32:277-281 (2004); Hogge et al. "Variant diphtheria toxin-interleukin-3 fusion proteins with increased receptor affinity have enhanced cytotoxicity against acute myeloid leukemia progenitors," *Clin. Cancer Res.* 12:1284-1291 (2006); Testa et al. "Diphtheria toxin fused to variant human interleukin-3 induces cytotoxicity of blasts from patients with acute myeloid leukemia according to the level of interleukin-3 receptor expression," *Blood* 106:2527-2529 (2005); and Klein et al. "Receptor binding kinetics of human IL-3 variants with altered proliferative activity," *Biochem. Biophys. Res. Comm.* 288:1244-1249 (2001)).

In another embodiment, an IL-3 polypeptide is at least 50%, at least 65%, at least 70%, at least 75%, at least 80%, at least 85%, at least 90%, or at least 95% identical to a native IL-3 amino acid sequence (e.g., a native human IL-3 amino acid sequence).

5.1.1 Methods for Producing Interleukin-3-Diphtheria Toxin Conjugates

The conjugates of the present invention can be made by standard recombinant DNA techniques or by protein synthetic techniques, e.g., by use of a peptide synthesizer. For example, a nucleic acid molecule encoding a conjugate of the invention can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992).

The nucleotide sequences encoding a conjugate of the invention (IL-3 and diphtheria toxin sequences) may be obtained from any information available to those of skill in the art (i.e., from Genbank, the literature, or by routine cloning). The nucleotide sequence coding for a conjugate can be inserted into an appropriate expression vector, i.e., a vector which contains the necessary elements for the transcription and translation of the inserted protein-coding sequence. In some instances, the diphtheria toxin sequence can be truncated in order to remove a specific domain, such as the targeting domain. The techniques for modifying or truncating DNA are well known to those of skill in the art of molecular biology. Also, the IL-3 and the diphtheria toxin sequences can be ligated in such a way as to generate a DNA sequence that, when translating, creates a polypeptide that is a compound of the invention. In preferred examples, a linker sequence is introduced into the recombinant sequence that links the IL-3 sequence and the diphtheria toxin sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast (e.g. *Pichia*) containing yeast vectors; or bacteria (such as *E. coli*) transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the protein is expressed in *E. coli*. In another specific embodiment, the protein is expressed in *Pichia*.

The expression of a conjugate of the invention may be controlled by any promoter or enhancer element known in the art. Promoters which may be used to control expression of a conjugate include, but are not limited to, the SV40 early promoter region (Bernoist and Chambon, 1981, *Nature* 290:304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42), the tetracycline (Tet) promoter (Gossen et al., 1995, *Proc. Nat. Acad. Sci. U.S.A.* 89:5547-5551); prokaryotic expression vectors such as the β-lactamase promoter (VIIIa-Kamaroff, et al., 1978, *Proc. Natl. Acad. Sci. USA.* 75:3727-3731), or the tac promoter (DeBoer, et al., 1983, *Proc. Natl. Acad. Sci. USA.* 80:21-25; see also "Useful proteins from recombinant bacteria," in *Scientific American*, 1980, 242:74-94); plant expression vectors comprising the nopaline synthetase promoter region (Herrera-Estrella et al., *Nature* 303:209-213) or the cauliflower mosaic virus 35S RNA promoter (Gardner, et al., 1981, *Nucl. Acids Res.* 9:2871), and the promoter of the photosynthetic enzyme ribulose biphosphate carboxylase (Herrera-Estrella et al., 1984, *Nature* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, *Nature* 315:115-122), immunoglobulin gene control region which is active in lymphoid cells (Grosschedl et al., 1984, Cell 38:647-658; Adames et al., 1985, *Nature* 318:533-538; Alexander et al., 1987, *Mol. Cell. Biol.* 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.* 5:1639-1648; Hammer et al., 1987, *Science* 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94;

myelin basic protein gene control region which is active in oligodendrocyte cells in the brain (Readhead et al., 1987, *Cell* 48:703-712); myosin light chain-2 gene control region which is active in skeletal muscle (Sani, 1985, *Nature* 314:283-286); neuronal-specific enolase (NSE) which is active in neuronal cells (Morelli et al., 1999, *Gen. Virol.* 80:571-83); brain-derived neurotrophic factor (BDNF) gene control region which is active in neuronal cells (Tabuchi et al., 1998, *Biochem. Biophysic. Res. Com.* 253:818-823); glial fibrillary acidic protein (GFAP) promoter which is active in astrocytes (Gomes et al., 1999, *Braz. J. Med. Biol. Res.* 32(5):619-631; Morelli et al., 1999, *Gen. Virol.* 80:571-83) and gonadotropic releasing hormone gene control region which is active in the hypothalamus (Mason et al., 1986, *Science* 234:1372-1378). In a specific embodiment, the expression of a conjugate of the invention is regulated by a constitutive promoter. In another embodiment, the expression is regulated by an inducible promoter. In another embodiment, the expression is regulated by a tissue-specific promoter.

In a specific embodiment, a vector is used that comprises a promoter operably linked to a conjugate-encoding nucleic acid, one or more origins of replication and, optionally, one or more selectable markers (e.g., an antibiotic resistance gene).

In mammalian host cells, a number of viral-based expression systems may be utilized. In cases where an adenovirus is used as an expression vector, the polypeptide or fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

Expression vectors containing inserts of a gene encoding a conjugate can be identified by three general approaches: (a) nucleic acid hybridization, (b) presence or absence of "marker" gene functions, and (c) expression of inserted sequences. In the first approach, the presence of a gene encoding a conjugate in an expression vector can be detected by nucleic acid hybridization using probes comprising sequences that are homologous to an inserted gene encoding the conjugate. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a conjugate in the vector. For example, if the nucleotide sequence encoding the conjugate is inserted within the marker gene sequence of the vector, recombinants containing the gene encoding the conjugate insert can be identified by the absence of the marker gene function. In the third approach, recombinant expression vectors can be identified by assaying the gene product (e.g., conjugate) expressed by the recombinant. Such assays can be based, for example, on the physical or functional properties of the conjugate in in vitro assay systems, e.g., binding to an antibody or the IL-3 receptor.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion proteins or conjugates may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERY, BHK, HeLa, COS, MDCK, 293, 3T3, W138, NSO, and in particular, neuronal cell lines such as, for example, SK-N-AS, SK-N-FI, SK-N-DZ human neuroblastomas (Sugimoto et al., 1984, *J. Natl. Cancer Inst.* 73: 51-57), SK-N-SH human neuroblastoma (*Biochim. Biophys. Acta*, 1982, 704: 450-460), Daoy human cerebellar medulloblastoma (He et al., 1992, *Cancer Res.* 52: 1144-1148) DBTRG-05MG glioblastoma cells (Kruse et al., 1992, In *Vitro Cell. Dev. Biol.* 28A: 609-614), IMR-32 human neuroblastoma (*Cancer Res.*, 1970, 30: 2110-2118), 1321N1 human astrocytoma (*Proc. Natl. Acad. Sci. U.S.A.* 1977, 74: 4816), MOG-G-CCM human astrocytoma (*Br. J. Cancer* 1984, 49: 269), U87MG human glioblastoma-astrocytoma (*Acta Pathol. Microbiol. Scand.* 1968, 74: 465-486), A172 human glioblastoma (Olopade et al., 1992, *Cancer Res.* 52: 2523-2529), C6 rat glioma cells (Benda et al., 1968, *Science* 161: 370-371), Neuro-2a mouse neuroblastoma (*Proc. Natl. Acad. Sci. U.S.A.* 1970, 65: 129-136), NB41A3 mouse neuroblastoma (*Proc. Natl. Acad. Sci. U.S.A.* 1962, 48: 1184-1190), SCP sheep choroid plexus (Bolin et al., 1994, *J. Virol. Methods* 48: 211-221), G355-5, PG-4 Cat normal astrocyte (Haapala et al., 1985, *J. Virol.* 53: 827-833), Mpf ferret brain (Trowbridge et al., 1982, *In Vitro* 18: 952-960), and normal cell lines such as, for example, CTX TNA2 rat normal cortex brain (Radany et al., 1992, *Proc. Natl. Acad. Sci. U.S.A.* 89: 6467-6471) such as, for example, CRL7030 and Hs578Bst. Furthermore, different vector/host expression systems may effect processing reactions to different extents.

For long-term, high-yield production of recombinant conjugates, stable expression is preferred. For example, cell lines which stably express the conjugate of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a conjugate of the invention.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. U.S.A.* 48:2026), and adenine phosphoribosyltransferase (Lowy, et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler, et al., 1980, *Proc. Natl. Acad. Sci. U.S.A.* 77:3567; O'Hare, et al., 1981, *Proc. Natl. Acad. Sci. U.S.A.* 78:1527); gpt, which confers resistance to mycophenolic acid (Mulligan & Berg, 1981, *Proc. Natl. Acad. Sci. U.S.A.* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Once a conjugate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.2 Pharmaceutical Compositions and Routes of Administration

The present invention provides compositions comprising a diphtheria toxin-interleukin-3 conjugate of the invention. In particular, the invention provides a pharmaceutical composition comprising an effective amount of a conjugate of the invention and a pharmaceutically acceptable carrier or vehicle. In a specific embodiment, a pharmaceutical composition comprises an effective amount of a conjugate of the invention and a pharmaceutically acceptable carrier or vehicle. The pharmaceutical compositions are suitable for veterinary and/or human administration. The pharmaceutical compositions are also suitable for ex vivo purging of a bone marrow or peripheral blood sample, e.g. as may be practiced prior to re-introduction of the purged sample as an autologous transplant back into the patient as may be practiced following high dose chemotherapy for cancer.

The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The compositions of the invention can be in the form of a solid, liquid, or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow a compound of the invention to be bioavailable upon administration of the composition to a subject. Compositions can take the form of one or more dosage units, where, for example, a tablet can be a single dosage unit, and a container of a compound of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the compound of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the compounds of the invention and pharmaceutically acceptable carriers are sterile. Water is a preferred carrier when the compound of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension, and gel forms are included within the forms considered herein as either solid or liquid.

As a solid composition for oral administration, the composition can be formulated into a powder, granule, compressed tablet, pill, capsule, chewing gum, wafer, or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin, or a fatty oil.

The pharmaceutical composition can be in the form of a liquid, e.g., an elixir, syrup, solution, emulsion, or suspension. The liquid can be useful for oral administration or for delivery by injection. When intended for oral administration, a composition can comprise one or more of a sweetening agent, preservatives, dye/colorant, and flavor enhancer. In a composition for administration by injection, one or more of a surfactant, preservative, wetting agent, dispersing agent, suspending agent, buffer, stabilizer, and isotonic agent can also be included.

The liquid compositions of the invention, whether they are solutions, suspensions, or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol, or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. A parenteral composition can be enclosed in an ampoule, a disposable syringe, or a multiple-dose vial made of glass, plastic or other material. Physiological saline is a preferred adjuvant. An injectable composition is preferably sterile.

The pharmaceutical compositions comprise an effective amount of a conjugate of the invention such that a suitable dosage will be obtained (see Section 5.3.1, infra, for suitable dosages). Typically, this amount is at least 0.01% of a conjugate of the invention by weight of the composition. When intended for oral administration, this amount can be varied to be between 0.1% and 80% by weight of the composition. Preferred oral compositions can comprise from between 4% and 50% of the compound of the invention by weight of the composition. Preferred compositions of the present invention are prepared so that a parenteral dosage unit contains from between 0.01% and 2% by weight of the compound of the invention.

The compositions of the invention can be administered by any convenient route, for example, by infusion or bolus injection, by absorption through epithelial or mucocutaneous linings (e.g., oral mucosa, rectal, and intestinal mucosa, etc.). Administration can be systemic or local. Various delivery systems are known, e.g., microparticles, microcapsules, capsules, etc., and may be useful for administering a compound of the invention. In certain embodiments, more than one compound of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend, in-part, upon the site of the medical condition (such as the site of cancer, a cancerous tumor, or a pre-cancerous condition).

In one embodiment, the compounds of the invention are administered parenterally. In a specific embodiment, the compounds of the invention are administered intravenously. In another embodiment, the compounds of the invention are administered by continuous infusion. In a particular embodiment, the compounds of the invention are administered by an infusion that lasts for about 15 minutes, about 20 minutes, about 30 minutes, about 45 minutes, about 1 hour, or about 2 hours.

In specific embodiments, it can be desirable to administer one or more compounds of the invention locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor, or precancerous tissue. In certain embodiments, it can be desirable to introduce one or more compounds of the invention into the central nervous system by any suitable route, including intraventricular and intrathecal injection. Intraventricular injection can be facilitated by an intraventricular catheter, for example, attached to a reservoir, such as an Ommaya reservoir. In certain embodiments, one or more compounds of the invention can be injected intraperitoneally.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and carriers such as triglycerides.

In yet another embodiment, the compounds of the invention can be delivered in a controlled release system. In one embodiment, a pump can be used (see Sefton, *CRC Crit. Ref Biomed. Eng.* 1987, 14, 201; Buchwald et al., *Surgery* 1980, 88: 507; Saudek et al., *N. Engl. J. Med.* 1989, 321: 574). In another embodiment, polymeric materials can be used (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.* 1989, 25, 351; Howard et al., *J. Neurosurg.*, 1989, 71, 105). In yet another embodiment, a controlled-release system can be placed in proximity of the target of the compounds of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can also be used.

In another embodiment, polymeric materials can be used to achieve controlled or sustained release of the compounds of the invention (see, e.g., U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

In a specific embodiment, a pump can be used to deliver the compounds of the invention (see, e.g, Sefton, *CRC Crit. Ref Biomed Eng.* 1987, 14, 201; Buchwald et al., *Surgery* 1980, 88: 507; Saudek et al., *N. Engl. J. Med.* 1989, 321: 574). In a specific embodiment, the pump may be, but is not limited to, an insulin-like pump.

The present compositions can take the form of solutions, suspensions, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in *Remington's Pharmaceutical Sciences* by E. W. Martin.

Sustained or directed release compositions that can be formulated include, but are not limited to, compounds of the invention protected with differentially degradable coatings, e.g., by microencapsulation, multiple coatings, etc. It is also possible to freeze-dry the compositions and use the lyophilizates obtained, for example, for the preparation of products for injection.

In a preferred embodiment, the conjugates of the invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a conjugate of the invention is to be administered by infusion, it can be dispensed, for example, with an infusion bottle containing sterile pharmaceutical grade water or saline. Where the conjugate of the invention is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving complex are also suitable for orally administered compositions of the invention. In these later platforms, fluid from the environment surrounding the capsule is imbibed by the driving complex, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers such as mannitol, lactose, starch, magnesium stearate, sodium saccharine, cellulose, magnesium carbonate, etc. Such carriers are preferably of pharmaceutical grade.

The pharmaceutical compositions of the invention can be intended for topical administration, in which case the carrier can be in the form of a solution, emulsion, ointment, or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device. Topical formulations can comprise a concentration of a compound of the invention of from between 0.01% and 10% w/v (weight per unit volume of composition).

The compositions can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of the compositions can be delivered in single phase, bi-phasic, or tri-phasic systems in order to deliver the composition. Delivery of the aerosol includes the necessary container, activators, valves, subcontainers, spacers and the like, which together can form a kit. Preferred aerosols can be determined by one skilled in the art, without undue experimentation.

Whether in solid, liquid, or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a compound of the invention, an additional agent, and a pharmaceutically acceptable acceptable carrier or vehicle.

The pharmaceutical compositions can be prepared using methodology well known in the pharmaceutical art. For example, a composition intended to be administered by injection can be prepared by combining a compound of the invention with water so as to form a solution. A surfactant can be added to facilitate the formation of a homogeneous solution or suspension. Surfactants are complexes that can non-covalently interact with a compound of the invention so as to facilitate dissolution or homogeneous suspension of the compound of the invention in the aqueous delivery system.

In one embodiment, the pharmaceutical compositions of the present invention may comprise one or more known therapeutically active agents.

5.3 Therapeutic and Prophylatic Uses of Interleukin-3-Diphtheria Toxin Fusion Conjugates The present invention provides methods for inhibiting IL-3 receptor expressing cells in a human in need thereof by administering an effective amount of a human IL-3-diphtheria toxin conjugate of the invention. In certain embodiments, the IL-3 receptor expressing cells are not myeloid leukemia cells. In some embodiments, the cells express the alpha subunit of the interleukin-3 receptor. In other embodiments, the cells express the beta subunit of the interleukin-3 receptor. In yet other embodiments, the cells express both the alpha and beta subunits of the IL-3 receptor.

The present invention is directed to therapies which involve administering one of more the interleukin-3-diphtheria toxin conjugates of the invention and compositions comprising the interleukin-3-diphtheria toxin conjugates to a subject, preferably a human subject, for preventing, treating, managing, and/or ameliorating disease or disorder that displays or is characterized by interleukin-3 receptor expression or one or more symptoms thereof. In one embodiment, the invention provides a method of preventing, treating, managing, and/or ameliorating a disease or disorder that displays or is characterized by interleukin-3 receptor expression or one or more symptoms thereof, said method comprising administering to a subject in need thereof an effective amount of one or more the interleukin-3-diphtheria toxin conjugates of the invention. Such diseases and disorders include cancer, allergic diseases, inflammatory diseases, and autoimmune diseases.

The invention also provides methods comprising administering to a subject in need thereof an interleukin-3-diphtheria toxin conjugate of the invention and one or more therapies (e.g., one or more prophylactic or therapeutic agents) other than the interleukin-3-diphtheria toxin conjugate of the invention that are currently being used, have been used, are known to be useful, or may be useful in the prevention, treatment, management, and/or amelioration of a disease or disorder that displays or is characterized by interleukin-3 receptor expression or one or more symptoms thereof. The prophylactic or therapeutic agents of the combination therapies of the invention can be administered sequentially or concurrently. In a specific embodiment, the combination therapies of the invention comprise an effective amount of a conjugate of the invention and an effective amount of at least one other therapy which has the same mechanism of action as said conjugate. In a specific embodiment, the combination therapies of the invention comprise an effective amount of a conjugate of the invention and an effective amount of at least one other therapy (e.g., prophylactic or therapeutic agent) which has a different mechanism of action than said conjugate. In certain embodiments, the combination therapies of the present invention improve the prophylactic or therapeutic effect of a conjugate of the invention by functioning together with the conjugate to have an additive or synergistic effect. In certain embodiments, the combination therapies of the present invention reduce the side effects associated with the prophylactic or therapeutic agents. In other embodiments, the combination therapies are administered prior to, during, or after the administration of the compositions of the invention.

Cancer or a neoplastic disease, including, but not limited to, neoplasms, tumors, metastases, or any disease or disorder characterized by uncontrolled cell growth, can be treated, suppressed, delayed, managed, inhibited or prevented by administering to a subject in need thereof a prophylactically effective regimen or a therapeutically effective regimen, the regimen comprising administering to the patient a compound of the invention. In specific embodiments, the invention encompasses the treatment, suppression, delaying, management, inhibiting of growth and/or progression, and prevention of cancer or neoplastic disease as described herein.

In one embodiment, the conjugates of the invention are administered as monotherapy for the prevention, treatment, and/or management of cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a conjugate of the invention or a pharmaceutical composition of the invention, wherein the patient has been diagnosed with cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a conjugate of the invention or a pharmaceutical composition of the invention, wherein the patient has relapsed from cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a conjugate of the invention or a pharmaceutical composition of the invention, wherein the patient has failed or is failing therapy.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a conjugate of the invention or a pharmaceutical composition of the invention, wherein the patient is in remission from cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a conjugate of the invention or a pharmaceutical composition of the invention, wherein the patient is refractory to therapy.

In one embodiment, the cancer is a hematologic cancer. For instance, the cancer can be leukemia, lymphoma, myelodysplastic syndrome (MDS), or myeloma. In another embodiment, the cancer is a solid tumor.

In one embodiment of this aspect, the patient has received or is receiving another therapy. In another embodiment of this aspect, the patient has not previously received a therapy for the prevention, treatment, and/or management of the cancer.

The medical practitioner can diagnose the patient using any of the conventional cancer screening methods including, but not limited to physical examination (e.g., prostate examination, rectal examination, breast examination, lymph nodes examination, abdominal examination, skin surveillance, testicular exam, general palpation), visual methods (e.g., colonoscopy, bronchoscopy, endoscopy), PAP smear analyses (cervical cancer), stool guaiac analyses, blood tests (e.g., complete blood count (CBC) test, prostate specific antigen (PSA) test, carcinoembryonic antigen (CEA) test, cancer antigen (CA)-125 test, alpha-fetoprotein (AFP), liver function tests), karyotyping analyses, bone marrow analyses (e.g., in cases of hematological malignancies), histology, cytology, flow cytometry, a sputum analysis, and imaging methods (e.g., computed tomography (CT), magnetic resonance imaging (MRI), ultrasound, X-ray imaging, mammography, PET scans, bone scans, radionuclide scans).

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient a conjugate or pharmaceutical composition of the invention wherein the patient has been diagnosed with a solid tumor, and wherein the patient has undergone a primary therapy to reduce the bulk of the tumor. The primary therapy to reduce the tumor bulk size is preferably a therapy other than a conjugate of the invention. In specific embodiment of this aspect, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, or retinoblastoma.

Another aspect of the invention relates to a method of preventing, treating, and/or managing cancer, the method comprising administering to a patient in need thereof a prophylactically effective regimen or a therapeutically effective regimen, the regimen comprising administering to the patient a conjugate of the invention, wherein the patient received another therapy. In some embodiments, the prior therapy is, for example, chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or any combination thereof.

In some embodiments, the prior therapy has failed in the patient. In some embodiments, the therapeutically effective regimen comprising administration of a conjugate of the invention is administered to the patient immediately after the patient has undergone the prior therapy. For instance, in certain embodiments, the outcome of the prior therapy may be unknown before the patient is administered the conjugate.

Another aspect of the invention relates to a method of preventing cancer in a patient (e.g., a human patient), the method comprising administering to a patient in need thereof a prophylactically effective regimen or a therapeutically effective regimen, the regimen comprising administering to the patient a conjugate of the invention, wherein the cancer in the patient has entered remission. In some embodiments of this aspect, through administration of a prophylactically effective regimen or a therapeutically effective regimen, the medical practitioner can effectively cure the cancer, or prevent its reoccurrence.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient a compound or composition of the invention, wherein the conjugate is administered at a dose that is lower than the maximum tolerated dose (MTD) over a period of three months, four months, six months, nine months, 1 year, 2 years, 3 years, 4 years, or more.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient a conjugate of the invention, wherein the conjugate is administered at a dose that is lower than the human equivalent dosage (HED) of the no observed adverse effect level (NOAEL) over a period of three months, four months, six months, nine months, 1 year, 2 years, 3 years, 4 years, or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., $mg/m^2$). In specific embodiments, the NOAELs are determined in mice, hamsters, rats, ferrets, guinea pigs, rabbits, dogs, primates (monkeys, marmosets, squirrel monkeys, baboons), micropigs, or minipigs. For a discussion on the use of NOAELs and their extrapolation to determine human equivalent doses, see *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005.

While not being bound by any specific theory, Applicants believe that by the administration of the prophylactically and/or therapeutically effective regimens, the cancer stem cell population of a cancer/tumor is stabilized or reduced, so as to limit or prevent the potential repopulation of the tumor.

In certain embodiments of these aspects, the regimens comprise administering a prophylactically effective regimen and/or a therapeutically effective regimen, wherein the regimen results in a reduction in the cancer stem cell population in the patient. In one embodiment, the patient undergoing the regimen is monitored to determine whether the regimen has resulted in a reduction in the cancer stem cell population in the patient.

Typically, the monitoring of the amount of cancer stem cells is conducted by detecting the amount of cancer stem cells in a specimen extracted from the patient. Methods of detecting the amount of cancer stem cells in a specimen are described infra in Section 5.4. This monitoring step is typically performed at least 1, 2, 4, 6, 7, 8, 10, 12, 14, 15, 16, 18, 20, or 30, 60, 90, 120 days, 6 months, 9 months, 12 months, or >12 months after the patient begins receiving the regimen.

In some embodiments, the specimen may be a blood specimen, wherein the amount of cancer stem cells per unit of volume (e.g., 1 ml) or other measured unit (e.g., per unit field in the case of a histological analysis) is quantitated. In certain embodiments, the amount of cancer stem cells is determined as a portion (e.g., a percentage) of the cancer cells present in the blood specimen, as a subset of the cancer cells present in the blood specimen, or as a subset of a subset of the cancer cells present in the blood specimen. The amount of cancer stem cells, in other embodiments, can be determined as a percentage of the total blood cells.

In other embodiments, the specimen extracted from the patient is a tissue specimen (e.g., a biopsy extracted from suspected cancerous tissue), where the amount of cancer stem cells can be measured, for example, on the basis of the amount of cancer stem cells per unit weight of the tissue. In certain embodiments, the amount of cancer stem cells is determined as a portion (e.g., a percentage) of the cancer cells present in the tissue, as a subset of the cancer cells present in the tissue, or as a subset of a subset of the cancer cells present in the tissue.

The amount of cancer stem cells in the extracted specimen can be compared with the amount of cancer stem cells measured in reference samples to assess the efficacy of the regimen, and the amelioration of the cancer under therapy. In one embodiment, the reference sample is a specimen extracted from the patient undergoing therapy, wherein the specimen is extracted from the patient at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the amount of cancer stem cells in the extracted specimen can be compared with a predetermined reference range. In a specific embodiment, the predetermined reference range is based on i) the amount of cancer stem cells obtained from a population(s) of patients suffering from the same type of cancer as the patient undergoing the therapy, or ii) the amount of stem cells obtained from a population(s) of patients without cancer.

If the reduction in the amount of cancer stem cells is determined to be too small upon comparing the amount of cancer stem cells in the specimen extracted from the patient undergoing the regimen with the reference specimen, then the medical practitioner has a number of options to adjust the regimen. For instance, the medical practitioner can then increase either the dosage of the compound or composition of the invention administered, the frequency of the administration, the duration of administration, or any combination thereof. In a specific embodiment, after the determination is made, a second effective amount of a compound or composition of the invention can be administered to the patient.

In certain embodiments, if the reduction in the amount of cancer stem cells is determined to be acceptable upon comparing the amount of cancer stem cells in the sample obtained from the patient undergoing the therapeutic or prophylactic regimen with the reference sample, then the medical practitioner may elect not to adjust the regimen. For instance, the medical practitioner may elect not to increase either the dosage of the compound or composition of the invention being administered, the frequency of the administration, the duration of administration, or any combination thereof. Further, the medical practitioner may elect to add additional therapies or combine therapies.

In other embodiments, the regimens comprise administering a prophylactically effective regimen and/or a therapeutically effective regimen, wherein the regimen results in a reduction in the amount of cancer cells in the patient. In one embodiment, the patient undergoing the regimen is monitored to determine whether the regimen has resulted in a reduction in the amount of cancer cells in the patient.

Typically, the monitoring of the amount of cancer cells is conducted by detecting the amount of cancer cells in a specimen extracted from the patient. Methods of detecting the amount of cancer cells in a specimen are described infra in Section 5.5. This monitoring step is typically performed at least 1, 2, 4, 6, 7, 8, 10, 12, 14, 15, 16, 18, 20, or 30, 60, 90, 120 days, 6 months, 9 months, 12 months, or >12 months after the patient begins receiving the regimen.

In some embodiments, the specimen may be a blood specimen, wherein the amount of cancer cells per unit of volume (e.g., 1 ml) or other measured unit (e.g., per unit field in the case of a histological analysis) is quantitated. The cancer cell population, in certain embodiments, can be determined as a percentage of the total blood cells.

In some embodiments, the sample obtained from the patient may be a bone marrow specimen, wherein the amount of cancer cells per unit of volume (e.g., 1 ml) or other measured unit (e.g., per unit field in the case of a histological analysis) is quantitated. The cancer cell population, in certain embodiments, can be determined as a percentage of the total bone marrow cells.

In other embodiments, the specimen extracted from the patient is a tissue specimen (e.g., a biopsy extracted from suspected cancerous tissue), where the amount of cancer cells can be measured, for example, on the basis of the amount of cancer cells per unit weight of the tissue. The amount of cancer cells can also be measured using immunohistochemistry or flow cytometry.

The amount of cancer cells in the extracted specimen can be compared with the amount of cancer cells measured in reference samples to assess the efficacy of the regimen and amelioration of the cancer under therapy. In one embodiment, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the cancer cell population in the extracted specimen can be compared with a predetermined reference range. In a specific embodiment, the predetermined reference range is based on the amount of cancer cells obtained from a population(s) of patients suffering from the same type of cancer as the patient undergoing the therapy.

If the reduction in the cancer cell population is judged too small upon comparing the amount of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

If the reduction in the cancer cell population is judged to be adequate upon comparing the amount of cancer cells in the specimen extracted from the patients undergoing therapy with the reference specimen, then the medical practitioner may elect not to adjust the therapeutic regimen. For instance, the medical practitioner may elect not to increase the dosage of the compound or composition of the invention administered, the frequency of the administration, the duration of administration, or any combination thereof.

The above monitoring methods can also be used to monitor the amount of interleukin-3 receptor-expressing cells where the disease or disorder is not a cancer, i.e., in allergic disease or autoimmune disease.

In embodiments, the medical practitioner may elect to measure the cancer population using in vivo imaging techniques. For example, a ligand for a tumor marker can be conjugated to a radioisotope, photon emitting compound, or other signal emitting compound, and then the ligand can be injected into the patient. The cancer cells can then be quantitated by measuring the signal generated when the ligand binds to the cancer cells in vivo.

5.3.1 Dosage and Frequency of Administration

The amount of a diphtheria toxin-interleukin-3 pharmaceutical composition of the invention used in the prophylactic and/or therapeutic regimens which will be effective in the prevention, treatment, and/or management of diseases or disorders characterized by cells expressing the interleukin-3 receptor beta subunit, including cancer, can be determined by methods disclosed herein. The frequency and dosage will vary according to factors specific for each patient depending on the specific conjugates administered, the severity of the (e.g. cancerous) condition, the route of administration, as well as age, body, weight, response, and the past medical history of the patient. For example, the dosage of a conjugate of the invention which will be effective in the treatment, prevention, and/or management of cancer can be determined by administering the compound in an animal model such as, e.g., the animal models disclosed herein or known in to those skilled in the art. See Section 5.7.2, infra. In addition, in vitro assays may optionally be employed to help identify optimal dosage ranges. See Section 5.7.1, infra.

In some embodiments, the prophylactic and/or therapeutic regimens comprise titrating the dosages administered to the patient so as to achieve a specified measure of therapeutic efficacy. Such measures include a reduction in the amount of cancer stem cells in or from the patient and/or a reduction in the amount of cancer cells in or from the patient.

In some embodiments, the prophylactic and/or therapeutic regimens comprise administering dosages and regimens of a conjugate or pharmaceutical composition of the invention that are effective to reduce cancer stem cells. Methods that can be used to determine the amount of cancer stem cells in a patient prior to, during, and/or following therapy are discussed infra in Section 5.4.

In certain embodiments, the dosage of the conjugate of the invention in the prophylactic and/or therapeutic regimen is adjusted so as to achieve a reduction in the amount of cancer stem cells found in a test specimen extracted from a patient after undergoing the therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic or therapeutic regimen. In specific embodiments, the amount of cancer stem cells in the test specimen is at least 2%, 5%, 10%, 15%, 20%, 30%, 40%, 50%, 60%, 70%, 80%, 90%, 95%, or 99% lower than in the reference sample.

In other embodiments, the dosage of the conjugate of the invention in the prophylactic and/or therapeutic regimen is adjusted so as to achieve a reduction in the amount of cancer stem cells found in a test specimen extracted from a patient after undergoing the prophylactic and/or therapeutic regimen, as compared with a reference sample, wherein the reference sample specimen is extracted from a healthy, noncancer-afflicted patient. In specific embodiments, the amount of cancer stem cells in the test specimen is at least within 60%, 50%, 40%, 30%, 20%, 15%, 10%, 5%, or 2% of the amount of cancer stem cells in the reference sample.

In some embodiments, the dosage of the conjugate of the invention in the prophylactic and/or therapeutic regimen is adjusted so as to achieve an amount of cancer stem cells that falls within a predetermined reference range. In these embodiments, the amount of cancer stem cells in a test specimen is compared with a predetermined reference range. In a specific embodiment, the predetermined reference range is based on the amount of cancer stem cells obtained from a population(s) of patients suffering from the same type of cancer as the patient undergoing the therapy.

In some embodiments, the prophylactic and/or therapeutic regimens comprise administering dosages of a conjugate or pharmaceutical composition of the invention that are effective to reduce the cancer cell population. Methods that can be used to determine the cancer cell population in a patient undergoing treatment are discussed infra in Section 5.5.

In certain embodiments, the dosage of the conjugate of the invention in the prophylactic and/or therapeutic regimen is adjusted so as to achieve a reduction in the amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic and/or therapeutic regimen. In specific embodiments, the amount of cancer cells in the test specimen is at least 2%, 5%, 10%, 15%, 20%, 30%, 40%, 50%, or 60% lower than in the reference sample.

In some embodiments, the dosage of the conjugate of the invention in the prophylactic and/or therapeutic regimen is adjusted so as to achieve an amount of cancer cells that falls within a predetermined reference range. In these embodiments, the amount of cancer cells in a test specimen is compared with a predetermined reference range.

In other embodiments, the dosage of the conjugate of the invention in prophylactic and/or therapeutic regimen is adjusted so as to achieve a reduction in the amount of cancer cells found in a test specimen extracted from a patient after undergoing the prophylactic and/or therapeutic regimen, as compared with a reference sample, wherein the reference sample is a specimen extracted from a healthy, noncancer-afflicted patient. In specific embodiments, the amount of cancer cells in the test specimen is at least within 60%, 50%, 40%, 30%, 20%, 15%, 10%, 5%, or 2% of the amount of cancer cells in the reference sample.

In treating certain human patients having solid tumors, extracting multiple tissue specimens from a suspected tumor site may or may not prove impracticable. In these embodiments, the dosage of the compounds of the invention in the prophylactic and/or therapeutic regimen for a human patient is extrapolated from doses in animal models that are effective to reduce the amount of cancer stem cells in those animal models. In the animal models, the prophylactic and/or therapeutic regimens are adjusted so as to achieve a reduction in the amount of cancer stem cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the amount of cancer stem cells in the test specimen is at least 2%, 5%, 10%, 15%, 20%, 30%, 40%, 50%, or 60% lower than in the reference sample. The doses effective in reducing the amount of cancer stem cells in the animals can be normalized to body surface are (mg/m$^2$) to provide an equivalent human dose.

The prophylactic and/or therapeutic regimens disclosed herein comprise administration of a conjugate of the invention or pharmaceutical compositions thereof to the patient in a single dose or in multiple doses (e.g., 1, 2, 3, 4, 5, 6, 7, 8, 10, 15, 20, or more doses).

In one embodiment, the prophylactic and/or therapeutic regimens comprise administration of a conjugate of the invention or pharmaceutical compositions thereof in multiple doses. When administered in multiple doses, the conjugate or pharmaceutical compositions are administered with a frequency and in an amount sufficient to prevent, treat, and/or manage the condition. In one embodiment, the frequency of administration ranges from once a day up to about once every eight weeks. In another embodiment, the frequency of administration ranges from about once a week up to about once every six weeks. In another embodiment, the frequency of administration ranges from about once every three weeks up to about once every four weeks. In certain embodiments, the conjugate is administered over a period of one week to two years. In yet another embodiment, the conjugate is administered over a period of two weeks or greater. In other embodiments, the conjugate is administered over a period of two weeks to one year. In further embodiments, the conjugate is administered over a period of two weeks to six months. In some embodiments, the conjugate is administered over a period of two weeks to twelve weeks. In yet other embodiments, the conjugate is administered over a period of two weeks to six weeks. In certain embodiments, the conjugate is administered once a week, twice a week, three times a week, four times a week, five times a week, six times a week, or seven times a week. In preferred embodiments, the conjugate is administered at least three times a week. In other preferred embodiments, the compound is administered daily for five consecutive days, or daily for seven consecutive days. In other embodiments, the conjugate is administered once a day, twice a day, three times a day, four times a day, or five times a day. In preferred embodiments, the conjugate is administered three times a week over a period of two weeks. In some embodiments, each time the conjugate is administered, it is administered at a dose of 4 µg/kg per day or greater. In some embodiments, the compound is administered for one, two, three, four, five, six, seven, eight, nine, ten, eleven, twelve, thirteen, fourteen, or fifteen cycles.

In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. In a specific aspect, the conjugate can be administered at or below a dose that is the maximum dose tolerated without undue toxicity. In specific embodiments, where the disease or disorder is myeloid leukemia, the dosage given is in a range of between greater than 4 µg/kg per day to about 20 µg/kg per day. The per day dosages described herein may be administered on consecutive and/or non-consecutive days. In a specific embodiment, a per day dosage is administered on non-consecutive days throughout a week, e.g., Monday, Wednesday, and Friday. In another specific embodiment, a per day dosage is administered on consecutive days throughout a week, e.g. Monday, Tuesday, Wednesday, Thursday, and Friday.

In specific aspects of this embodiment, the conjugate can be administered at a dose of 4 µg/kg per day or greater. In other aspects, the conjugate can be administered at a dose in a range of about 4 µg/kg per day to about 20 µg/kg per day. In yet other aspects, the conjugate can be administered at a dose in a range of about 4 µg/kg per day to about 9 µg/kg per day. In yet other aspects, the conjugate can be administered at a dose in a range of about 4 µg/kg per day to about 12.5 µg/kg per day. In a specific aspect of this embodiment, the conjugate can be administered at a dose of about 5.3 µg/kg per day, or at a dose of about 7.1 µg/kg per day, or at a dose of about 9.4 µg/kg per day, or at a dose of about 12.5 µg/kg per day. In a specific aspect, the conjugate can be administered at or below a dose that is the maximum dose tolerated without undue toxicity. In specific embodiments, where the disease or disorder is myeloid leukemia, the dosage given is in a range of between greater than 4 µg/kg to about 20 µg/kg.

In another embodiment, where the disease is myelodysplastic syndrome, the dosage given is at least 4 µg/kg or greater.

In some embodiments of the invention, the dosage of a conjugate of the invention or pharmaceutical composition thereof administered is at least 1.5, 1.6, 1.8, 2, 2.5, 3, 4, 5, 6, 7, 8, 10, 20, 30, 40, 50, 60, 70, 80, 90 or 100 times lower than the maximum tolerated dose (MTD) over a period of one week, two weeks, one month, three months, four months, six months, nine months, 1 year, 2 years, 3 years, 4 years, or more.

In some embodiments of the invention, the dosage of a conjugate of the invention or pharmaceutical composition thereof administered is at least 1.1, 1.2, 1.3, 1.4, 1.5, 1.6, 1.8, 2, 2.5, 3, 4, 5, 6, 7, 8, 10, 20, 30, 40, 50, 60, 70, 80, 90, or 100 times lower than the human equivalent dose (HED) of the no observed adverse effect level (NOAEL) over a period of one week, two weeks, one month, three months, four months, six months, nine months, 1 year, 2 years, 3 years, 4 years, or more. See the discussion in Section 5.3, supra.

In certain embodiments, the dosage of a conjugate of the invention is administered as an intravenous infusion over about 1, 2, 3, 4, 5, 6, 7, 8, 9, 10, 11, 12, 13, 14, 15, 20, 25, 30, 35, 40, 45, 50, 55, 60, 120, 180, or 240 minutes.

Generally, the dosage of a conjugate of the invention administered to a subject to prevent, treat, and/or manage cancer is in the range of 0.01 to 500 µg/kg, and more typically, in the range of 0.1 µg/kg to 100 µg/kg, of the subject's body weight. In one embodiment, the dosage administered to a subject is in the range of 0.1 µg/kg to 50 µg/kg, or 1 µg/kg to 50 µg/kg, of the subject's body weight, more preferably in the range of 0.1 µg/kg to 25 µg/kg, 1 µg/kg to 25 µg/kg, or 4 to 12.5 µg/kg, of the patient's body weight. In a preferred embodiment, the dosage of conjugate of the invention administered to a subject is 4 µg/kg, 5.32 µg/kg, 7.07 µg/kg, 9.4 µg/kg, or 12.5 µg/kg. of the patient's body weight.

In a specific embodiment, the dosage of a conjugate of the invention administered to a subject to prevent, treat, and/or manage cancer in a patient is 500 µg/kg or less, preferably 250 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 12.5 µg/kg or less, 10 µg/kg or less, 9.4 µg/kg or less, 7.07 µg/kg or less, 5.32 µg/kg or less, 5 µg/kg or less, 4 µg/kg or less, 2.5 µg/kg or less, 2 µg/kg or less, 1.5 µg/kg or less, or 1 µg/kg or less, of a patient's body weight.

In a preferred embodiment, the dosage of conjugate of the invention administered to a subject to treat, prevent and/or manage cancer in a patient is a dose of 4 µg/kg, 5.32 µg/kg, 7.07 µg/kg, 9.4 µg/kg, or 12.5 µg/kg, of the subject's body weight, administered three times a week, over a period of two weeks. In a specific aspect of this embodiment, the conjugate of the invention is administered every day for five days. In other embodiments, the dosing may be repeated for multiple cycles, wherein the number of cycles chosen may or may not factor in the measurement of anti-DT antibodies in the patient.

In another specific embodiment, the dosage of a conjugate of the invention administered to a subject to prevent, treat, and/or manage cancer in a patient is a unit dose of 0.1 µg to 20 µg, 0.1 µg to 15 µg, 0.1 µg to 12 µg, 0.1 µg to 10 µg, 0.1 µg to 8 µg, 0.1 µg to 7 µg, 0.1 µg to 5 µg, 0.1 to 2.5 µg, 0.25 µg to 20 µg, 0.25 to 15 µg, 0.25 to 12 µg, 0.25 to 10 µg, 0.25 to 8 µg, 0.25 µg to 7 µg, 0.25 µg to 5 µg, 0.5 µg to 2.5 µg, 1 µg to 20 µg, 1 µg to 15 µg, 1 µg to 12 µg, 1 µg to 10 µg, 1 µg to 8 µg, 1 µg to 7 µg, 1 µg to 5 µg, or 1 µg to 2.5 µg.

In a specific embodiment, the dosage of a conjugate of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body's surface area. In one embodiment, the dosage administered to a subject is in the range of 0.5 g/m$^2$ to 5 g/m$^2$, or 1 g/m$^2$ to 5 g/m$^2$ of the subject's body's surface area.

In other embodiments, the prophylactically and/or therapeutically effective regimen comprises administering to a patient one or more doses of an effective amount of a conjugate of the invention, wherein the dose of an effective amount achieves a plasma level of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the compound of the invention.

In other embodiments, the prophylactically and/or therapeutically effective regimen comprises administering to a patient a plurality of doses of an effective amount of a conjugate of the invention, wherein the plurality of doses maintains a plasma level of at least 0.1 µg/ml, at least 0.15 µg/ml, at least 0.17 µg/ml, at least 0.2 µg/ml, at least 0.23 µg/ml, at least 0.25 µg/ml, at least 0.3 µg/ml, at least 0.34 µg/ml, at least 0.4 µg/ml, at least 0.45 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 1751 g/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the compound of the invention for at least 1 month, 2 months, 3 months, 4 months, 5 months, 6 months, 7 months, 8 months, 9 months, 10 months, 11 months, 12 months, 15 months, 18 months, or 24 months.

In another embodiment, the present invention encompasses prophylactically and/or therapeutically effective regimens wherein an amount of DT-IL3 conjugate is administered to a patient to achieve plasma levels of DT-IL3 conjugate in the range of at least 0.1 µg/ml to at least 20 µg/ml; at least 0.1 µg/ml to at least 50 µg/ml, at least 0.1 µg/ml to at least 100 µg/ml, at least 0.1 µg/ml to at least 200 µg/ml, at least 0.1 µg/ml to at least 300 µg/ml, at least 0.1 µg/ml to at least 400 µg/ml, at least 0.1 µg/ml to at least 500 µg/ml, at least 0.1 µg/ml to at least 600 µg/ml, at least 0.1 µg/ml to at least 700 µg/ml, or at least 0.1 µg/ml to at least 800 µg/ml for at least 1 month, 2 months, 3 months, 4 months, 5 months, 6 months, 7 months, 8 months, 9 months, 10 months, 11 months, 12 months, 15 months, 18 months, or 24 months.

In some embodiments, the response of a patient to a prophylactically and/or therapeutically effective regimen is monitored and the regimen is maintained or adjusted based on a comparison to a reference point and/or model. In one embodiment, the regimen is maintained or adjusted based on the monitoring of cancer cells. In another embodiment, the regimen is maintained or adjusted based on the monitoring of cancer stem cells.

In specific embodiments, the patient's response to a treatment regimen is monitored through the collection and analysis of a sample from the patient such as, but not limited to, a biological sample, e.g., the patient's blood, bone marrow, normal tissue, or tumor biopsy. In one embodiment, the reference point and/or model comprises pharmacokinetic or immune response data from the patient undergoing therapy, wherein the data is collected at an earlier time point (e.g., prior to receiving the regimen, as a baseline reference sample, or at an earlier time point while receiving therapy). In another embodiment, the reference point and/or model is from a healthy, non-cancer afflicted patient. In a preferred embodiment, the reference point is from a patient that has achieved remission of cancer of the same type as the patient undergoing treatment.

In certain embodiments, the response of a patient to a prophylactically and/or therapeutically effective regimen is monitored by measuring serum or plasma concentrations of a conjugate of the invention over time. In some embodiments, the prophylactic and/or therapeutic regimen is adjusted as a result of the pharmacokinetic data obtained. For example, the frequency and/or dosage administered to the patient may be adjusted. In some embodiments, the response of a patient to a prophylactically and/or therapeutically effective regimen is monitored by assessing the patient's immune response to the conjugate administered to the patient. In a specific embodiment, the patient's anti-diphtheria toxin (anti-DT) antibody titer is monitored. Several aspects of the regimen may be varied based on the comparison including, but not limited to, the dosage and frequency of administration and the temporal regimen of administration.

In some embodiments, the titer of anti-DT antibodies in a patient is measured prior to administration of a conjugate of the invention. The pretreatment anti-DT antibody titer may be considered in determining the eligibility of a patient to receive a conjugate of the invention, or the prophylactically and/or therapeutically effective regimen administered to the patient. For example, a patient's anti-DT antibody titer may suggest administering a conjugate of the invention at a particular dosage, at a particular frequency and/or for a certain period of time.

In some embodiments, the prophylactically and/or therapeutically effective regimen comprises administration of a conjugate of the invention in combination with one or more additional cancer therapeutics. See Section 5.3.2. Preferably, the dosages of the one or more additional cancer therapeutics used in the combination therapy is lower than those which have been or are currently being used to prevent, treat, and/or manage cancer. The recommended dosages of the one or more additional cancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10th ed., Mc-Graw-Hill, New York, 2001; *Physician's Desk Reference* (60$^{th}$ ed., 2006), which is incorporated herein by reference in its entirety.

The conjugate of the invention and the one or more additional cancer therapeutics can be administered separately, simultaneously, or sequentially. In various embodiments, the compound of the invention and the additional cancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more cancer therapeutics are administered within the same patient visit.

In certain embodiments, the conjugate of the invention and the additional cancer therapeutic are cyclically administered. Cycling therapy involves the administration of one cancer therapeutic for a period of time, followed by the administration of a second cancer therapeutic for a period of time and repeating this sequential administration, i.e., the cycle, in order to reduce the development of resistance to one or both of the cancer therapeutics, to avoid or reduce the side effects of one or both of the cancer therapeutics, and/or to improve the efficacy of the therapies.

In a preferred embodiment, the cancer therapeutics are administered concurrently to a subject in separate compositions. The combination cancer therapeutics of the invention may be administered to a subject by the same or different routes of administration.

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When a conjugate of the invention and the additional cancer therapeutic are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics of the invention can be administered separately, in any appropriate form and by any suitable route. When the components of the combination cancer therapeutics are not administered in the same pharmaceutical composition, it is understood that they can be administered in any order to a subject in need thereof. For example, a conjugate of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart. In one embodiment, the cancer therapeutics are administered within the same office visit. In another embodiment, the combination cancer therapeutics of the invention are administered at 1 minute to 24 hours apart.

5.3.2 Types of Diseases and Disorders

The present invention provides methods of treating or preventing or managing a disease or disorder characterized by cells expressing the IL-3 receptor beta subunit in humans by administering to humans in need of such treatment or prevention a pharmaceutical composition comprising an amount of IL-3-diphtheria toxin conjugate of the invention effective to treat or prevent the disease or disorder. In certain embodiments, the disease or disorder is not a hematologic cancer. In other embodiments, the disease or disorder is an allergic disease or disorder. In other embodiments, the disease or disorder is an inflammatory disease or disorder. In another embodiment, the disease or disorder is one characterized as affecting plasmacytoid dendritic cells (e.g., dentritic cell cancers such as NK blastic leukemia and $CD4^+$ $CD56^+$ dermatologic neoplasm). In certain embodiments, the subjects have acute myelogenous leukemia (AML). In certain other embodiments, the subjects have myelodysplastic syndrome (MDS). In other embodiments, the subjects have chronic myelomonocytic leukemia (CMML), CML, ALL, hairy cell leukemia, Hodgkin's disease, or non-Hodgkin's lymphoma.

The present invention encompasses methods for preventing, treating, managing, and/or ameliorating an inflammatory disorder or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from an infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a viral respiratory infection or one or more symptoms thereof.

In an embodiment of the invention, diseases that are characterized by plasmacytoid dendritic cells, which cells demonstrate high expression of the alpha chain of the IL-3 receptor, are targeted. Such diseases include, but are not limited to, HIV, herpes, CMV, autoimmune diseases, and cancers including but not limited to NK blastic lymphoma, dendritic cell cancer including plasmacytoid dendritic cell cancer, and dermatologic neoplasms.

Autoimmune Disorders

In certain embodiments, the invention provides a method of preventing, treating, managing, and/or ameliorating an autoimmune disorder or one or more symptoms thereof, said method comprising administering to a subject in need thereof a dose of an effective amount of one or more pharmaceutical compositions of the invention, wherein the cells involved in such disorders express the interleukin-3 receptor beta subunit. In autoimmune disorders, the immune system triggers an immune response and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress, destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin.

Examples of autoimmune disorders that can be prevented, treated, managed, and/or ameliorated by the methods of the invention include, but are not limited to, adrenergic drug resistance, alopecia greata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, dense deposit disease, discoid lupus, essential mixed cryoglobulinemia, fibromyalgia-fibromyositis, glomerulonephritis (e.g., IgA nephrophathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, lichen planus, lupus erythematosus, Meniere's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychrondritis, Polyendocrinopathies, polyglandular syndromes, polymyalgia rheumatica, polymyositis and dermatomyositis, post-MI, primary agammaglobulinemia, primary biliary cirrhosis, psoriasis, psoriatic arthritis, Raynauld's phenomenon, relapsing polychondritis, Reiter's syndrome, rheumatic heart disease, rheumatoid arthritis, sarcoidosis, scleroderma, Sjögren's syndrome, stiff-man syndrome, systemic lupus erythematosus, takayasu arteritis, temporal arteritis/giant cell arteritis, ulcerative colitis, urticaria, uveitis, Uveitis Opthalmia, vasculitides such as dermatitis herpetiformis vasculitis, vitiligo, and Wegener's granulomatosis.

Allergies

In certain embodiments, the invention provides a method of preventing, treating, managing, and/or ameliorating one or more allergic diseases or allergies or one or more symptoms thereof, wherein the cells involved in such diseases or allergies express the interleukin-3 receptor beta subunit, said method comprising administering to a subject in need thereof a dose of an effective amount of one or more pharmaceutical compositions of the invention. Immune-mediated allergic (hypersensitivity) reactions are classified into four types (I-IV) according to the underlying mechanisms leading to the manifestation of the allergic symptoms. Type I allergic reactions are immediate hypersensitivity reactions characterized by IgE-mediated release of vasoactive substances such as histamine from mast cells and basophils. Over hours, the mast cells and basophils release proinflammatory cytokines producing vasodilation, increased capillary permeability, glandular hypersecretion, smooth muscle spasm, and tissue infiltration with eosinophils and other inflammatory cells.

Type II allergic reactions are cytotoxic hypersensitivity reactions and involve IgG or IgM antibodies bound to cell surface antigens with subsequent complement fixation. Certain cytotoxic cells, such as killer T cells or macrophages, are activated, bind to cells coated with IgG and destroy the target cells. Type II reactions may result in cytolysis or tissue damage.

Type III reactions are immune-complex reactions resulting from deposits of circulating antigen-antibody immune complexes in blood vessels or tissues. Acute inflammation results from the immune-complex initiating a sequence of events that results in polymorphonuclear cell migration and release of lysosomal proteolytic enzymes and permeability factors in tissues.

Type IV reactions are delayed hypersensitivity reactions caused by sensitized T lymphocytes after contact with a specific antigen. Activated sensitized T lymphocytes cause immunologic injury by direct toxic effect or through release of lymphokines and other soluble substances. The activated T lymphocytes may also release cytokines that affect the activity of macrophages, neutrophils, and lymphoid killer cells.

Allergic reactions can be immediate, late-phase, or chronic. Continuous or chronic exposure to an allergen can result in chronic allergic inflammation. Tissues of sites of chronic inflammation contain eosinophils and T cells that release mediators that can cause tissue damage, increased inflammation, and increased sensitivity.

Currently, allergic reactions are treated with drugs such as antihistamines, corticosteroids, vasodilators, bronchodilators, leukotriene inhibitors, and immunomodulators which attempt to alleviate the symptoms associated with the allergic reaction.

Cancer

Any type of cancer in which the cancer stem cells or cancer cells express the interleukin-3 receptor beta and/or alpha subunits can be prevented, treated, and/or managed in accordance with the invention. Non-limiting examples of cancers that can be prevented, treated, and/or managed in accordance with the invention include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; dendritic cell cancer, including plasmacytoid dendritic cell cancer, NK blastic lymphoma (also known as cutaneous NK/T- cell lymphoma and agranular (CD4+/CD56+) dermatologic neoplasms); basophilic leukemia; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The prophylactically and/or therapeutically effective regimens are also useful in the treatment, prevention and/or management of a variety of cancers or other abnormal proliferative diseases wherein the cells of such diseases express the interleukin-3 receptor beta subunit, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. In some embodiments, cancers associated with aberrations in apoptosis are prevented, treated and/or managed in accordance with the methods of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are prevented, treated and/or managed in accordance with the methods of the invention. In other specific embodiments, a sarcoma, melanoma, or leukemia is prevented, treated and/or managed in accordance with the methods of the invention. In certain embodiments, the subjects have acute myelogenous leukemia (AML). In certain other embodiments, the subjects have myelodysplastic syndrome (MDS). In other embodiments, the subjects have chronic myelomonocytic leukemia (CMML). In other specific embodiments, myelodysplastic syndrome is prevented, treated and/or managed in accordance with the methods of the invention.

5.3.3 Target Patient Populations

In accordance with the invention, the pharmaceutical compositions of the present invention are administered to humans in need of inhibition of cells that express the alpha subunit (in specific embodiments, the alpha and beta subunits) of interleukin-3. In certain embodiments, the growth of such cells is inhibited. In other embodiments, the conjugates of the present invention are administered to humans with diseases and disorders associated with overexpression of the IL-3 receptor. In certain embodiments, the subject does have myeloid leukemia. In other embodiments, the disease or disorder is an allergic disease or disorder. In some embodiments, the disease or disorder is an autoimmune disease. In certain embodiments, the subjects have acute myelogenous leukemia (AML). In certain other embodiments, the subjects have myelodysplastic syndrome (MDS). In other embodiments, the subjects have chronic myelomonocytic leukemia (CMML).

In accordance with the invention, pharmaceutical compositions of the present invention are administered to subjects developing, developed, or expected to develop cancer (e.g., subjects with a genetic predisposition for a particular type of cancer, subjects that have been exposed to a carcinogen, subjects with newly diagnosed cancer, subjects that have failed treatment for cancer, subjects who have relapsed from cancer, or subjects that are in remission from a particular cancer). Such subjects may or may not have been previously treated for cancer or may be in remission, relapsed, or may have failed treatment. Such patients may also have abnormal cytogenetics. The pharmaceutical compositions may be used as any line of cancer therapy, e.g., a first line, second line, or third line of cancer therapy. In a specific embodiment, the subject to receive or receiving a pharmaceutical composition of the invention is receiving or has received other cancer therapies. In another embodiment the subject to receive a pharmaceutical composition of the invention is receiving other cancer therapies and pharmaceutical compositions of the invention are administered to the subject before any adverse effects or intolerance of these other cancer therapies occurs. In an alternative embodiment, the subject to receive or receiving a pharmaceutical composition of the invention has not received or is not receiving other cancer therapies.

In a specific embodiment, the subject has been diagnosed with cancer using techniques known to one of skill in the art including, but not limited to, physical examination (e.g., prostate examination, breast examination, lymph nodes examination, abdominal examination, skin surveillance, general palpation), visual methods (e.g., colonoscopy, bronchoscopy, endoscopy), PAP smear analyses (cervical cancer), stool guaiac analyses, blood tests (e.g., complete blood count (CBC) test, prostate specific antigen (PSA) test, carcinoembryonic antigen (CEA) test, cancer antigen (CA)-125 test, alpha-fetoprotein (AFP), liver function tests), karyotyping analyses, bone marrow analyses (e.g., in cases of hematological malignancies), histology, flow cytometry, cytology, a sputum analysis and imaging methods (e.g., computed tomography (CT), magnetic resonance imaging (MRI), ultrasound, X-ray imaging, mammography, PET scans, radionuclide scans, bone scans). Subjects may or may not have been previously treated for cancer.

In one embodiment, a pharmaceutical composition of the invention is administered to a subject that is undergoing or has undergone surgery to remove a tumor neoplasm. In a specific embodiment, a pharmaceutical composition of the invention is administered to a subject concurrently or following surgery to remove a tumor or neoplasm. In another embodiment, a pharmaceutical composition of the invention is administered to a subject before surgery to remove a tumor or neoplasm and, in some embodiments, during and/or after surgery.

In one embodiment, a pharmaceutical composition of the invention is administered to a subject after a course of therapy with the goal of killing cancer cells. In some embodiments, the course of therapy involves the administration of bolus doses of chemotherapeutic agents and/or bolus doses of radiation therapy. In a specific embodiment, a pharmaceutical composition of the invention is administered to a subject after the subject has received a course of therapy involving a dose which is at, or is below, the maximum tolerated dose or the no observed adverse effect level doses of one or more chemotherapeutic agents and/or radiation therapy.

In certain embodiments, a pharmaceutical composition of the invention is administered to a subject as an alternative to chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy where the therapy has proven or may prove too toxic, i.e., results in unacceptable or unbearable side effects for the subject. In some embodiments, a prophylactically and/or therapeutically effective regimen is administered to a subject that is susceptible to adverse reactions from other cancer therapies. The subject may, e.g., have a suppressed immune system (e.g., post-operative patients, chemotherapy patients, and patients with immunodeficiency disease), have an impaired renal or liver function, be elderly, be a child, be an infant, have a neuropsychiatric disorder, take a psychotropic drug, have a history of seizures, or be on medication that would negatively interact with the cancer therapies.

In a specific embodiment, a pharmaceutical composition of the invention is administered to subjects that will, are or have radiation therapy. Among these subjects are those that have received chemotherapy, hormonal therapy, small molecule therapy, anti-angiogenic therapy, differentiation therapy, targeted therapy, radioimmunotherapy, epigenetic therapy, and/or biological therapy, including immunotherapy as well as those who have undergone surgery.

In another embodiment, a pharmaceutical composition of the invention is administered to subjects that will, are, or have received hormonal therapy and/or biological therapy, including immunotherapy. Among these subjects are those that have received chemotherapy, small molecule therapy, anti-angiogenic therapy, differentiation therapy, targeted therapy, radioimmunotherapy, epigenetic therapy, and/or radiation therapy as well as those who have undergone surgery.

In certain embodiments, a pharmaceutical composition of the invention is administered to a subject refractory to one or more therapies. In one embodiment, that a cancer is refractory to a therapy means that at least some significant portion of the cancer cells are not killed or their cell division is not arrested. The determination of whether the cancer cells are refractory can be made either in vivo or in vitro by any method known in the art for assaying the effectiveness of a therapy on cancer cells, using the art-accepted meanings of "refractory" in such a context. In various embodiments, a cancer is refractory where the amount of cancer cells has not been significantly reduced, or has increased. In other embodiments, that a cancer is refractory means that at least some significant portion of cancer stem cells are not killed or their cell division arrested. The determination of whether the cancer stem cells are refractory can be made either in vivo or in vitro by any methods known in the art or described herein.

In some embodiments, a pharmaceutical composition of the invention is administered to reverse the resistance to, or increase the sensitivity of cancer cells to certain hormonal, radiation and chemotherapeutic agents thereby resensitizing the cancer cells to one or more of these agents, which can then be administered (or continue to be administered) to treat or manage cancer, including to prevent metastasis. In a specific embodiment, the regimens of the invention are administered to patients with increased levels of the cytokine IL-6, which has been associated with the development of cancer cell resistance to different treatment regimens, such as chemotherapy and hormonal therapy.

In some embodiments, a pharmaceutical composition of the invention is administered to a subject with a mean absolute lymphocyte count of at least approximately 400 cells/mm$^3$, at least 500 cells/mm$^3$, at least approximately 600 cells/mm$^3$, at least approximately 700 cells/mm$^3$, at least approximately 800 cells/mm$^3$, at least approximately 900 cells/mm$^3$, at least approximately 1000 cells/mm$^3$, at least approximately 1100 cells/mm$^3$, at least approximately 1200 cells/mm$^3$. In other embodiments, a prophylactically and/or therapeutically effective regimen of the invention is administered to a subject with a mean absolute lymphocyte count of approximately 400 cells/mm$^3$ to approximately 1200 cells/mm$^3$, approximately 500 cells/mm$^3$ to approximately 1200 cells/mm$^3$, approximately 600 cells/mm$^3$ to approximately 1200 cells/mm$^3$, approximately 700 cells/mm$^3$ to approximately 1200 cells/mm$^3$, approximately 800 cells/mm$^3$ to approximately 1200 cells/mm$^3$, approximately 900 cells/mm$^3$ to approximately 1200 cells/mm$^3$, approximately 1000 cells/mm$^3$ to approximately 1200 cells/mm$^3$. In a more specific embodiment, the regimen results in a mean absolute lymphocyte count of at least approximately 400 cells/mm$^3$.

In some embodiments, a pharmaceutical composition of the invention is administered to a subject that is in remission. In a specific embodiment, the subject has no detectable cancer, i.e., no cancer is detectable using a conventional method described herein (e.g., MRI) or known to one of skill in the art. In another embodiment, a pharmaceutical composition of the invention is administered to a patient that does not have a detectable immune response to diphtheria toxin. In a preferred embodiment, the immune response is detected by ELISA.

5.3.4 Combination Therapies

The present invention also provides methods for preventing, treating, and/or managing cancer, the methods comprising administering to a patient (e.g., a human patient) in need thereof, a prophylactically and/or a therapeutically effective regimen, the regimen comprising administering to the patient a pharmaceutical composition of the invention and one or more additional therapies, said additional therapy not being a conjugate of the invention. In a specific embodiment, the combination therapies of the invention comprise a pharmaceutical composition in accordance with the invention and at least one other therapy that has the same mechanism of action as said conjugate. In another specific embodiment, the combination therapies of the invention comprise a pharmaceutical composition identified in accordance with the methods of the invention and at least one other therapy (e.g., prophylactic or therapeutic agent) which has a different mechanism of action than said conjugate. The pharmaceutical composition of the invention and the additional therapy can be administered separately, concurrently, or sequentially. The combination of agents can act additively or synergistically. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Any therapy (e.g., therapeutic or prophylactic agent) which is useful, has been used, or is currently being used for the prevention, treatment, and/or management of cancer can be used in compositions and methods of the invention. Therapies (e.g., therapeutic or prophylactic agents) include, but are not limited to, peptides, polypeptides, antibodies, conjugates, nucleic acid molecules, small molecules, mimetic agents, synthetic drugs, inorganic molecules, and organic molecules. Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy. In certain embodiments, a prophylactically and/or therapeutically effective regimen of the invention comprises the administration of a combination of therapies.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandomate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi I mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. US 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents"); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodelglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer stem cells includes i) antibodies, antibody fragments, and proteins that are either naked or conjugated to a therapeutic moiety that target certain cell surface targets on cancer stem cells, or ii) small molecules known in the art including ones that can be further optimized (e.g. via chemistry) or identified via a cancer stem cell-based screen (e.g. such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mcl-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) used in combination with a compound of the invention is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) used in combination with a compound of the invention is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) used in accordance with the invention is not an anti-angiogenic agent.

In some embodiments, the therapy(ies) used in combination with a compound of the invention is an anti-inflammatory agent. Non-limiting examples of anti-inflammatory agents include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FO- RADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTA-SONE™), prednisolone (PRELONE™ and PEDI-APRED™), triamcinolone, azulfidine, and inhibitors of eicosanoids (e.g., prostaglandins, thromboxanes, and leukotrienes. Other examples of anti-inflammatory agents can be found, e.g., in U.S. Publication No. 005/0002934 A1 at paragraphs 290-294, which is incorporated by reference in its entirety. In other embodiments, the therapy(ies) used in accordance with the invention is not an anti-inflammatory agent.

In certain embodiments, the therapy(ies) used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

The invention includes the use of agents that target cancer stem cells in combination with a compound of the invention. In some embodiments, the agent used is an agent that binds to a marker, e.g., antigen on cancer stem cells. In a specific embodiment, the agent binds to an antigen that is expressed at a greater level on cancer stem cells than on normal stem cells. In a specific embodiment, the agent binds specifically to a cancer stem cell antigen. In other embodiments, the therapy(ies) used in accordance with the invention is an agent that binds to a marker on cancer stem cells. Non-limiting examples of antigens on cancer stem cells that can be used to target cancer stem cells include CD34+/CD38−, CD34+/CD38−/CD123+, CD44+/CD24−, CD133+, CD34+/CD10−/CD19−, CD138−/CD34−/CD19+, CD20+, CD133+/RC2+, and CD44+/α2β1hi/C133+. In one embodiment, the agent that binds to a marker on cancer stem cells is an antibody. In another embodiment, the agent that binds to a marker on cancer stem cells is a ligand. In certain embodiments, the antibody or ligand is attached directly or indirectly to a therapeutic moiety. Non-limiting examples of therapeutic moieties include, but are not limited to alkylating agents, anti-metabolites, plant alkaloids, cytotoxic agents, chemotherapeutic agents (e.g., a steroid, cytosine arabinoside, fluoruracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, Pseudomonas exotoxin, a bacterical endotoxin or the lipid A moiety of a bacterial endotoxin), growth modulators and RNase.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the α-subunit of IL-3R (i.e., the CD123 antigen). In other embodiments, the antibody, antibody-conjugate, antibody fragment, or antibody fragment-conjugate binds to the IL-3R, containing both the α and β subunits. Methods for preparing antibodies to IL-3R and mimetics of antibodies to IL-3R are described in U.S. Pat. No. 6,733,743 B2, which is incorporated herein by reference in its entirety.

In certain embodiments, antibodies or fragments that bind to a marker on cancer stem cells are substantially non-immunogenic in the treated subject. Non-immunogenic antibodies include, but are not limited to, chimerized antibodies, humanized antibodies, and antibodies from the same species as the subject receiving the therapy. Antibodies or fragments that bind to markers in cancer stem cells can be produced using techniques known in the art. See, for example, paragraphs 539-573 of U.S. Publication No. 2005/0002934 A1, which is incorporated by reference in its entirety.

The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to, therapeutic enzymes, chemotherapeutic agents, cytokines, radionuclides, toxins, RNase, and antimetabolites. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody, an antibody fragment, an antibody conjugated to a therapeutic moiety, or an antibody fragment conjugated to a therapeutic moiety.

In some embodiments, a compound of the invention is used in combination with radiation therapy comprising the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation-based therapy. Non-limiting examples of such therapies include a chemotherapy and radiation therapy as described supra.

Currently available cancer therapies and their dosages, routes of administration and recommended usage are known in the art and have been described in such literature as the Physician's Desk Reference (60th ed., 2006). In accordance with the present invention, the dosages and frequency of administration of chemotherapeutic agents are described supra.

5.4 Methods of Monitoring Cancer Stem Cells

As part of the prophylactically effective and/or therapeutically effective regimens of the invention, the cancer stem cell population can be monitored to assess the efficacy of a therapy as well as to determine prognosis of a subject with cancer or the efficacy of a therapeutically or prophylactically effective regimen. In certain embodiments of the prophylactically effective and/or therapeutically effective therapies or regimens of the invention, the therapies or regimens result in a stabilization or reduction in the cancer stem cell population in the patient. In one embodiment, the subject undergoing the regimen is monitored to assess whether the regimen has resulted in a stabilization or reduction in the cancer stem cell population in the subject.

In some embodiments, the amount of cancer stem cells in a subject is determined using a technique well-known to one of skill in the art or described in Section 5.7 below.

In accordance with the invention, cancer stem cells comprise a unique subpopulation (often 0.1-10% or so) of a tumor that, in contrast to the remaining 90% or so of the tumor (i.e., the tumor bulk), are relatively more tumorigenic and relatively more slow-growing or quiescent. Given that conventional therapies and regimens have, in large part, been designed to attack rapidly proliferating cells (i.e., those cancer cells that comprise the tumor bulk), slower growing cancer stem cells may be relatively more resistant than faster growing tumor bulk to conventional therapies and regimens. This would explain another reason for the failure of standard oncology treatment regimens to ensure long-term benefit in most patients with advanced stage cancers. In a specific embodiment, a cancer stem cell(s) is the founder cell of a tumor (i.e., it is the progenitor of cancer cells). In some embodiments, a cancer stem cell(s) has one, two, three, or more or all of the following characteristics or properties: (i) can harbor the ability to initiate a tumor and/or to perpetuate tumor growth, (ii) can be generally relatively less mutated than the bulk of a tumor (e.g. due to slower growth and thus fewer DNA replication-dependent errors, improved DNA repair, and/or epigenetic/non-mutagenic changes contributing to their malignancy), (iii) can have many features of a normal stem cell(s) (e.g., similar cell surface antigen and/or intracellular expression profile, self-renewal programs, multi-drug resistance, an immature phenotype, etc., characteristic of normal stem cells) and may be derived from a normal stem cell(s), (iv) can be potentially responsive to its microenvironment (e.g., the cancer stem cells may be capable of being induced to differentiate and/or divide asymmetrically), (v) can be the source of metastases, (vi) can be slow-growing or quiescent, (vii) can be symmetrically-dividing, (viii) can be tumorigenic (e.g as determined by NOD/SCID implantation experiments), (ix) can be relatively resistant to traditional therapies (i.e. chemoresistant), and (x) can comprise a subpopulation of a tumor (e.g relative to the tumor bulk).

In other embodiments, the amount of cancer stem cells in a sample from a subject is determined/assessed using a technique described herein or well-known to one of skill in the art. Such samples include, but are not limited to, biological samples and samples derived from a biological sample. In certain embodiments, in addition to the biological sample itself or in addition to material derived from the biological sample such as cells, the sample used in the methods of this invention comprises added water, salts, glycerin, glucose, an antimicrobial agent, paraffin, a chemical stabilizing agent, heparin, an anticoagulant, or a buffering agent. In certain embodiments, the biological sample is blood, serum, urine, bone marrow or interstitial fluid. In another embodiment, the sample is a tissue sample. In a particular embodiment, the tissue sample is breast, brain, skin, colon, lung, liver, ovarian, pancreatic, prostate, renal, bone or skin tissue. In a specific embodiment, the tissue sample is a biopsy of normal or tumor tissue. The amount of biological sample taken from the subject will vary according to the type of biological sample and the method of detection to be employed. In a particular embodiment, the biological sample is blood, serum, urine, or bone marrow and the amount of blood, serum, urine, or bone marrow taken from the subject is 0.1 ml, 0.5 ml, 1 ml, 5 ml, 8 ml, 10 ml or more. In another embodiment, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

In accordance with the methods of the invention, a sample derived from a biological sample is one in which the biological sample has been subjected to one or more pretreatment steps prior to the detection and/or measurement of the cancer stem cell population in the sample. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps. In certain embodiments, the sample is pretreated by removing cells other than stem cells or cancer stem cells from the sample, or removing debris from the sample prior to the determination of the amount of cancer stem cells in the sample according to the methods of the invention.

The samples for use in the methods of this invention may be taken from any animal subject, preferably mammal, most preferably a human. The subject from which a sample is obtained and utilized in accordance with the methods of this invention includes, without limitation, an asymptomatic subject, a subject manifesting or exhibiting 1, 2, 3, 4, or more symptoms of cancer, a subject clinically diagnosed as having cancer, a subject predisposed to cancer, a subject suspected of having cancer, a subject undergoing therapy for cancer, a subject that has been medically determined to be free of cancer (e.g., following therapy for the cancer), a subject that is managing cancer, or a subject that has not been diagnosed with cancer. In certain embodiments, the term "has no detectable cancer," as used herein, refers to a subject or subjects in which no cancer is detectable using a conventional method described herein (e.g., MRI) or known to one of skill in the art. In other embodiments, the term refers to a subject or subjects free from any disorder.

In certain embodiments, the amount of cancer stem cells in a subject or a sample from a subject assessed prior to therapy or regimen (e.g. at baseline) or at least 1, 2, 4, 6, 7, 8, 10, 12, 14, 15, 16, 18, 20, 30, 60, 90 days, 6 months, 9 months, 12 months, >12 months after the subject begins receiving the therapy or regimen. In certain embodiments, the amount of cancer stem cells is assessed after a certain number of doses (e.g., after 2, 5, 10, 20, 30, or more doses of a therapy). In other embodiments, the amount of cancer stem cells is assessed after 1 week, 2 weeks, 1 month, 2 months, 1 year, 2 years, 3 years, 4 years, or more after receiving one or more therapies.

In certain embodiments, a positive or negative control sample is a sample that is obtained or derived from a corresponding tissue or biological fluid as the sample to be analyzed in accordance with the methods of the invention. This sample may come from the same patient or different persons and at the same or different time points.

For clarity of disclosure, and not by way of limitation, the following pertains to analysis of a blood sample from a patient. However, as one skilled in the art will appreciate, the assays and techniques described herein can be applied to other types of patient samples, including a body fluid (e.g. blood, bone marrow, plasma, urine, bile, ascitic fluid), a tissue sample suspected of containing material derived from a cancer (e.g. a biopsy) or homogenate thereof. The amount of sample to be collected will vary with the particular type of sample and method of determining the amount of cancer stem cells used and will be an amount sufficient to detect the cancer stem cells in the sample.

A sample of blood may be obtained from a patient having different developmental or disease stages. Blood may be drawn from a subject from any part of the body (e.g., a finger, a hand, a wrist, an arm, a leg, a foot, an ankle, a stomach, and a neck) using techniques known to one of skill in the art, in particular methods of phlebotomy known in the art. In a specific embodiment, venous blood is obtained from a subject and utilized in accordance with the methods of the invention. In another embodiment, arterial blood is obtained and utilized in accordance with the methods of the invention. The composition of venous blood varies according to the metabolic needs of the area of the body it is servicing. In contrast, the composition of arterial blood is consistent throughout the body. For routine blood tests, venous blood is generally used.

The amount of blood collected will vary depending upon the site of collection, the amount required for a method of the invention, and the comfort of the subject. In some embodiments, any amount of blood is collected that is sufficient to detect the amount or amount of cancer stem cells. In a specific embodiment, 1 cc or more of blood is collected from a subject.

The amount of cancer stem cells in a sample can be expressed as the percentage of, e.g., overall cells, overall cancer cells or overall stem cells in the sample, or quantitated relative to area (e.g. cells per high power field), or volume (e.g. cells per ml), or architecture (e.g. cells per bone spicule in a bone marrow specimen).

In some embodiments, the sample may be a blood sample, bone marrow sample, or a tissue/tumor biopsy sample, wherein the amount of cancer stem cells per unit of volume (e.g., 1 ml) or other measured unit (e.g., per unit field in the case of a histological analysis) is quantitated. In certain embodiments, the cancer stem cell population is determined as a portion (e.g., a percentage) of the cancerous cells present in the blood or bone marrow or tissue/tumor biopsy sample or as a subset of the cancerous cells present in the blood or bone marrow or tissue/tumor biopsy sample. The cancer stem cell population, in other embodiments, can be determined as a portion (e.g., percentage) of the total cells. In yet other embodiments, the cancer stem cell population is determined as a portion (e.g., a percentage) of the total stem cells present in the blood sample.

In other embodiments, the sample from the patient is a tissue sample (e.g., a biopsy from a subject with or suspected of having cancerous tissue), where the amount of cancer stem cells can be measured, for example, by immunohistochemistry or flow cytometry, or on the basis of the amount of cancer stem cells per unit area, volume, or weight of the tissue. In certain embodiments, the cancer stem cell population is determined as a portion (e.g., a percentage) of the cancerous cells present in the tissue sample or as a subset of the cancerous cells present in the tissue sample. In yet other embodiments, the cancerous stem cell population is determined as a portion (e.g., a percentage) of the overall cells or stem cells in the tissue sample.

The amount of cancer stem cells in a test sample can be compared with the amount of cancer stem cells in a reference sample(s) to assess the efficacy of the regimen. In one embodiment, the reference sample is a sample obtained from the subject undergoing therapy at an earlier time point (e.g., prior to receiving the regimen as a baseline reference sample, or at an earlier time point while receiving the therapy). In this embodiment, the therapy desirably results in a decrease in the amount of cancer stem cells in the test sample as compared with the reference sample. In another embodiment, the reference sample is obtained from a healthy, subject that has no detectable cancer, or from a patient that is in remission for the same type of cancer. In this embodiment, the therapy desirably results in the test sample having an equal amount of cancer stem cells, or less than the amount of cancer stem cells than are detected in the reference sample.

In other embodiments, the cancer stem cell population in a test sample can be compared with a predetermined reference range and/or a previously detected amount of cancer stem cells determined for the subject to gauge the subject's response to the regimens described herein. In a specific embodiment, a stabilization or reduction in the amount of cancer stem cells relative to a predetermined reference range and/or earlier (previously detected) cancer stem cell amount determined for the subject indicates an improvement in the subject's prognosis or a positive response to the regimen, whereas an increase relative to the predetermined reference range and/or earlier cancer stem cell amount indicates the same or worse prognosis, and/or a failure to respond to the regimen. The cancer stem cell amount can be used in conjunction with other measures to assess the prognosis of the subject and/or the efficacy of the regimen. In a specific embodiment, the predetermined reference range is based on the amount of cancer stem cells obtained from a patient or population(s) of patients suffering from the same type of cancer as the patient undergoing the therapy.

Generally, since stem cell antigens can be present on both cancer stem cells and normal stem cells, a sample from the cancer-afflicted patient will have a higher stem cell count than a sample from a healthy subject with no detectable cancer, due to the presence of the cancer stem cells. The therapy will desirably result in a cancer stem cell count for the test sample (e.g., the sample from the patient undergoing therapy) that decreases and becomes increasingly closer to the stem cell count in a reference sample that is a sample from a healthy subject with no detectable cancer by a conventional method.

If the reduction in amount of cancer stem cells is determined to be inadequate upon comparing the amount of cancer stem cells in the sample from the subject undergoing the regimen with the reference sample, then the medical practitioner has a number of possible options to adjust the regimen.

For instance, the medical practitioner can then increase either the dosage or intensity of the therapy administered, the frequency of the administration, the duration of administration, combine the therapy with another therapy(ies), change the management altogether including halting therapy, or any combination thereof.

In certain embodiments, the dosage, frequency and/or duration of administration of a therapy is modified as a result of the change in the amount of cancer stem cells detected in or from the treated patient. For example, if a subject receiving therapy for leukemia has a cancer stem cell measurement of 2.5% of his tumor prior to therapy and 5% after 6 weeks of therapy, then the therapy or regimen may be altered or stopped because the increase in the percentage of cancer stem cells indicates that the therapy or regimen is not optimal. Alternatively, if another subject with leukemia has a cancer stem cell measurement of 2.5% of his tumor prior to therapy and 1% after 6 weeks of therapy, then the therapy or regimen may be continued because the decrease in the percentage of cancer stem cells indicates that the therapy or regimen is effective.

The amount of cancer stem cells can be monitored/assessed using standard techniques known to one of skill in the art. Cancer stem cells can be monitored by, e.g., obtaining a sample, such as a tissue/tumor sample, blood sample or a bone marrow sample, from a subject and detecting cancer stem cells in the sample. The amount of cancer stem cells in a sample (which may be expressed as percentages of, e.g., overall cells or overall cancer cells) can be assessed by detecting the expression of antigens on cancer stem cells. Techniques known to those skilled in the art can be used for measuring these activities. Antigen expression can be assayed, for example, by immunoassays including, but not limited to, western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, protein A immunoassays, flow cytometry, and FACS analysis. In such circumstances, the amount of cancer stem cells in a test sample from a subject may be determined by comparing the results to the amount of stem cells in a reference sample (e.g., a sample from a subject who has no detectable cancer) or to a predetermined reference range, or to the patient him/herself at an earlier time point (e.g. prior to, or during therapy).

In a specific embodiment, the cancer stem cell population in a sample from a patient is determined by flow cytometry. This method exploits the differential expression of certain surface markers on cancer stem cells relative to the bulk of the tumor. Labeled antibodies (e.g., fluorescent antibodies) can be used to react with the cells in the sample, and the cells are subsequently sorted by FACS methods. In some embodiments, a combination of cell surface markers are utilized in order to determine the amount of cancer stem cells in the sample. For example, both positive and negative cell sorting may be used to assess the amount of cancer stem cells in the sample. Cancer stem cells for specific tumor types can be determined by assessing the expression of markers on cancer stem cells. In certain embodiments, the tumors harbor cancer stem cells and their associated markers as set forth in Table 2 below, which provides a non-limiting list of cancer stem cell phenotypes associated with various types of cancer.

TABLE 2

| Tumor | Cancer Stem Cell Phenotype |
|---|---|
| Leukemia (AML) | CD34+/CD38− |
| Breast | CD44+/CD24− |
| Brain | CD133+ |
| Leukemia (ALL) | CD34+/CD10−/CD19− |
| Ovarian | CD44+/CD24− |
| Multiple Myeloma | CD138−/CD34−/CD19+ |
| Chronic myelogenous leukemia | CD34+/CD38− |
| Melanoma | CD20+ |
| Ependymoma | CD133+/RC2+ |
| Prostate | CD44+/$\alpha_2\beta_1^{hi}$/CD133+ |

Additional cancer stem cell markers include, but are not limited to, CD123, CLL-1, combinations of SLAMs (signaling lymphocyte activation molecule family receptors; see Yilmaz et al., "SLAM family markers are conserved among hematopoietic stem cells from old and reconstituted mice and markedly increase their purity," Hematopoiesis 107: 924-930 (2006)), such as CD150, CD244, and CD48, and those markers disclosed in U.S. Pat. No. 6,004,528 to Bergstein, in pending U.S. patent application Ser. No. 09/468,286, and in U.S. Patent Application Publication Nos. 2006/0083682, 2007/0036800, 2007/0036801, 2007/0036802, 2007/0041984, 2007/0036803, and 2007/0036804, each of which are incorporated herein by reference in their entirety. See, e.g., Table 1 of U.S. Pat. No. 6,004,528 and Tables 1, 2, and 3 of U.S. patent application Ser. No. 09/468,286 and U.S. Patent Application Publication Nos. 2006/0083682, 2007/0036800, 2007/0036801, 2007/0036802, 2007/0041984, 2007/0036803, and 2007/0036804.

In a specific embodiment the cancer stem population in a sample, e.g., a tissue sample, such as a solid tumor biopsy, is determined using immunohistochemistry techniques. This method exploits the differential expression of certain surface markers on cancer stem cells relative to the bulk of the tumor. Labeled antibodies (e.g., fluorescent antibodies) can be used to react with the cells in the sample, and the tissue is subsequently stained. In some embodiments, a combination of certain cell surface markers are utilized in order to determine the amount of cancer stem cells in the sample. Cancer stem cells for specific tumor types can be determined by assessing the expression of certain markers that are specific to cancer stem cells. In certain embodiments, the tumors harbor cancer stem cells and their associated markers as set forth in Table 2 above.

Suitable cancer stem cell antigens may be identified: (i) through publicly available information, such as published and unpublished expression profiles including cell surface antigens of cancer stem cells of a particular tumor type or adult stem cells for a particular tissue type (e.g. Table 2), and/or (ii) by cloning cancer stem cells or adult stem cells of a particular tumor or tissue type, respectively, in order to determine their expression profiles and complement of cell surface antigens. Cloning of normal stem cells is a technique routinely employed in the art (Uchida et al., "Heterogeneity of hematopoeitic stem cells," Curr. Opin. Immunol. 5:177-184 (1993)). In fact, this same technique is used to identify normal stem cells and cancer stem cells. Moreover, assumption that a proportion of normal stem cell gene products, e.g. cell surface antigens, will also be present on cancer stem cells derived from the same tissue type has proven an effective way to identify cancer stem cell gene products and cancer stem cells. For example, knowledge that the normal hematopoietic stem cell was CD34+/CD38− resulted in the determination that acute myeloid leukemia (AML) stem cells is similarly CD34+/CD38−. This indeed was confirmed by standard stem cell cloning techniques (See Bonnet et al., "Human acute myeloid leukemia is organized as a hierarchy that originates from a primitive hematopoietic cell," *Nat. Med.* 3:730-737 (1997)). Brain cancer stem cells were similarly isolated using a marker of normal (brain) stem cells, in this case CD133 (See Singh et al. "Identification of human brain tumor initiating cells," *Nature* 432(7015):396-401 (2004)).

In certain embodiments using flow cytometry of a sample, the Hoechst dye protocol can be used to identify cancer stem cells in tumors. Briefly, two Hoechst dyes of different colors (typically red and blue) are incubated with tumor cells. The cancer stem cells, in comparison with bulk cancer cells, overexpress dye efflux pumps on their surface that allow these cells to pump the dye back out of the cell. Bulk tumor cells largely have fewer of these pumps, and are therefore relatively positive for the dye, which can be detected by flow cytometry. Typically a gradient of dye positive ("dye$^+$") vs. dye negative ("dye$^-$") cells emerges when the entire population of cells is observed. Cancer stem cells are contained in the dye- or dye low (dye$^{low}$) population. For an example of the use of the Hoechst dye protocol to characterize a stem cell population see Goodell et al., "A leukemic stem cell with intrinsic drug efflux pump capacity in acute myeloid leukemia," *Blood*, 98(4):1166-1173 (2001) and Kondo et al., "Persistence of a small population of cancer stem-like cells in the C6 glioma cell line," *Proc. Natl. Acad. Sci. U.S.A.* 101:781-786 (2004). In this way, flow cytometry could be used to measure cancer stem cell amount pre- and post-therapy to assess the change in cancer stem cell amount arising from a given therapy or regimen.

In other embodiments using flow cytometry of a sample, the cells in the sample may be treated with a substrate for aldehyde dehydrogenase that becomes fluorescent when catalyzed by this enzyme. For instance, the sample can be treated with BODIPY®-aminoacetaldehyde which is commercially available from StemCell Technologies Inc. as Aldefluor®. Cancer stem cells express high levels of aldehyde dehydrogenase relative to bulk cancer cells and therefore become brightly fluorescent upon reaction with the substrate. The cancer stem cells, which become fluorescent in this type of experiment, can then be detected and counted using a standard flow cytometer. In this way, flow cytometry could be used to measure cancer stem cell amount pre- and post-therapy to assess the change in cancer stem cell amount arising from a given therapy or regimen.

In other embodiments, a sample (e.g., a tumor or normal tissue sample, blood sample or bone marrow sample) obtained from the patient is cultured in in vitro systems to assess the cancer stem cell population. For example, tumor samples can be cultured on soft agar, and the amount of cancer stem cells can be correlated to the ability of the sample to generate colonies of cells that can be visually counted. Colony formation is considered a surrogate measure of stem cell content, and thus, can be used to quantitate the amount of cancer stem cells. For instance, with hematological cancers, colony-forming assays include colony forming cell (CFC) assays, long-term culture initiating cell (LTC-IC) assays, and suspension culture initiating cell (SC-IC) assays. In this way, the colony-forming or related a assay, such as long-term perpetuation/passage of a cell line, could be used to measure cancer stem cell amount pre- and post-therapy to assess the change in cancer stem cell amount arising from a given therapy or regimen.

In other embodiments, sphere formation is measured to determine the amount of cancer stem cells in a sample (e.g., cancer stem cells form three-dimensional clusters of cells, called spheres) in appropriate media that is conducive to forming spheres. Spheres can be quantitated to provide a measure of cancer stem cells. See Singh et al., "Identification of a Cancer Stem Cell from Human Brain Tumors," *Cancer Res.* 63: 5821-5828 (2003). Secondary spheres can also be measured. Secondary spheres are generated when the spheres that form from the patient sample are broken apart, and then allowed to reform. In this way, the sphere-forming assay could be used to measure cancer stem cell amount pre- and post-therapy to assess the change in cancer stem cell amount arising from a given therapy or regimen.

In other embodiments, the amount of cancer stem cells in a sample can be determined with a cobblestone assay. Cancer stem cells from certain hematological cancers form "cobblestone areas" (CAs) when added to a culture containing a monolayer of bone marrow stromal cells. For instance, the amount of cancer stem cells from a leukemia sample can be assessed by this technique. The tumor samples are added to the monolayer of bone marrow stromal cells. The leukemia cancer stem cells, more so than the bulk leukemia cells, have the ability to migrate under the stromal layer and seed the formation of a colony of cells which can be seen visually under phase contrast microscopy in approximately 10-14 days as CAs. The number of CAs in the culture is a reflection of the leukemia cancer stem cell content of the tumor sample, and is considered a surrogate measure of the amount of stem cells capable of engrafting the bone marrow of immunodeficient mice. This assay can also be modified so that the CAs can be quantitated using biochemical labels of proliferating cells instead of manual counting, in order to increase the throughput of the assay. See Chung et al., "Enforced expression of an Flt3 internal tandem duplication in human CD34+ cells confers properties of self-renewal and enhanced erythropoiesis," *Blood* 105(1):77-84 (2005). In this way, the cobblestone assay could be used to measure cancer stem cell amount pre- and post-therapy to assess the change in cancer stem cell amount arising from a given therapy or regimen.

In other embodiments, a sample (e.g., a tumor or normal tissue sample, blood sample or bone marrow sample) obtained from the patient is analyzed in in vivo systems to determine the cancer stem cell population. In certain embodiments, for example, in vivo engraftment is used to quantitate the amount of cancer stem cells in a sample. In vivo engraftment involves implantation of a human specimen with the readout being the formation of tumors in an animal such as in immunocompromised or immunodeficient mice (such as NOD/SCID mice). Typically, the patient sample is cultured or manipulated in vitro and then injected into the mice. In these assays, mice can be injected with a decreasing amount of cells from patient samples, and the frequency of tumor formation can be plotted vs. the amount of cells injected to determine the amount of cancer stem cells in the sample. Alternatively, the rate of growth of the resulting tumor can be measured, with larger or more rapidly advancing tumors indicating a higher cancer stem cell amount in the patient sample. In this way, an in vivo engraftment model/assay could be used to measure cancer stem cell amount pre- and post-therapy to assess the change in cancer stem cell amount arising from a given therapy or regimen.

The amount of cancer stem cells in a specimen can be compared to a predetermined reference range and/or an earlier amount of cancer stem cells previously determined for the subject (either prior to, or during therapy) in order to gauge the subject's response to the treatment regimens described herein. In a specific embodiment, a stabilization or reduction in the amount of cancer stem cells relative to a predetermined reference range and/or earlier cancer stem cell amount previously determined for the subject (either prior to, or during therapy) indicates that the therapy or regimen was effective and thus possibly an improvement in the subject's prognosis, whereas an increase relative to the predetermined reference range and/or cancer stem cell amount detected at an earlier time point indicates that the therapy or regimen was ineffective and thus possibly the same or a worsening in the subject's prognosis. The cancer stem cell amount can be used with other standard measures of cancer to assess the prognosis of the subject and/or efficacy of the therapy or regimen: such as response rate, durability of response, relapse-free survival, disease-free survival, progression-free survival, and overall survival. In certain embodiments, the dosage, frequency and/or duration of administration of a therapy is modified as a result of the determination of the amount of cancer stem cells at various time points which may include prior to, during, and/or following therapy.

The present invention also relates to methods for determining that a cancer therapy or regimen is effective at targeting and/or impairing cancer stem cells by virtue of monitoring cancer stem cells over time and detecting a stabilization or decrease in the amount of cancer stem cells during and/or following the course of the cancer therapy or regimen.

In a certain embodiment, a therapy or regimen may be described or marketed as an anti-cancer stem cell therapy or regimen based on the determination that a therapy or regimen is effective at targeting and/or impairing cancer stem cells by virtue of having monitored or detected a stabilization or decrease in the amount of cancer stem cells during therapy.

5.5 Methods of Monitoring Cancer Cells

As part of the prophylactically and/or therapeutically effective regimens of the invention, the amount of cancer cells (alone or in combination with the amount of cancer stem cells) can be monitored/assessed using standard techniques known to one of skill in the art. In certain embodiments of the prophylactically and/or therapeutically effective regimens of the invention, the regimens result in a stabilization or reduction in the amount (expressed, e.g., as a percentage) of cancer cells in the subject. In one embodiment, the subject undergoing the regimen is monitored to determine whether the regimen has resulted in a stabilization or reduction in the amount (expressed, e.g., as a percentage) of cancer cells in the subject.

In some embodiments, the amount of cancer cells is assessed in a subject using techniques described herein or known to one of skill in the art. In other embodiments, the amount of cancer cells is detected in a sample. Such samples include, but are not limited to, biological samples and samples derived from a biological sample. In certain embodiments, in addition to the biological sample itself or in addition to material derived from the biological sample such as cells, the sample used in the methods of this invention comprises added water, salts, glycerin, glucose, an antimicrobial agent, paraffin, a chemical stabilizing agent, heparin, an anticoagulant, or a buffering agent. In certain embodiments, the biological sample is blood, serum, urine, bone marrow, or interstitial fluid. In another embodiment, the sample is a tissue sample. In a particular embodiment, the tissue sample is breast, colon, lung, liver, ovarian, pancreatic, prostate, renal, bone, or skin tissue. In a specific embodiment, the tissue sample is a biopsy, including a tumor biopsy. The amount of biological sample taken from the subject will vary according to the type of biological sample and the method of detection to be employed. In a particular embodiment, the biological sample is blood, serum, or urine and the amount of blood, serum, or urine taken from the subject is 0.1 ml, 0.5 ml, 1 ml, 5 ml, 10 ml or more. In another embodiment, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

In accordance with the methods of the invention, a sample derived from a biological sample is one in which the biological sample has been subjected to one or more pretreatment steps prior to the detection and/or measurement of the cancer cell population in the sample. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps. In certain embodiments, the sample is pretreated by removing cells other than cancer cells from the sample, or removing debris from the sample prior to the determination of the amount of cancer cells in the sample according to the methods of the invention.

The samples for use in the methods of this invention may be taken from any animal subject, preferably mammal, most preferably a human. The subject from which a sample is obtained and utilized in accordance with the methods of this invention includes, without limitation, an asymptomatic subject, a subject manifesting or exhibiting 1, 2, 3, 4, or more symptoms of cancer, a subject clinically diagnosed as having cancer, a subject predisposed to cancer, a subject suspected of having cancer, a subject undergoing therapy for cancer, a subject that has been medically determined to be free of cancer (e.g., following therapy for the cancer), a subject that is managing cancer, or a subject that has not been diagnosed with cancer.

In certain embodiments, the amount of cancer cells is assessed in a subject or a sample from a subject at least 1, 2, 4, 6, 7, 8, 10, 12, 14, 15, 16, 18, 20, or 30, 60, 90 days 6 months, 9 months, 12 months, or >12 months after the subject begins receiving the regimen. In certain embodiments, the amount of cancer cells is assessed after a number of doses (e.g., after 1, 2, 5, 10, 20, 30, or more doses of a therapy). In other embodiments, the amount of cancer cells is assessed after 2 weeks, 1 month, 2 months, 1 year, 2 years, 3 years, 4 years, or more after receiving one or more therapies.

The amount of cancer cells in a sample can be expressed as the percentage of, e.g., overall cells in the sample. In some embodiments, the sample is a blood sample or bone marrow sample, wherein the amount of cancer cells per unit of volume (e.g., 1 ml) or other measured unit (e.g., per unit field in the case of a histological analysis) is quantitated. The cancer cell population, in certain embodiments, can be determined as a percentage of the total blood cells.

In other embodiments, the sample from the patient is a tissue sample (e.g., a biopsy from a subject with or suspected or having cancerous tissue), where the amount of cancer cells can be measured, for example, by immunohistochemistry or on the basis of the amount of cancer cells per unit weight of the tissue.

The amount of cancer cells in the test sample can be compared with the amount of cancer cells measured in a reference sample(s) to assess the efficacy of the regimen. In one embodiment, the reference sample is a sample from the subject undergoing therapy, at an earlier time point (e.g., prior to receiving the regimen as a baseline reference sample, or at an earlier time point while receiving the therapy). In this embodiment, the therapy desirably results in a decrease in the amount of cancer cells in the test sample as compared with the reference sample. In another embodiment, the reference sample is obtained from a healthy subject with no detectable cancer, or from a patient that is in remission for the same type of cancer. In this embodiment, the therapy desirably results in the test sample having an equal amount of cancer cells as detected in the reference sample (e.g., no detectable cancer cells).

If the reduction in the amount of cancer cells is judged too small, then the medical practitioner has a number of options to adjust the regimen. For instance, the medical practitioner can then either increase the dosage of the therapy administered, the frequency of the administration, the duration of administration, combine the therapy with another therapy (ies), halt the therapy, or any combination thereof.

The amount of cancer cells can be monitored/assessed using standard techniques known to one of skill in the art. Cancer cells can be monitored by, e.g., obtaining a sample, such as a tumor sample, blood sample or bone marrow sample, from a subject and detecting cancer cells in the sample. The amount of cancer cells in a sample (which may be expressed as a percentage) can be assessed by detecting the expression of antigens on cancer cells and/or by detecting the proliferation of cancer cells. Techniques known to those skilled in the art can be used for measuring these activities. For example, cellular proliferation can be assayed by 3H-thymidine incorporation assays and trypan blue cell counts. Antigen expression can be assayed, for example, by immunoassays including, but not limited to western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, flow cytometry, fluorescence-activated cell sorting (FACS) analysis, and immunofluorescence.

The amount of cancer cells can be compared to a predetermined reference range and/or an earlier amount of cancer cells determined for the subject to gauge the subject's response to the regimens described herein. In a specific embodiment, a reduction in the amount of cancer cells relative to a predetermined reference range and/or earlier cancer cell amount determined for the subject indicate an improvement in the subject's prognosis or response to a therapy, whereas an increase relative to the predetermined reference range and/or earlier cancer cell amount indicates the same or worse prognosis, or failure to respond to a therapy. In certain embodiments, the dosage, frequency and/or duration of administration of a therapy is modified as a result of the change in the amount of cancer cells.

In some embodiments, the cancer cell population can be monitored/assessed using gross measurements of the cancer cell population. For example, in some embodiments, the cancer cell population is determined using imaging methods such as computed tomography (CT), magnetic resonance imaging (MRI), ultrasound, X-ray imaging, mammography, radionuclide imaging, PET scan or bone scans.

In embodiments of the invention comprising treatment of solid tumors, the bulk size of the tumor may provide an estimate of the cancer cell population. A number of known methods can be used to assess the bulk size of the tumor. Non-limiting examples of such methods include imaging methods (e.g., computed tomography (CT), magnetic resonance imaging (MRI), PET scans, ultrasound, X-ray imaging, mammography, bone scans and radioisotope imaging), visual methods (e.g., colonoscopy, bronchoscopy, endoscopy), physical examination (e.g., prostate examination, breast examination, lymph nodes examination, abdominal examination, general palpation), blood tests (e.g., prostate specific antigen (PSA) test, carcinoembryonic antigen (CEA) test, cancer antigen (CA)-125 test, alpha-fetoprotein (AFP)), bone marrow analyses (e.g., in cases of hematological malignancies), histopathology, cytology and flow cytometry.

In some embodiments, the bulk tumor size can be measured by assessments based on the size of tumor lesions determined from imaging methods. In specific embodiments, the assessments are performed in accordance with the Response Evaluation Criteria In Solid Tumors (RECIST) Guidelines, which are set forth in Therasse, P. et al., "New Guidelines to Evaluate the Response to Treatment in Solid Tumors," *J. of the Nat. Canc. Inst.* 92(3), 205-216 (2000). For instance, in specific embodiments, lesions in the subject that are representative of bulk tumor size are selected so that they are at least =20 mm in their longest diameter at baseline (prior to treatment) when conventional imaging techniques are used (e.g., conventional CT scan, MRI or X-ray) and lesions that are at least =10 mm in their longest diameter at baseline should be selected when spiral CT scanning is used.

5.6 Methods of Monitoring Lymphocyte Cell Count, Neutrophil Cell Count, Platelet Count and Hemoglobin As part of the prophylactically and/or therapeutically effective regimens of the invention, peripheral blood lymphocyte counts can be monitored/assessed using standard techniques known to one of skill in the art. Peripheral blood lymphocyte counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in a subject can be determined by, e.g., separating the lymphocytes from other components of peripheral blood such as plasma using, e.g., Ficoll-Hypaque (Pharmacia) gradient centrifugation. Labeling the T-cells with an antibody directed to a T-cell antigen such as CD3, CD4, and CD8 which is conjugated to a FACS detectable agent, such as FITC or phycoerythrin, and measuring the amount of T-cells by FACS. Further, the effect on a particular subset of T cells (e.g., CD2+, CD4+, CD8+, CD45+, CD45RO+, CD45RA+, or CD8+ RA+) or NK cells can be determined using standard techniques known to one of skill in the art, such as FACS.

The subject's absolute neutrophil count (ANC) can be monitored/assessed using standard techniques known to one of skill in the art. In some embodiments, the regimen includes monitoring the patient's ANC in order to avoid the risk of the patient developing neutropenia.

The ANC can be calculated from measurements of the total number of white blood cells (WBC) and the numbers of neutrophils and bands (immature neutrophils). The ANC can be determined manually by trained medical technologists or by automated ANC results obtained from automated hematology analyzers.

The subject's platelet count (PLT) can be monitored/assessed using standard techniques known to one of skill in the art. In some embodiments, the regimen includes monitoring the patient's platelet count in order to avoid the risk of the patient developing thrombocytopenia or becoming blood transfusion dependent. Transfusions can be given as determined by the physician.

The subject's hemoglobin (Hgb) can be monitored/assessed using standard techniques known to one of skill in the art. In some embodiments, the regimen includes monitoring the patient's hemoglobin in order to avoid the risk of the patient developing anemia or becoming transfusion dependent. Transfusions or growth factors (e.g. erythropoietin) can be given as determined by the physician.

5.7 Biological Assays 5.7.1 In Vitro Assays

The compounds, pharmaceutical compositions and regimens of the invention can be tested in vitro and/or in vivo for their ability to reduce the amount of cancer cells and/or cancer stem cells, or inhibit their proliferation. The ability of a compound or a regimen of the invention to reduce the amount of cancer cells, cancer stem cells and/or immune cells (e.g., lymphocytes) or inhibit their proliferation can be assessed by: detecting the expression of antigens on cancer cells, cancer stem cells, and/or immune cells; detecting the proliferation or viability of cancer cells, cancer stem cells and immune cells; detecting the effector function of cancer cells and cancer stem cells. Techniques known to those skilled in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and FACS analysis.

A compound, pharmaceutical composition, or regimen of the invention is preferably tested in vitro and then in vivo for the desired therapeutic or prophylactic activity prior to use in humans. For example, assays which can be used to determine whether administration of a specific compound is indicated include cell culture assays in which a patient tissue sample (e.g., a cancer cell or cancer stem cell) is grown in culture and exposed to, or otherwise contacted with, a compound of the invention, and the effect of such compound upon the tissue sample is observed. The tissue sample can be obtained by biopsy from the patient. This test allows the identification of the therapeutically most effective therapy (e.g., prophylactic or therapeutic agent) for each individual patient.

Determination of cell viability using the XTT assay: In some cases, CD34+ cells are isolated from human cord blood using magnetic beads coated with anti-CD34 antibody. Isolated cells are then counted and aliquoted into 96-well plates and then incubated in the presence of varying concentrations of cantharidin or norcantharidin. Cell viability is mesured by the addition of the XTT colorimetric reagent. Viability is determined by the absorbance of treated cultures at approximately 450-500 nm compared to untreated cultures. In other cases, the cells used in the assay may be a leukemia cell line, such as Mv4; 11. The assay can also be used to determine the time course of cell killing by various compounds by performing the XTT assay on cultures that are incubated with the compounds for varying periods of time.

Cobblestone assay: The cobblestone area-forming cell (CAFC) assay exploits a reproducible visual end point for the quantitation of cancer stem cells. Leukemia samples are added to adherent cultures of stromal cells, in some embodiments, MS-5 stromal cells. The cancer stem cells in the culture will migrate below the MS-5 stromal cells and form a colony of cells called a cobblestone that can be visually quantitated. To test the effect of cantharidin or norcantharidin on the cancer stem cell population using this assay, cells are first cultured in the presence of the drug. In some embodiments the cells are cultured for 16 hours. After this incubation, the cells are added to the stromal cultures. A reduction in the cobblestone area formation in cultures that were treated with the drug compared to the untreated cells represents cancer stem cell activity for the drug.

5.7.2 In Vivo Assays

The compounds, pharmaceutical compositions, and regimens of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapeutic modalities (e.g., prophylactic and/or therapeutic agents), whether such therapeutic modalities are administered separately or as an admixture, and the frequency of administration of the therapeutic modalities.

Animal models for cancer can be used to assess the efficacy of a compound or a combination therapy of the invention. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al. *J La. State Med. Soc.* 1998, 150(4):179-85). An example of an animal model for breast cancer includes, but is not limited to, a transgenic mouse that overexpresses cyclin D1 (see, e.g., Hosokawa et al., *Transgenic Res.* 2001, 10(5), 471-8. An example of an animal model for colon cancer includes, but is not limited to, a TCR b and p53 double knockout mouse (see, e.g., Kado et al., *Cancer Res.* 2001, 61(6):2395-8). Examples of animal models for pancreatic cancer include, but are not limited to, a metastatic model of PancO2 murine pancreatic adenocarcinoma (see, e.g., Wang et al., *Int. J. Pancreatol.* 2001, 29(1):37-46) and nu-nu mice generated in subcutaneous pancreatic tumours (see, e.g., Ghaneh et al., *Gene Ther.* 2001, 8(3):199-208). Examples of animal models for non-Hodgkin's lymphoma include, but are not limited to, a severe combined immunodeficiency ("SCID") mouse (see, e.g., Bryant et al., *Lab Invest.* 2000, 80(4), 553-73) and an IgHmu-HOX11 transgenic mouse (see, e.g., Hough et al., *Proc. Natl. Acad. Sci. U.S.A.* 1998, 95(23), 13853-8. An example of an animal model for esophageal cancer includes, but is not limited to, a mouse transgenic for the human papillomavirus type 16 E7 oncogene (see, e.g., Herber et al., *J. Virol.* 1996, 70(3): 1873-81). Examples of animal models for colorectal carcinomas include, but are not limited to, Apc mouse models (see, e.g., Fodde & Smits, *Trends Mol. Med.* 2001, 7(8):369-73 and Kuraguchi et al., *Oncogene* 2000, 19(50), 5755-63).

In certain in vivo techniques, an imaging agent, or diagnostic moiety, is used which binds to molecules on cancer cells or cancer stem cells, e.g., cancer cell or cancer stem cell surface antigens. For instance, a fluorescent tag, radionuclide, heavy metal, or photon-emitter is attached to an antibody (including an antibody fragment) that binds to a cancer stem cell surface antigen. Exemplary cancer stem cell surface antigens are listed above in Table 2. The medical practitioner can infuse the labeled antibody into the patient either prior to, during, or following treatment, and then the practitioner can place the patient into a total body scanner/developer which can detect the attached label (e.g., fluorescent tag, radionuclide, heavy metal, photon-emitter). The scanner/developer (e.g., CT, MRI, or other scanner, e.g. detector of fluorescent label, that can detect the label) records the presence, amount/ quantity, and bodily location of the bound antibody. In this manner, the mapping and quantitation of tag (e.g. fluorescence, radioactivity, etc.) in patterns (i.e., different from patterns of normal stem cells within a tissue) within a tissue or tissues indicates the treatment efficacy within the patient's body when compared to a reference control such as the same patient at an earlier time point or a patient who has no detectable cancer. For example, a large signal (relative to a reference range or a prior treatment date, or prior to treatment) at a particular location indicates the presence of cancer stem cells. If this signal is increased relative to a prior date it suggests a worsening of the disease and failure of therapy or regimen. Alternatively, a signal decrease indicates that therapy or regimen has been effective.

Similarly, in some embodiments of the invention, the efficacy of the therapeutic regimen in reducing the amount of cancer cells in animals (including humans) undergoing treatment can be evaluated using in vivo techniques. In one embodiment, the medical practitioner performs the imaging technique with labeled molecule that specifically binds the surface of a cancer cell, e.g., a cancer cell surface antigen. See Section 5.4, supra, lists certain cancer cell surface antigens. In this manner, the mapping and quantitation of tag (e.g., fluorescence, radioactivity) in patterns within a tissue or tissues indicates the treatment efficacy within the body of the patient undergoing treatment.

In a specific embodiment, the amount of cancer stem cells is detected in vivo in a subject according to a method comprising the steps of: (a) administering to the subject an effective amount of a labeled cancer stem cell marker binding agent that specifically binds to a cell surface marker found on the cancer stem cells, and (b) detecting the labeled agent in the subject following a time interval sufficient to allow the labeled agent to concentrate at sites in the subject where the cancer stem cell surface marker is expressed. In accordance with this embodiment, the cancer stem cell surface marker-binding agent is administered to the subject according to any suitable method in the art, for example, parenterally (e.g. intraveneously), or intraperitoneally. In accordance with this embodiment, the effective amount of the agent is the amount which permits the detection of the agent in the subject. This amount will vary according to the particular subject, the label used, and the detection method employed. For example, it is understood in the art that the size of the subject and the imaging system used will determine the amount of labeled agent needed to detect the agent in a subject using imaging. In the case of a radiolabeled agent for a human subject, the amount of labeled agent administered is measured in terms of radioactivity, for example from about 5 to 20 millicuries of $^{99}$Tc. The time interval following the administration of the labeled agent which is sufficient to allow the labeled agent to concentrate at sites in the subject where the cancer stem cell surface marker is expressed will vary depending on several factors, for example, the type of label used, the mode of administration, and the part of the subject's body that is imaged. In a particular embodiment, the time interval that is sufficient is 6 to 48 hours, 6 to 24 hours, or 6 to 12 hours. In another embodiment the time interval is 5 to 20 days or 5 to 10 days. The presence of the labeled cancer stem cell surface marker-binding agent can be detected in the subject using imaging means known in the art. In general, the imaging means employed depend upon the type of label used. Skilled artisans will be able to determine the appropriate means for detecting a particular label. Methods and devices that may be used include, but are not limited to, computed tomography (CT), whole body scan such as position emission tomography (PET), magnetic resonance imaging (MRI), fluorescence, chemiluminescence, an imager which can detect and localize fluorescent label and sonography. In a specific embodiment, the cancer stem cell surface marker-binding agent is labeled with a radioisotope and is detected in the patient using a radiation responsive surgical instrument (Thurston et al., U.S. Pat. No. 5,441,050). In another embodiment, the cancer stem cell surface marker-binding agent is labeled with a fluorescent compound and is detected in the patient using a fluorescence responsive scanning instrument. In another embodiment, the cancer stem cell surface marker-binding agent is labeled with a positron emitting metal and is detected in the patient using positron emission-tomography. In yet another embodiment, the cancer stem cell surface marker-binding agent is labeled with a paramagnetic label and is detected in a patient using magnetic resonance imaging (MRI).

Any in vitro or in vivo (ex vivo) assays known to those skilled in the art that can detect and/or quantify cancer stem cells can be used to monitor cancer stem cells in order to evaluate the prophylactic and/or therapeutic utility of a cancer therapy or regimen disclosed herein for cancer or one or more symptoms thereof, or these assays can be used to assess the prognosis of a patient. The results of these assays then may be used to possibly maintain or alter the cancer therapy or regimen.

5.7.3 Assessing Toxicity

The toxicity and/or efficacy of compounds, pharmaceutical compositions, and regimens of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic regimens that exhibit large therapeutic indices are preferred. While therapeutic regimens that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the therapies for use in humans. The dosage of such agents lies preferably within a range of circulating concentrations that include the $ED_{50}$ with little or no toxicity to normal tissues. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels of compounds in plasma may be measured, for example, by high performance liquid chromatography.

5.8 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. The pharmaceutical product may contain, for example, a conjugate of the invention in a unit dosage form in a first container, and in a second container, sterile water for injection. Alternatively, the unit dosage form may be a solid suitable for oral, transdermal, intranasal, or topical delivery.

In a specific embodiment, the unit dosage form is suitable for parenteral, intravenous, intramuscular, intranasal, oral, intraperitoneal, topical or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician, or patient on how to appropriately prevent or treat the disease or disorder in question. In other words, the article of manufacture includes instruction means indicating or suggesting a dosing regimen including, but not limited to, actual doses, monitoring procedures, cancer cell counts, cancer stem cell counts, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with cancer, or one or more symptoms thereof by administering specific doses and using specific dosing regimens as described herein.

In a preferred embodiment, the article of manufacture includes labeled antibodies that bind to cancer cells, and preferably, that bind to cancer stem cells. As such, the article contains a method to monitor the efficacy of the therapeutic regimen, and to adjust, if need be, the therapeutic dosages and/or regimens.

The present invention also provides a pharmaceutical pack or kit comprising one or more containers filled with reagents for detecting, monitoring and/or measuring cancer stem cells. In one embodiment, the pharmaceutical pack or kit optionally comprises instructions for the use of the reagents provided for detecting and/or measuring cancer stem cells. In another embodiment, the pharmaceutical pack or kit optionally comprises a notice in the form prescribed by a governmental agency regulating the manufacture, use or sale of pharmaceuticals or biological products, which notice reflects approval by the agency of manufacture, for use or sale for human administration.

In an embodiment, the pharmaceutical pack or kit comprises in one or more containers a cancer stem cell surface marker-binding agent. In a particular embodiment, the agent is an antibody that selectively or specifically binds to a cancer stem cell surface marker. In a particular embodiment, the agent is an antibody (including, e.g., human, humanized, chimeric, monoclonal, polyclonal, Fvs, ScFvs, Fab or F(ab)$_2$ fragments or epitope binding fragments), which cross-reacts with any cancer stem cell surface marker. In another embodiment, the antibody cross reacts with any one of the cancer stem cell surface markers listed in Table 2. In another embodiment, the antibody reacts with any one of the cancer stem cell surface markers listed in Table 1 of U.S. Pat. No. 6,004,528 or Tables 1, 2, or 3 of U.S. patent application Ser. No. 09/468,286, and U.S. Patent Application Publication Nos. 2006/0083682, 2007/0036800, 2007/0036801, 2007/0036802, 2007/0041984, 2007/0036803, and 2007/0036804, each of which is incorporated by reference herein. In accordance with this embodiment, the pharmaceutical pack or kit comprises one or more antibodies which bind to cancer stem cell surface markers, wherein each antibody binds to a different epitope of the cancer stem cell surface marker and/or binds to the cancer stem cell surface marker with a different affinity.

For antibody based kits, the kit can comprise, for example: (1) a first antibody (which may or may not be attached to a solid support) which binds to a cancer stem cell surface marker protein; and, optionally, (2) a second, different antibody which binds to either the cancer stem cell surface marker protein bound by the first antibody, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. As an example, a kit may include an anti-CD34 antibody for positive selection, an anti-CD38 antibody for negative selection, and an anti-CD123 antibody for positive selection to isolate and/or quantify and/or assist in the determination of the amount of leukemia cancer stem cells (which are CD34+/CD38−/CD123+).

For nucleic acid micoarray kits, the kits generally comprise (but are not limited to) probes specific for certain genes attached to a solid support surface. In other embodiments, the probes are soluble. In one such embodiment, probes can be either oligonucleotides or longer length probes including probes ranging from 150 nucleotides in length to 800 nucleotides in length. The probes may be labeled with a detectable label. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a cancer stem cell surface marker nucleic acid sequence. Generally, the materials and reagents for the microarray kits are in one or more containers. Each component of the kit is generally in its own a suitable container.

For Quantitative PCR, the kits generally comprise preselected primers specific for certain cancer stem cell surface marker nucleic acid sequences. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for the nucleic acid sequences associated with or indicative of a condition. The probes may or may not be labeled with a fluorophore. The probes may or may not be labeled with a quencher molecule. In some embodiments, the Quantitative PCR kits also comprise components suitable for reverse-transcribing RNA including enzymes (e.g. reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the assay and methods for interpreting and analyzing the data resulting from the performance of the assay.

A kit can optionally further comprise a predetermined amount of an isolated cancer stem cell surface marker polypeptide or a nucleic acid encoding a cancer stem cell surface marker, e.g., for use as a standard or control. The diagnostic methods of the present invention can assist in conducting or monitoring a clinical study. In accordance with the present invention, suitable test samples, e.g., of serum or tissue, obtained from a subject can be used for diagnosis.

Based on the results obtained by use of the pharmaceutical pack or kit (i.e. whether the cancer stem cell amount has stabilized or decreased), the medical practitioner administering the cancer therapy or regimen may choose to continue the therapy or regimen. Alternatively, based on the result that the cancer stem cell amount has increased, the medical practitioner may choose to continue, alter or halt the therapy or regimen.

6. EXAMPLES

The following examples are illustrative, and should not be viewed as limiting the scope of the present invention. Reasonable variations, such as those that occur to a reasonable artisan, can be made herein without departing from the scope of the present invention.

6.1 Example 1

6.1.1 Patients and Study Design

The following example describes the results of a clinical study in which a diphtheria toxin-interleukin-3 conjugate was administered to patients suffering from acute myeloid leukemia (AML).

Patients were diagnosed with AML based on bone marrow biopsy and either relapsed disease or poor-risk AML (treatment-related, prior myelodysplastic syndrome (MDS), patient age>70 years, or unfavorable cytogenetics and not candidate for allogeneic transplantation). Patients had to have a performance status<2, WBC<10,000/L, bilirubin<1.5 mg/dL, transaminases<2.5×upper limit normal, albumin>3 g/dL, creatinine<1.5 mg/dL, adequate cardiac reserve (EF>40%), anti-DT pretreatment serum concentration<2.4 μg/ml, be willing to give informed consent and be treated at an approved site, be willing to use an approved form of birth control while on study, have no concurrent serious medical problems or uncontrolled infections or DIC or pregnancy, not have active CNS leukemia, not have had a myocardial infarction within the past six months, not require oxygen, and not have an allergy to diphtheria toxin.

Patients were admitted to the hospital, given allopurinol, normal saline, moxifloxacin, fluconazole, vitamin K, acetaminophen, diphenhydramine, and hydrocortisone and inter-patient escalating doses of DT388IL-3 IV over 15 minutes on M-W-F for two weeks. Cohorts of at least 3 patients at each dose level were treated. Patients were monitored for toxicities using the NCI Common Terminology Criteria for Adverse Events (CTCAE) version 3.0. Vital signs were measured frequently on the days of treatment. Careful input/output was recorded daily. CBC, CMP, coagulation panel, LDH, uric acid, and magnesium were tested daily. Blood was drawn for clinical pharmacology studies including pharmacokinetics and immune response. Bone marrow biopsies were repeated on day 15, 30, 60, and every three months until relapse. Responses were measured based on the revised recommendations of the international working group.

6.1.2 Results

Figure 4:
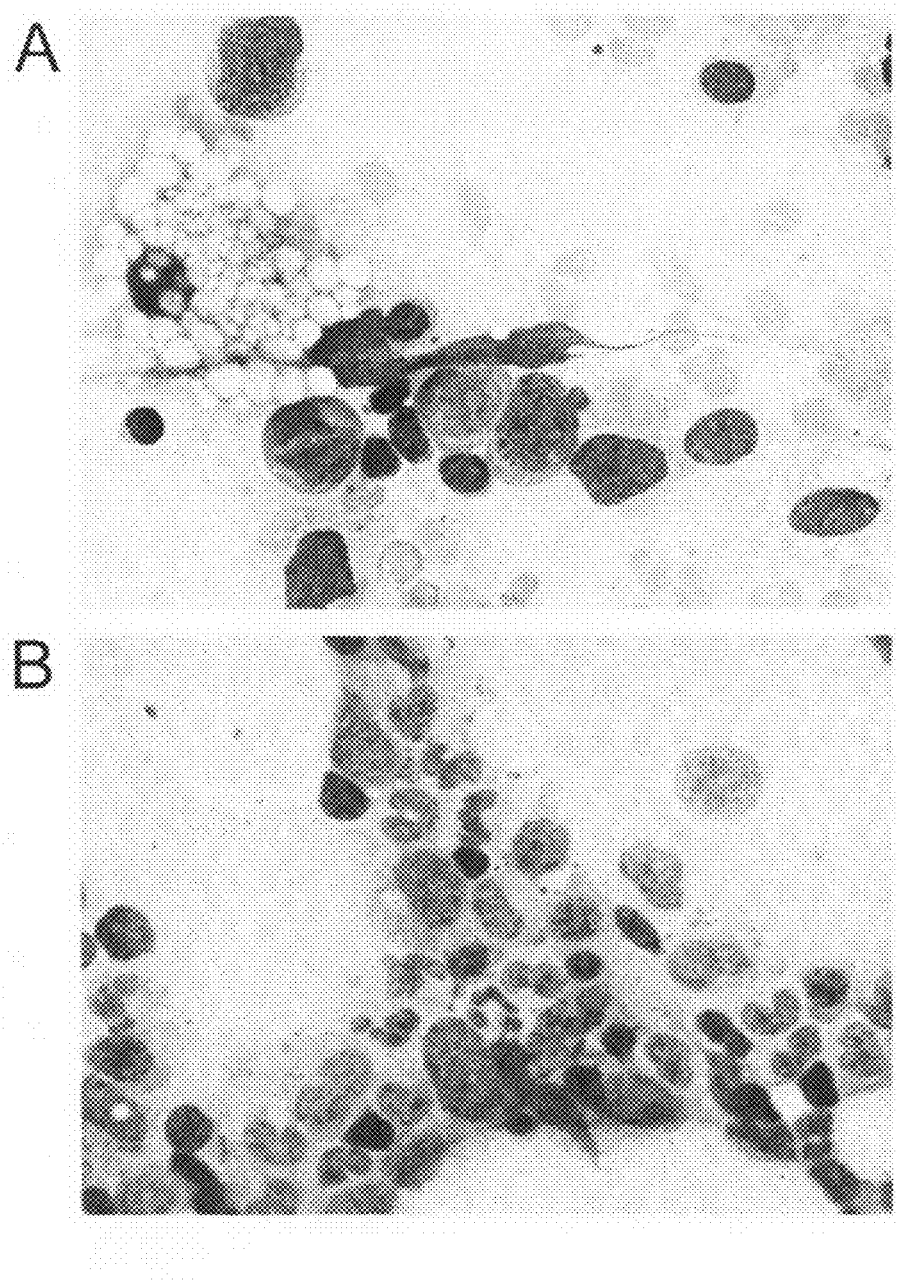

Forty-nine AML patients have been screened and twenty-seven patients treated (Table 3). The median age of treated patients was 59 years (range, 25-81 years). There were thirteen males and fourteen females. Disease was de novo in two, first relapse in ten, second relapse in seven, and refractory in eight patients. Three patients had a history of MDS, and one had a history of secondary AML. One patient each had previously received an autologous or allogeneic stem cell transplant. Cytogenetics were unfavorable in ten, intermediate in sixteen, and not done in one. Seven patients were treated with 4 μg/kg, eight patients were treated with 5.3 μg/kg, eleven patients treated with 7.1 μg/kg, and one patient treated with 9 μg $DT_{388}IL$-3 (Table 4). Drug-related toxicities were mild to moderate and transient including fever, chills, hypotension, hypoxemia, and hypoalbuminemia. Among twenty-seven evaluable patients, we have observed one on-going CR of 6+months duration, two partial remissions (PRs) lasting one and two+months and three minimal responses with clearance of peripheral blasts and marrow blast cytoreductions of 89%, 90% and 93% lasting one to two months (Table 5 and FIG. 4).

Toxicities to date on the clinical study have been mild to moderate. Fevers occurred but responded to acetaminophen and cooling methods. Hypotension and transient uremia responded to hydration. Hypoxemia and hypoalbuminemia reversed with albumin infusions and diuresis. No significant liver dysfunction has been seen. After the clinical study of $DT_{388}mGMCSF$, we established a preclinical model for the liver toxicity using DT fusion molecules with murine GMCSF and IL-3, $DT_{388}mGMCSF$ and $DT_{388}mIL$-3, respectively. 27 Rats treated with $DT_{388}mGMCSF$ but not $DT_{388}mIL$-3 showed Kupffer cell injury, hepatocyte swelling and transaminasemia. The lack of IL-3 receptor on Kupffer cells appears to protect from liver damage. Monkey and clinical studies to date confirms that finding.

The above results clearly show that the diphtheria toxin-interleukin-3 conjugate was selectively cytotoxic to leukemic cells relative to normal hematopoietic cells and produced clinical remissions in human patients.

TABLE 3

Results of $DT_{388}IL3$ treated patients-toxicities, immune response, and clinical response*

| Patient No. | Dose level (ug/kg) | Toxicities Gr2 CTCV3 | Anti-DT antibody (μg/mL) | | | Clinical Response |
|---|---|---|---|---|---|---|
| | | | d1 | d15 | d30 | |
| 1 | 4 | N-V, Trans | 0.8 | 23 | 235 | 0 |
| 2 | 4 | 0 | 2.5 | ND | ND | 0 |
| 3 | 4 | F, N-V, Alb, Hypo | 0 | ND | 36 | 0 |
| 4 | 4 | F, Alb | 0 | ND | ND | 0 |
| 5 | 4 | F, Alb | 0 | ND | 48 | 0 |
| 6 | 4 | Hypo | 0.9 | ND | 36 | 0 |
| 7 | 4 | Alb | 2.2 | 1 | 6.2 | 0 |
| 8 | 5.32 | Alb | 1 | 221 | 263 | 0 |

TABLE 3-continued

Results of DT$_{388}$IL3 treated patients-toxicities, immune response, and clinical response*

| Patient No. | Dose level (ug/kg) | Toxicities Gr2 CTCV3 | Anti-DT antibody (µg/mL) d1 | d15 | d30 | Clinical Response |
|---|---|---|---|---|---|---|
| 9 | 5.32 | Alb, Trans | 0.8 | 440 | ND | PR |
| 10 | 5.32 | Alb | 0.5 | ND | 1.1 | 0 |
| 11 | 5.32 | F, Alb, Trans | 2.5 | ND | ND | 0 |
| 12 | 5.32 | Hypo, F, Alb | 1.3 | 600 | ND | 0 |
| 13 | 5.32 | Alb | 1.5 | ND | ND | MR |
| 14 | 5.32 | Alb, Trans | 0.3 | 0.3 | ND | MR |
| 15 | 5.32 | Alb, Trans | 0 | 1.6 | 29 | MR |
| 16 | 7.07 | Alb, Trans | 1 | 0 | ND | 0 |
| 17 | 7.07 | Alb | 1.2 | ND | ND | 0 |
| 18 | 7.07 | F, Alb, Dysp | 0.7 | 0.4 | ND | 0 |
| 19 | 7.07 | VLS, Alb, Dysp | 0.8 | 8.3 | 22.4 | CR |
| 20 | 7.07 | Alb, Trans | 0.4 | ND | ND | 0 |
| 21 | 7.07 | Alb, Trans | 2.1 | 1.5 | 4.2 | 0 |
| 22 | 7.07 | Alb, Trans | 1.7 | 1.2 | ND | 0 |
| 23 | 7.07 | F, Alb, VLS | 2.2 | 32 | 104 | PR |
| 24 | 7.07 | 0 | 4.3 | ND | 4 | 0 |
| 25 | 7.07 | Alb | 3.8 | ND | ND | 0 |
| 26 | 7.07 | F, alb, Trans | 0.5 | ND | ND | 0 |
| 27 | 9.4 | F, Alb, Trans | 3 | ND | ND | 0 |
| 28 | 9.4 | F, Alb | 1.3 | 300 | ND | 0 |
| 29 | 7.07 | F, Alb | 1.5 | ND | ND | 0 |
| 30 | 9.4 | Alb | 3 | 0.8 | ND | 0 |
| 31 | 9.4 | F, Trans | 2.3 | ND | ND | 0 |
| 32 | 9.4 | Alb, Trans | 2.2 | 3.1 | ND | 0 |
| 33 | 9.4 | Alb, Trans | 1.2 | ND | ND | 0 |
| 34 | 9.4 | Alb, Trans | 2.2 | ND | 306 | 0 |
| 35 | 9.4 | Alb | 0.8 | 252 | ND | 0 |
| 36 | 12.5 | Alb, Trans | 1.3 | 11.2 | 16.8 | PR |

*F = fever, N-V = nausea and vomiting, Trans = transaminasemia, VLS = vascular leak syndrome, Alb = hypoalbuminemia, Hypo = hypotension, Dysp = dyspnea, ND = not determined, MR = minimal response, PR = partial response, CR = complete response.

TABLE 4

Dose level and drug-related toxic effects of DT$_{388}$IL3-treated AML patients

| Patient no. | Dose µg/kg/day | Drug-related Gr 2 or higher side effects (CTC toxicity grade) |
|---|---|---|
| 1 | 4 | Gr 2 nausea; Gr 2 vomiting; Gr 2 ALT |
| 2 | 4 | None |
| 3 | 4 | Gr 2 hypotension; Gr 2 sinus tachycardia; Gr 2 fever; Gr 2 weight gain; Gr 2 nausea; Gr 2 vomiting; Gr 2 hypoalbuminemia; |
| 4 | 4 | Gr 2 fever; Gr 2 hypoalbuminemia; Gr 2 hypocalcemia |
| 5 | 4 | Gr 2 fever; Gr 2 rigors/chills; Gr 2 CPK; Gr 2 hypoalbuminemia; Gr 2 hypocalcemia |
| 6 | 4 | Gr 2 hypotension; Gr 2 hypocalcemia |
| 7 | 4 | Gr 2 hypoalbuminemia |
| 8 | 5.32 | Gr 2 hypoalbuminemia |
| 9 | 5.32 | Gr 2 hypoalbuminemia; Gr 2 hypocalcemia; Gr 2 AST; Gr 2 ALT |
| 10 | 5.32 | Gr 2 supraventicular tachycardia; Gr 2 hypoalbuminemia |
| 11 | 5.32 | Gr 2 fever; Gr 2 hypoalbuminemia; Gr 2 hypocalcemia; Gr 2 AST; Gr 2 ALT |
| 12 | 5.32 | Gr 2 hypotension; Gr 2 fever; Gr 2 rigors/chills; Gr 2 weight gain; Gr 2 hypoalbuminemia; Gr 2 hypocalcemia |
| 13 | 5.32 | Gr 2 hypoalbuminemia |
| 14 | 5.32 | Gr 2 hypoalbuminemia; Gr 2 hypocalcemia; Gr 2 ALT |
| 15 | 5.32 | Gr 2 fatigue; Gr 2 rigors/chills; Gr 2 hypoalbuminemia; Gr 2 hypocalcemia; Gr 2 ALT |
| 16 | 7.07 | Gr 2 hypoalbuminemia; Gr 2 hypocalcemia; Gr 2 ALT |
| 17 | 7.07 | Gr 2 hypoalbuminemia |
| 18 | 7.07 | Gr 2 hypertension; Gr 2 fatigue; Gr 2 fever; Gr 2 rash/desquamation; Gr 2 hypoalbuminemia; Gr 2 muscle weakness, whole body/generalized; Gr 2 dyspnea |
| 19 | 7.07 | Gr 2 acute vascular leak syndrome; Gr 2 hypertension; Gr 2 hypoalbuminemia; Gr 2 hypocalcemia; Gr 2 dyspnea; Gr 2 hypoxia |

TABLE 4-continued

Dose level and drug-related toxic effects of $DT_{388}IL3$-treated AML patients

| Patient no. | Dose μg/kg/day | Drug-related Gr 2 or higher side effects (CTC toxicity grade) |
|---|---|---|
| 20 | 7.07 | Gr 2 hyperbilirubinemia; Gr 2 hyperglycemia; Gr 2 hypoalbuminemia; Gr 2 hypocalcemia; Gr 2 AST; Gr 2 ALT |
| 21 | 7.07 | Gr 2 hypoalbuminemia, Gr 2 AST, Gr 2 ALT |
| 22 | 7.07 | None |
| 23 | 7.07 | Gr 2 fever; Gr 2 hypocalcemia; Gr 2 hypoalbuminemia; Gr 2 acute vascular leak syndrome |
| 24 | 7.07 | None |
| 25 | 7.07 | Gr 2 hypoalbuminemia |
| 26 | 7.07 | Gr 2 AST |
| 27 | 9 | Gr 2 fever; Gr 2 ALT; Gr 2 hypoalbuminemia |

TABLE 5

$DT_{388}IL3$ Clinical Responses

| Patient no. | Pre-treatment blast % | Overall Response | Length of response (mos) |
|---|---|---|---|
| 9 | 50% | PR | 1 |
| 13 | 69% | MR with 93% reduction* | 2 |
| 14 | 90% | MR with 89% reduction* | 1 |
| 15 | 80% | MR with 90% reduction* | 1 |
| 19 | 30% | CR | ongoing for >6 |
| 23 | 39% | PR | ongoing for >2 |

*Cytoreduction calculated from change in marrow blast index = % blasts × % cellularity.

6.2 Example 2

6.2.1 Patients and Methods

Patients had to have AML based on bone marrow biopsy and either disease, relapsed disease, refractory disease or poor-risk AML (treatment-related, prior MDS, patient age>70 years, or unfavorable cytogenetics and not candidate for allogeneic transplantation). Patients had to have a performance status<2, WBC<10,000/ml, bilirubin<1.5 mg/dL, transaminases<2.5×upper limit of normal, albumin>3 g/dL, creatinine<1.5 mg/dL, adequate cardiac reserve (EF>40%), anti-DT pretreatment serum concentration<2.4 mg/ml, be willing to give informed consent and be treated at an approved site, be willing to use an approved form of birth control while on study, not have concurrent serious medical problems or uncontrolled infections or DIC or pregnancy, not have active CNS leukemia, not have had a myocardial infarction within the past six months, not require oxygen, and not have an allergy to DT. Patients received 15 minute infusions of $DT_{388}IL$-3 three times weekly for two weeks with interpatient dose escalation at doses of 4-12.5 μg/kg/dose.

6.2.2 Results—Patient Characteristics

Seventy-five AML patients have been screened to date and thirty-six patients treated (Table 6). The median age of treated patients was 60 years (range, 25-81 years). There were twenty males and sixteen females. Disease was de novo AML in four, first relapse AML in eleven, second relapse AML in eight, and refractory AML in twelve patients. One patient had MDS. Seven AML patients had a history of MDS, and one had a history of secondary AML. One patient each had previously received an autologous or allogeneic stem cell transplant. Cytogenetics were unfavorable in twelve including the MDS patient, intermediate in twenty-one, and not done in three. Seven patients were treated with 4 mg/kg, eight patients were treated with 5.3 μg/kg, twelve patients treated with 7.1 mg/kg, and eight patients treated with 9.4 μg/kg, one patient treated with 12.5 μg/kg $DT_{388}IL$-3.

TABLE 6

Clinical characteristics of $DT_{388}IL3$-treated AML patients

| Patient no. | Age(yrs)/Sex | Disease Status | Treatment History | Cytogenetics |
|---|---|---|---|---|
| 1 | 38/M | 1st rel | 7 + 3; HiDAC | Normal |
| 2 | 53/F | 2nd rel | 7 + 3/Ida/Ara-C; 7 + 3/Ida/Ara-C; 5 + 3/Ida/Ara-c; Mylotarg | +8 |
| 3[b] | 67/F | 1st rel | Carbo/Taxol; Gleevea then Ida/Cytarabine; Mylotarg | −4, −18, −19, del 5, +7 |
| 4[a] | 67/F | 2nd rel | Ida/Ara-C; Mylotarg; Campath/Cytoxan; Allo stem; Mylotarg; DLI; DLI; Mylotarg; DLI | Normal |
| 5 | 57/M | 1st rel | 7&3/Cytarabine/Dauno; 5&2/Cytarabine/dauno; Cytarabine/Mylotarg; Cytoxan/VP-18 | +13 |
| 6[a] | 54/M | 2nd rel | Ara-C/Ida; Ara-C/Gem/CPT-11; Ara-C/Etoposide; Stem cell transplant; BiSusulphace/VP-18; Autologous stem | −7 |
| 7[b] | 51/M | 2nd rel | 7 + 3 + 3; Ara-C/L-asparaginase; Ara-C/VP-16, Busulfan/VP-16 plus auto stem; Ara-C/Mito/L-asparaginase; Ara-C/Mito/L-asparaginase; Mylotarg | t (6; 12) |
| 8 | 82/M | 1st rel | Cytarabine/Dauno | t(3; 21)(q26; q26) |
| 9 | 83/M | 1st rel | Cytarabine/Dauno | Normal |

TABLE 6-continued

Clinical characteristics of DT$_{388}$IL3-treated AML patients

| Patient no. | Age(yrs)/ Sex | Disease Status | Treatment History | Cytogenetics |
|---|---|---|---|---|
| 10 | 89/M | 1$^{st}$ rel | Dauno/Ara-C; Dauno/Ara-C; Dauno/Ara-C; Dauno/Ara-C | Normal |
| 11 | 54/F | Ref | ERYC/Ida (7 + 3); ERYC | Normal |
| 12 | 81/F | De Novo | | +8, +9 |
| 13 | 76/M | 2$^{nd}$ rel | Ida/Ara-C; VP16/Mito/Ara-C; Mylotarg; Vion/Timidor; Gem/Fludarabine/Mito | Normal |
| 14 | 67/F | Ref | ERYC/Ida (7 + 3) induction | t(11; 18) (q25; q21), del (9) (p22p24); +8 |
| 15 | 25/F | 2$^{nd}$ rel | 7 + 3 induction therapy; minI VP-16/Cytoxan/ Ara-C; CECA re-induction followed by 7 + 3 | t(9; 11) (p22; q23) |
| 16 | 44/F | Ref | HiDAC/dauno; VP-16/Cyclophosphamide | Normal |
| 17 | 62/M | Ref | 7 + 3 Induction therapy; 6 + 2/Cytarabine/Asparaginase; Clorotoxine/Tomodar; Mitn/Gem/Fludarabine | t(1; 4) (q42; q21), t(4; 12) (q12; p13) del (7) (q22) |
| 18 | 62/F | 1$^{st}$ rel | 7 + 3 induction | Normal |
| 19 | 72/F | Ref | 7 + 3 induction | Normal |
| 20 | 62/M | 1$^{st}$ rel | Cytarabine/Ida | acid (2) (p21), acid (3) (p25), −4, −7, sl, del (17) (q23), sdil, del (11) (q23) |
| 21$^b$ | 59/F | 1$^{st}$ rel | Ara-C/dauno; VP-16/cyclo salvage | t (1; 5) |
| 22 | 32/M | Ref | Ara-C/dauno; VP-16/Mito; Ara-C/dauno; VP-16/Cytoxan | del (7) (q22q34) |
| 23 | 73/F | 1$^{st}$ rel | Cyclosporin, daunorubicin, cytarabine | +11, −12, der (17) t (12; 17) (q10; p12) |
| 24 | 33/M | 2$^{nd}$ rel | ADE-10; MACE/Midac; Hydrea/leukophoresis; Cytosine/Ara-C | Normal |
| 25$^b$ | 66/F | Ref | Revlimid, 7 + 3, L-001281814/MK0457 | del (5) (q23), −12, −13, acid (16) (q22), +mar 20 |
| 26 | 73/F | Ref | Ara-C/dauno; 7 + 3 | Normal |
| 27 | 70/F | De Novo | | ND |
| 28 | 60/M | Ref | 7 + 3 | del (5) |
| 29 | 41/F | 2$^{nd}$ rel | 7 + 3; Hi-Dos Cytarabine; 7 + 3 re-induction | Normal |
| 30 | 32/M | Ref | HiDAC/dauno; VP-16/Cyclophosphamide; HiDAC | ND |
| 31$^b$ | 77/M | De Novo | | Normal |
| 32$^b$ | 72/M | Ref | Ara-C | −Y |
| 33 | 78/M | 1$^{st}$ rel | 7 + 3; Hi-Dos Cytarabine | Normal |
| 34 | 77/M | De Novo | | ND |
| 35$^b$ | 65/M | Ref | 7 + 3, High dose Ara-C, PT-523 | (q5), del (7), t (16; 17) |
| 36 | 71/M | MDS | 6-azacitidine; decitabine | −7 |

$^a$Patient 4 had a aliogenetic transplant, and patient 6 had a autologous transplant.
$^b$Patient 3 had a history of secondary AML Patient 7, 21, 25, 31, 32, and 35 had a prior history of MDS.

6.2.3 Results—Toxicities

Figure 5:
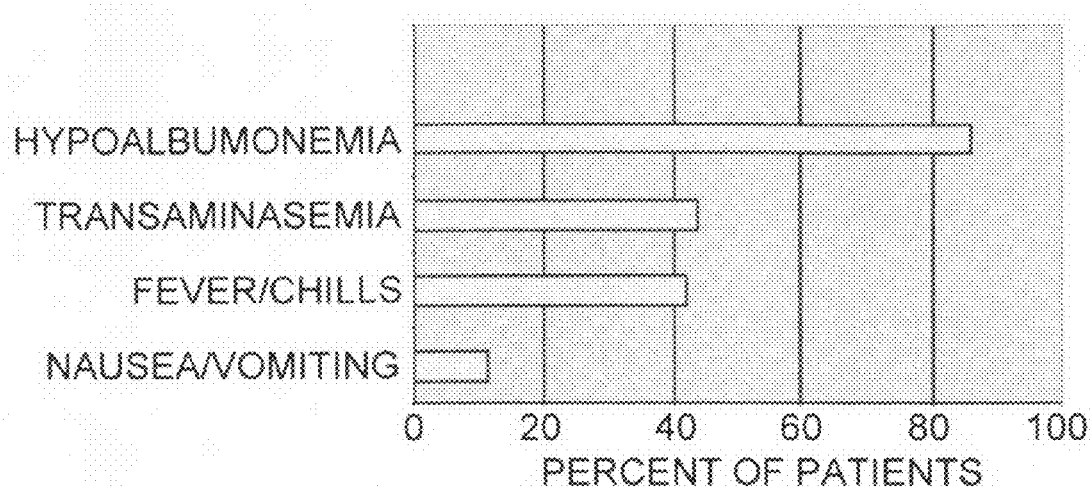
Figure 6A:
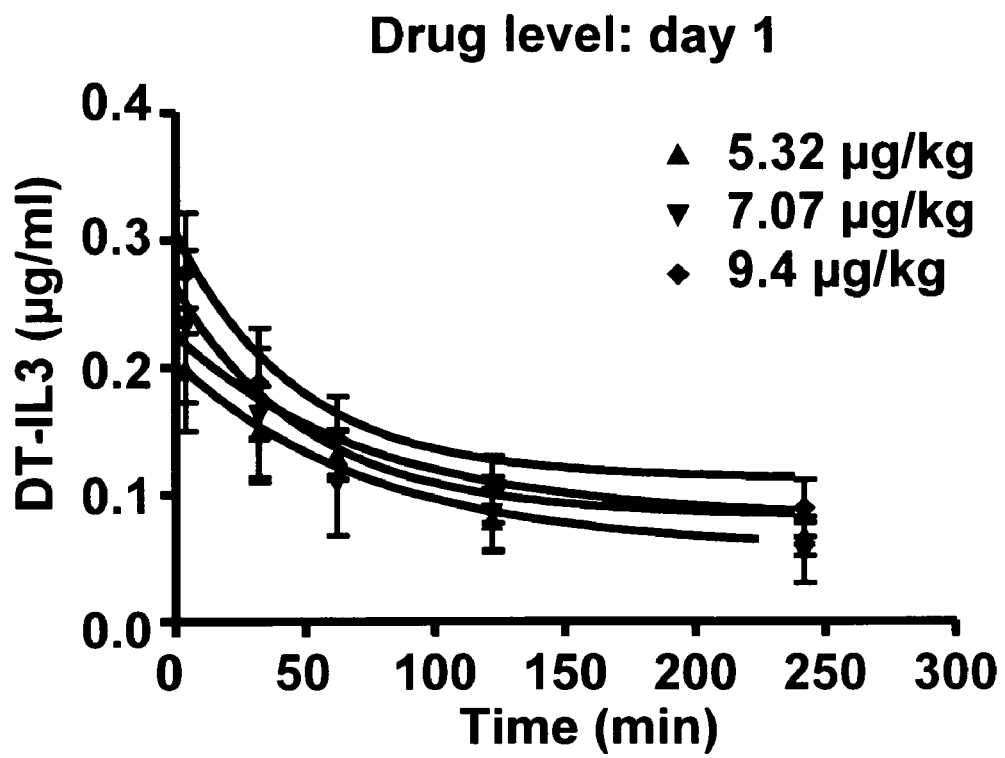
Figure 6B:
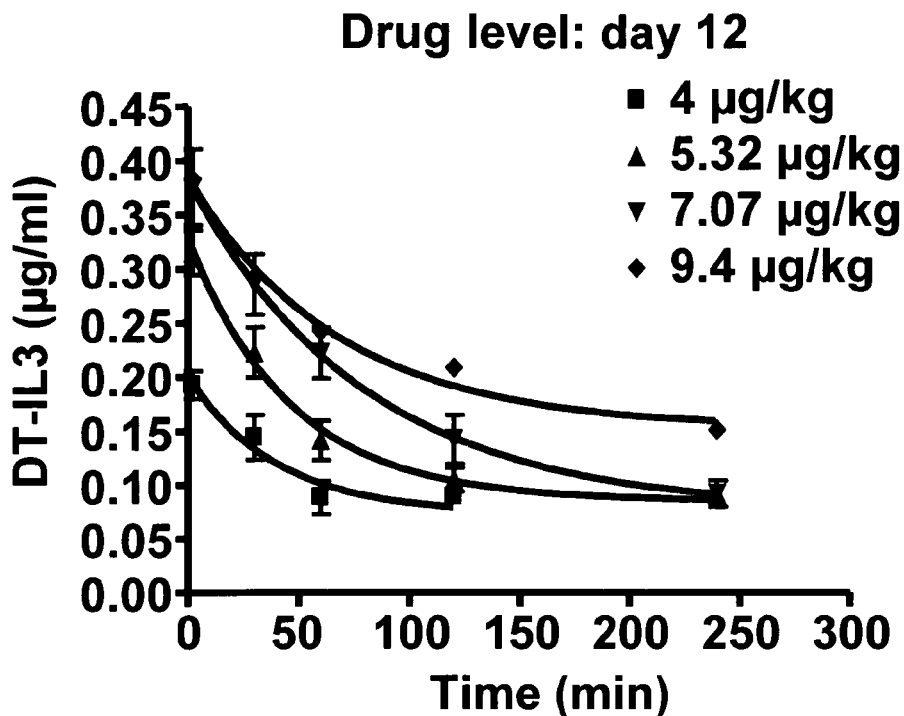

Drug-related toxicities were mild to moderate and transient including fever, chills, hypotension, vascular leak syndrome, hypoxemia, hypocalcemia, transaminasemia and hypoalbuminemia (Table 7 and FIG. 5). There is no correlation of dose level with toxicity incidence or grade.

TABLE 7

Results of DT388IL3 treated patients-toxicities, pharmacokinetics, immune response, and clinical response*

| Patient No. | Dose level (ug/kg) | Toxicities Gr2 CTCV3 | Cmax d1/d12 (mg/mL) | | Anti-DT antibody (mg/mL) | | | Clinical Response |
|---|---|---|---|---|---|---|---|---|
| | | | | | d1 | d15 | d30 | |
| 1 | 4 | N-V, Trans | 0 | 0 | 0.8 | 23 | 235 | 0 |
| 2 | 4 | 0 | 0 | 0 | 2.5 | ND | ND | 0 |
| 3 | 4 | F, N-V, Alb, Hypo | 0 | 0.18 | 0 | ND | 36 | 0 |
| 4 | 4 | F, Alb | ND | ND | 0 | ND | ND | 0 |
| 5 | 4 | F, Alb | ND | ND | 0 | ND | 48 | 0 |
| 6 | 4 | Hypo | ND | ND | 0.9 | ND | 36 | 0 |
| 7 | 4 | Alb | 0 | 0 | 2.2 | 1 | 6.2 | 0 |
| 8 | 5.32 | Alb | 0.19 | 0 | 1 | 221 | 263 | 0 |
| 9 | 5.32 | Alb, Trans | 0.14 | 0.15 | 0.8 | 440 | ND | PR |
| 10 | 5.32 | Alb | 0.22 | ND | 0.5 | ND | 1.1 | 0 |
| 11 | 5.32 | F, Alb, Trans | 0 | ND | 2.5 | ND | ND | 0 |
| 12 | 5.32 | Hypo, F, Alb | 0.34 | 0 | 1.3 | 600 | ND | 0 |
| 13 | 5.32 | Alb | 0 | 0.3 | 1.5 | ND | ND | MR |
| 14 | 5.32 | Alb, Trans | 0.38 | 0.36 | 0.3 | 0.3 | ND | MR |
| 15 | 5.32 | Alb, Trans | 0.06 | 0.29 | 0 | 1.6 | 29 | MR |
| 16 | 7.07 | Alb, Trans | ND | 0.21 | 1 | 0 | ND | 0 |
| 17 | 7.07 | Alb | ND | ND | 1.2 | ND | ND | 0 |
| 18 | 7.07 | F, Alb, Dysp | 0.22 | 0.37 | 0.7 | 0.4 | ND | 0 |
| 19 | 7.07 | VLS, Alb, Dysp | 0.32 | 0.54 | 0.8 | 8.3 | 22.4 | CR |
| 20 | 7.07 | Alb, Trans | 0.48 | ND | 0.4 | ND | ND | 0 |
| 21 | 7.07 | Alb, Trans | 0.08 | 0.35 | 2.1 | 1.5 | 4.2 | 0 |

TABLE 7-continued

Results of DT388IL3 treated patients-toxicities, pharmacokinetics, immune response, and clinical response*

| Patient No. | Dose level (ug/kg) | Toxicities Gr2 CTCV3 | Cmax d1/d12 (mg/mL) | | Anti-DT antibody (mg/mL) | | | Clinical Response |
|---|---|---|---|---|---|---|---|---|
| | | | | | d1 | d15 | d30 | |
| 22 | 7.07 | Alb, Trans | 0.13 | 0.29 | 1.7 | 1.2 | ND | 0 |
| 23 | 7.07 | F, Alb, VLS | 0.61 | ND | 2.2 | 32 | 104 | PR |
| 24 | 7.07 | 0 | 0 | 0.38 | 4.3 | ND | 4 | 0 |
| 25 | 7.07 | Alb | 0.11 | ND | 3.8 | ND | ND | 0 |
| 26 | 7.07 | F, alb, Trans | 0.23 | ND | 0.5 | ND | ND | 0 |
| 27 | 9.4 | F, Alb, Trans | 0.18 | ND | 3 | ND | ND | 0 |
| 28 | 9.4 | F, Alb | 0.27 | ND | 1.3 | 300 | ND | 0 |
| 29 | 7.07 | F, Alb | ND | ND | 1.5 | ND | ND | 0 |
| 30 | 9.4 | Alb | 0.15 | 0.32 | 3 | 0.8 | ND | 0 |
| 31 | 9.4 | F, Trans | 0.23 | ND | 2.3 | ND | ND | 0 |
| 32 | 9.4 | Alb, Trans | 0.26 | 0.38 | 2.2 | 3.1 | ND | 0 |
| 33 | 9.4 | Alb, Trans | 0.37 | ND | 1.2 | ND | ND | 0 |
| 34 | 9.4 | Alb, Trans | 0.55 | ND | 2.2 | ND | 306 | 0 |
| 35 | 9.4 | Alb | 0.23 | 0 | 0.8 | 252 | ND | 0 |
| 38 | 12.5 | Alb, Trans | 0.34 | ND | 1.3 | 11.2 | 16.8 | PR |

*F = fever, N-V = nausea and vomiting, Trans = transaminasemia, VLS = vascular leak syndrome, Alb = hypoalbuminemia, Hypo = hypotension, Dysp = dyspnea, ND = Not determined, MR = minimal response, PR = partial response, CR = complete response.

6.2.4 Results—Immune Response

Pretreatment antibody titers ranged from 0 to 4.3 µg/ml (mean=2.3 µg/ml); day 15 antibody titers were 0 to 600 µg/ml (mean=92 µg/ml); day 30 antibody titers were 1.1 to 306 µg/ml (mean=81 µg/ml). Based on high antibody titers of >8 µg/ml, all 25 samples were low pretreatment; nine samples were low at day 15 and nine samples high at day 15; four samples were low at day 30 and ten samples high at day 30. Cmax did not correlate with response (p=0.23).

6.2.5 Results—Clinical Response

Among thirty-six evaluable patients, the following were observed: one cytogenetic AML CR for 8 months; two AML partial remissions (PRs) lasting one and three months; three AML minimal responses with clearance of peripheral blasts and marrow blast cytoreductions of 89%, 90% and 93% lasting one to two months; and one MDS partial remission lasting greater than one month with reduction of blasts from 10% to 2% and normalization of peripheral counts (Table 8 and FIG. 8A-D).

TABLE 8

$DT_{388}IL3$ Clinical Responses

| Patient no. | Dose Level | Pre-treatment blast % | Overall Response | Length of response (mos) |
|---|---|---|---|---|
| 9 | 5.32 | 50% | PR | 1 |
| 13 | 5.32 | 69% | MR with 93% reduction* | 2 |
| 14 | 5.32 | 90% | MR with 89% reduction* | 1 |
| 15 | 5.32 | 80% | MR with 90% reduction* | 1 |
| 19 | 7.07 | 30% | CR | 8 |
| 23 | 7.07 | 39% | PR | 3 |
| 36 | 12.5 | 10% | PR | >1 |

*Cytoreduction calculated from change in marrow blast index = % blasts × % cellularity.

7. EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent, or patent application was specifically and individually indicated to be incorporated herein by reference.

Citation or discussion of a reference herein shall not be construed as an admission that such is prior art to the present invention.

I claim:

1. A method for reducing blasts in a human diagnosed with myelodysplastic syndrome (MDS), comprising administering to a human in need of such reduction a pharmaceutical composition comprising a human interleukin 3 (IL-3)-diphtheria toxin conjugate in which the conjugate is administered at a dose of about 0.1 µg/kg to about 50 µg/kg.

2. The method of claim 1, wherein the method results in an improvement in hematopoietic function and/or an improvement in the marrow blast index.

3. The method of claim 2, wherein the reduction is measured by conventional measurements, including blood tests; blast count; blast percentage; physical examination; complete blood count; flow cytometric analyses; bone marrow aspirate; bone marrow analyses; hematopoietic function; marrow blast index; the amount of normal white blood cells, red blood cells, and/or platelets; histology; immunohistochemistry; frequency of transfusion; and/or bone marrow biopsy.

4. The method of claim 1, wherein the blasts express the IL-3 receptor.

5. The method of claim 4, wherein the reduction reduces the amount of IL-3R-expressing blasts.

6. The method of claim 1, wherein the reduction reduces the amount of IL-3R-expressing cells.

7. The method of claim 1, wherein the conjugate is administered at a dose of about 4 µg/kg to about 50 µg/kg.

8. The method of claim 1, wherein the conjugate is administered at a dose of about 4 µg/kg to about 12.5 µg/kg.

9. The method of claim 1, wherein the conjugate is administered at a dose of about 4 µg/kg to about 20 µg/kg.

10. The method of claim 1, wherein the conjugate is administered at a dose of about 5.3 µg/kg.

11. The method of claim 1, wherein the conjugate is administered at a dose of about 7.1 µg/kg.

12. The method of claim 1, wherein the conjugate is administered at a dose of about 9.4 µg/kg.

13. The method of claim 1, wherein the conjugate is administered at a dose of about 12.5 µg/kg.

14. The method of claim 1, wherein the conjugate is administered at a dose that is the maximum tolerated dose.

15. The method of claim 1, wherein the conjugate is administered at least two times a week.

16. The method of claim 9, wherein the conjugate is administered at least three times a week.

17. The method of claim 1, wherein the conjugate is administered over a period of two weeks or more.

18. The method of claim 16, wherein the conjugate is administered over a period of two weeks or more.

19. The method of claim 1, wherein the human has abnormal cytogenetics.

20. The method of claim 1, wherein the conjugate is a chemical conjugate.

21. The method of claim 1, wherein the conjugate is a recombinantly expressed protein.

22. The method of claim 21, wherein the conjugate is expressed as a single polypeptide comprising the catalytic and translocation domains of diphtheria toxin and human IL-3.

23. The method of claim 22, wherein the conjugate comprises amino acid residues 1 to 388 of diphtheria toxin linked via a peptide bond to human IL-3.

24. The method of claim 22, wherein the conjugate is administered at a dose of about 4 µg/kg to about 12.5 µg/kg.

25. The method of claim 22, wherein the conjugate is administered at a dose of about 4 µg/kg to about 20 µg/kg.

26. The method of claim 1, wherein the conjugate is administered once every day for five days.

27. The method of claim 26, wherein the conjugate is administered for multiple cycles.

28. A method for improving hematopoietic function in a human diagnosed with MDS, comprising administering to a human in need of such improvement a pharmaceutical composition comprising a human IL-3-diphtheria toxin conjugate in which the conjugate is administered at a dose of about 0.1 µg/kg to about 50 µg/kg.

29. The method of claim 28, wherein the method results in a stabilization in the amount of blasts and/or an improvement in the marrow blast index.

30. The method of claim 29, wherein the stabilization is measured by conventional measurements, including blood tests; blast count; blast percentage; physical examination; complete blood count; flow cytometric analyses; bone marrow aspirate; bone marrow analyses; hematopoietic function; marrow blast index; the amount of normal white blood cells, red blood cells, and/or platelets; histology; immunohistochemistry; frequency of transfusion; and/or bone marrow biopsy.

31. The method of claim 28, wherein the conjugate is a chemical conjugate.

32. The method of claim 28, wherein the conjugate is a recombinantly expressed protein.

33. The method of claim 32, wherein the conjugate is expressed as a single polypeptide comprising the catalytic and translocation domains of diphtheria toxin and human IL-3.

34. The method of claim 33, wherein the conjugate comprises amino acid residues 1 to 388 of diphtheria toxin linked via a peptide bond to human IL-3.

35. The method of claim 28, wherein the conjugate is administered at a dose of about 4 µg/kg to about 50 µg/kg.

36. The method of claim 28, wherein the conjugate is administered at a dose of about 4 µg/kg to about 12.5 µg/kg.

37. The method of claim 28, wherein the conjugate is administered at a dose of about 4 µg/kg to about 20 µg/kg.

38. The method of claim 28, wherein the conjugate is administered at a dose that is the maximum tolerated dose.

39. The method of claim 37, wherein the conjugate is administered at least two times a week.

40. The method of claim 39, wherein the conjugate is administered over a period of two weeks or more.

41. The method of claim 28, wherein the conjugate is administered once every day for five days.

42. The method of claim 41, wherein the conjugate is administered for multiple cycles.

43. The method of claim 28, wherein the conjugate is administered at a dose of about 5.3 µg/kg.

44. The method of claim 28, wherein the conjugate is administered at a dose of about 7.1 µg/kg.

45. The method of claim 28, wherein the conjugate is administered at a dose of about 9.4 µg/kg.

46. The method of claim 28, wherein the conjugate is administered at a dose of about 12.5 µg/kg.

47. The method of claim 1 or 28, wherein the MDS is refractory.

48. The method of claim 1 or 28, wherein the MDS is in remission.

49. The method of claim 1 or 28, wherein the human has been previously treated with a therapeutic agent and/or has undergone radiation therapy.

50. The method of claim 1 or 28, wherein the human is currently being administered a therapeutic agent and/or is undergoing radiation therapy.

51. The method of claim 1 or 28, wherein the human has relapsed from MDS.

52. The method of claim 1 or 28, wherein the human has failed MDS treatment.

53. The method of claim 1 or 28, wherein the human is elderly.

54. The method of claim 53, wherein the human is susceptible to adverse reactions from other therapies.

55. The method of claim 1 or 28, wherein the human is refractory to chemotherapy.

56. The method of claim 1 or 28, wherein the human has not been previously treated for MDS.

\* \* \* \* \*